US007718615B2

(12) United States Patent
Markland, Jr. et al.

(10) Patent No.: US 7,718,615 B2
(45) Date of Patent: *May 18, 2010

(54) CONTORTROSTATIN (CN) AND METHODS FOR ITS USE IN PREVENTING METASTASIS AND OTHER CONDITIONS

(75) Inventors: Francis S. Markland, Jr., Manhattan Beach, CA (US); Matthew Ritter, Cypress, CA (US)

(73) Assignee: University of Southern California, Los Angeles, CA (US)

( * ) Notice: Subject to any disclaimer, the term of this patent is extended or adjusted under 35 U.S.C. 154(b) by 693 days.

This patent is subject to a terminal disclaimer.

(21) Appl. No.: 11/544,190

(22) Filed: Oct. 5, 2006

(65) Prior Publication Data

US 2007/0123458 A1 May 31, 2007

Related U.S. Application Data

(60) Division of application No. 10/712,584, filed on Nov. 12, 2003, now Pat. No. 7,220,724, which is a continuation of application No. 09/591,552, filed on Jun. 8, 2000, now abandoned, which is a continuation-in-part of application No. 09/460,295, filed on Dec. 10, 1999, now Pat. No. 6,710,030, which is a continuation-in-part of application No. 09/163,047, filed on Sep. 29, 1998, now abandoned, which is a continuation-in-part of application No. 08/745,603, filed on Nov. 8, 1996, now Pat. No. 5,814,609, which is a continuation-in-part of application No. 08/632,691, filed on Apr. 15, 1996, now Pat. No. 5,731,288, which is a division of application No. 08/540,423, filed on Oct. 10, 1995, now abandoned, which is a continuation of application No. 08/141,321, filed on Oct. 22, 1993, now abandoned.

(51) Int. Cl.
*A61K 38/00* (2006.01)

(52) U.S. Cl. .......................................... 514/12; 530/324

(58) Field of Classification Search ....................... None
See application file for complete search history.

(56) References Cited

U.S. PATENT DOCUMENTS

| 5,731,288 A | 3/1998 | Markland et al. |
| 5,814,609 A | 9/1998 | Markland et al. |
| 6,710,030 B1 | 3/2004 | Markland et al. |

FOREIGN PATENT DOCUMENTS

| EP | 323722 | 7/1989 |
| FR | 2736266 | 1/1997 |
| WO | WO 9008772 | 8/1990 |
| WO | WO 00/18421 | 4/2000 |

OTHER PUBLICATIONS

Albelda et al., "Identification and Characterization of Cell-Substratum Adhesion Receptors on Cultured Human Endothelial Cells," J Clin Invest. Jun. 1989; 83(6):1992-2002.
Bauer et al., "Motility of Fibronectin REceoptor-deficient Cells on Fibronectin and Vitronectin: Collaborative Interactions among Integrins," The Journal of Cell Biology, vol. 116, No. 2 1992.
Belisario, M.A. et al., "Immobilised echistatin promotes platelet adhesion and protein tyrosine phosphorylation," Biochimica et Biophysica Acta 1497 227-236 (2000).
Bhattacharya, S., et al., "Soluble Ligands of the $\alpha_v\beta_3$ Integrin Mediate Enhanced Tyrosine Phosphorylation of Multiple Proteins in Adherent Bovine Pulmonary Artery Endothelial Cells." The Journal of Biological Chemistry 270(28): 16781-16787 (1995).
Chung, G.H., et al., "Peptide derived from Korean salmosa viper venom—useful as blood platelet aggregation inhibitor for the management of thrombosis," Derwent Record for FR 2736266 (1997).
Clark, E.A., et al., "Structurally Distinct Disintegrins Contortrostatin and Multisquamatin Differentially Regulate Platelet Tyrosine Phosphorylation," The Journal of Biological Chemistry 269 (35):21940-21943 (1994).
Cousins G. et al., "Contortrostatin prevents reocclusion after thrombolytic therapy in a canine model of carotid artery thrombosis," Faseb J., vol. 9, No. 4, 1995 abstract.
Fujisawa, Y., et al., "Disintegrin, halystatin, from agkistrodon halys, is a potent inhibitor of bone resorption and platelet aggregation," Database Embl, Accession No. D28871 Apr. 8, 1994.
Halvorson et al., "The Vitronectin Receptor ($\alpha_v\beta_3$) as an Example for the Role of Integrins in T Lymphocyte Stimulation," Immunologic Research (1996), 15(1), 16-29.
Hauzenberger et al., "Triggering of Motile Behavior in T Lymphocytes via Cross-Linking of $\alpha_4\beta_1$ and $\alpha_L\beta_2$," Journal of Immunology (1997), 158(1), 76-84.
Huang, M., et al., "Adhesive Ligand Binding to Integrin Alpha IIb Beta 3 Stimulates Tyrosine Phosphorylation of Novel Protein Substrates before Phosphorylation of pp 1125 FAK," The Journal of Cell Biology 122(2):473-483 (1993).
International Search Report for Application No. PCT/US00/33367.
International Search Report for Application No. PCT/US99/22608.
Kamiguti AS et al., "Proteolytic cleavage of the beta1 subunit of platelet alpha2beta1 integrin by the metalloproteinase jararhagin compromises collagen-stimulated phosphorylation of pp72," J Biol Chem. Dec. 19, 1997;272(51):32599-605.
Kang, I-C., et al., "A novel disintegrin salmosin inhibits tumor angiogenesis," Cancer Research 59:3754-60 (1999).
Kornberg, L., et al., "Cell Adhesion or Integrin Clustering Increases Phosphorylation of a Focal Adhesion-associated Tyrosine Kinase" The Journal of Biological Chemistry 267(33): 23439-23442 (1992).
Kornberg, L., et al., "Signal transduction by integrins: Increased protein tyrosine phosphorylation caused by clustering of Beta1 integrins," Proc. Natl. Acad. Sci. USA 88:8392-8396 (1991).

(Continued)

*Primary Examiner*—Michael Borin
(74) *Attorney, Agent, or Firm*—Foley & Lardner LLP

(57) ABSTRACT

Contortrostatin, a homodimeric disintegrin, modulates the adhesion, motility, and invasiveness of integrin expressing tumor cells. When formulated as a pharmaceutically acceptable composition, the proteins can be used to treat patients by inhibiting or disrupting disease processes associated with an integrin binding to an αvβ3 or αvβ5 integrin.

3 Claims, 27 Drawing Sheets

OTHER PUBLICATIONS

C. Chandra Kumar, et al., "Biochemical Characterization of the Binding of Echistatin to Integrin $\alpha_v\beta_3$ Receptor," The Journal of Pharmacology and Experimental Therapeutics vol. 283, No. 2: pp. 843-853 (1997).

Lipfert, L., et al., "Integrin-Dependent Phosphorylation and activatin of the Protein Tyrosine Kinase pp$125^{FAK}$ in Platelets." The Journal of Cell Biology 119(4):905-912 (1992).

Marcinkiewicz, C. et al., "EC3, a Novel Heterodimeric Disintegrin from Echis Carinatus Venom, Inhabits a4 and a5 integrins in an RGD-independent Manner," The Journal of Biological Chemistry 274 (18): 12468-12473 (1999).

Markland, FS et al., "A Novel Snake Venom Disintegrin That Inhibits Human Ovarian Cancer Dissemination and Angiogenesis in an Orthotopic Nude Mouse Model," Haemostatsis. May-Dec. 2001;31 (3-6):183-91.

Markland, F.S. et al., "Snake Venom Disintegrin: An Effective Inhibitor of Breast Cancer Growth and Dissemination." Chapter 18 in "Natural and Selected Synthetic Toxins, Biological Implications," Tu, A.T. et al. editors, ACS Symposium Series 745:262-282 (2000).

Mercer B. et al., "Contortrostatin, a homodimeric snake venom disintegrin, is a potent inhibitor of osteoclast attachment," J. Bone Min. Res., vol. 13, No. 3, Mar. 1998. see abstract and p. 410 left col.

Miyamoto, S., et al., "Integrin Function: Molecular Hierarchies of Cytoskeletal and Signaling Molecules," The Journal of Cell Biology 131(3): 791-805 (1995).

Ritter, Matthew R. et al., "Contortrostatin Activates ERK2 and Tyrosine Phosphorylation Events via Distinct Pathways," Biochemical and Biophysical Research Communications 274, 142-148 (2000).

Ritter MR et al., "Contortrostatin, a snake venom disintegrin, induces $\alpha_v\beta_3$ mediated tyrosine phosphorylation of CAS and FAK in tumor cells," J Cell Biochem. Jul. 19, 2000;79(1):28-37.

Ritter, MR et al., "Contortrostatin, a Homodimeric Disintegrin, Actively Disrupts Focal Adhesion and Cytoskeletal Structure and Inhibits Cell Motility Through a Novel Mechanism," Cell Commun. Adhes. 2001;8(2):71-86.

Ritter MR et al., "Differential regulation of tyrosine phosphorylation in tumor cells by contortrostatin, a homodimeric disintegrin, and monomeric disintegrins echistatin and flavoridin," Toxicon. Feb.-Mar. 2001;39(2-3):283-9.

Ritter, M.R. et al., "The Homodimeric Disintegrin Contortrostatin Activates Phosphorylation of FAK and CAS," Molecular Biology of the Cell, Supplement to Molecular Biology of the Cell 10:150a-867 (1999).

Sanderson, C. et al., "Vaccinia Virus Induces Ca2 + -Independent Cell-Matirx Adhesion during the Motile Phase of Infection," Journal of Virology, vol. 72, No. 12 pp. 9924-9933, Dec. 1998.

Schmitmeier S. et al., "Anti-invasive Effect of Contortrostatin, a Snake Venom Disintegrin, and TNF-$\alpha$ on Malignant Glioma Cells," Anticancer Res. Nov.-Dec. 2000;20(6B):4227-33.

Sheu, J.-R. et al., "Inhibition of angiogenesis in vitro and in vivo: comparison of the relative activities of triflavin, an Arg-Gly-Asp-containing peptide and . . . antibody," Biochimica et Biophysica Acta 1336 445-454 (1997).

Sheu, J.R. et al., "Triflavin, an Arg-Gly-Asp-Containing Peptide, Inhibits the Adhesion of Tumor Cells to Matrix Proteins via Binding to Multiple Integrin Receoptors Expressed on Human Hepatoma Cells (44038)," Triflavin and Human Hepatoma Cell Adhesion 71-79 (1996).

Staiano, N. et al., "Echistatin induces decrease of pp 125 FAK phosphorylation, disassembly of actin cytoskeleton and focal adhesions, and detachment of fibronectin-adherent melanoma cells," European Journal of Cell Biology 73:298-305 (1997).

Supplementary Partial European Search Report for US9922608.

Supplementary Partial European Search Report for US0033367.

Trikha, et al. "A novel platelet aggregation inhibitor from southern copperhead snake venom," Fibrinolysis, International Journal of Fibrinolysis and Thrombolysis, 266 vol. 4, suppl. 1 Jun. 1990.

Trikha, et al. "Characterization of a novel platelet aggregation inhibitor (contortrostatin) from the southern copperhead snake venom," The Journal of the American Society of Hematology, Blood vol. 76, No. 10 (Suppl 1), 479a, Nov. 15, 1990.

Trikha M et al., "Contortrostatin, a snake venom disintegrin, inhibits beta 1 integrin-mediated Human metastatic melanoma cell adhesion and blocks experimental metastasis," Cancer Res. Sep. 15, 1994;54(18):4993-8.

Yeh Chia Hsin, et al., "Accutin, a New Disintegrin, Inhibits Angiogenesis In Vitro and In Vivo by Acting as Integrin $\alpha_v\beta_3$ Antagonist and Inducing Apoptosis" The American Society of Hematology, Blood, vol. 92, No. 9, pp. 3268-3276 Nov. 1, 1998.

Yeh Chia Hsin, "A new short chain RGD-containing disintegrin, accutin, inhibits the common pathway of human platelet aggregation," Biochimica et Biophysica Acta 1425: pp. 493-504 (1998).

Zhou, Q. et al., "Contortrostatin, a dimeric disintegrin from *Agkistrodon contortrix contortrix*, inhibits angiogenesis," Angiogenesis 3:259-269 (1999).

Zhou, Q. et al., "Contortrostatin, a dimeric disintegrin from *Agkistrodon contortrix contortrix*, inhibits breast cancer progression," Breast Cancer Research and Treatment 61:249-260 (2000).

Zhou, Q. et al., "Contortrostatin, a Homodimeric Disintegrin, Binds to Integrin avB5," Biochemical and Biophysical research Communications, 267:350-355 (2000).

Zhou Q. et al., "Contortrostatin (CN), A snake venom disintegrin, is an inhibitor of kaposi's sarcoma progression," Proceedings of the Annual Meeting of the American Association for Cancer Research, New York, NY. US vol. 39, Apr. 28, 1998 p. 299, abstract.

Zhou Q. et al., "Contortrostatin, a snake venom protein, which is an inhibitor of breast cancer progression," Molecular Biology of the Cell, Bethesda MD. US vol. 7, no. Suppl, Dec. 7, 1996. p. 425A, abstract.

Zhou, Q. et al., "Molecular Cloning and Functional Expression of Contortrostatin, a Homodimeric Disintegrin from Southern Copperhead Snake Venom," Archives of Biochemistry and Biophysics 375(2):278-288 (2000).

FIG. 3A

```
                11              20              29              38              47              56
5' GA ATT CGG GGT CAA TAG AGG AAG AGC TCA AGT TGG CTT GAA AGC AGG AAG AGA TTG 65              74              83              92             101             110
   CCT GTC TTC CAG CCA AAT CCA GCC GCC AAA ATG ATC CAG GTT CTC TTG GTC ACT
                                                  --- --- --- --- --- --- --- ---
[1]                                                M   I   Q   V   L   L   V   T  [8]

119             128             137             146             155             164
   CTA TGC TTA GCA GCT TTT CCT TAT CAA GGG AGC TCT ATA ATC CTG GAA TCT GGG
   --- --- --- --- --- --- --- --- --- --- --- --- --- --- --- --- --- ---
[9] L   C   L   A   A   F   P   Y   Q   G   S   S   I   I   L   E   S   G  [26]

173             182             191             200             209             218
   AAT GTT AAT GAT TAT GAA GTA CTG TAT CCA CAA AAA GTC ACT GCA TTG CCC AAA
   --- --- --- --- --- --- --- --- --- --- --- --- --- --- --- --- --- ---
[27] N   V   N   D   Y   E   V   L   Y   P   Q   K   V   T   A   L   P   K  [44]

227             236             245             254             263             272
   GGA GCA GTT CAG CCA AAG TAT GAA GAC ACC ATG CAA TAT GAA TTT AAA GTG AAT
   --- --- --- --- --- --- --- --- --- --- --- --- --- --- --- --- --- ---
[45] G   A   V   Q   P   K   Y   E   D   T   M   Q   Y   E   F   K   V   N  [62]

281             290             299             308             317             326
   GGA GAG CCA GTG GTC CTT CAC CTG GAA AAA AAT AAA GGA CTT TTT TCA AAA GAT
   --- --- --- --- --- --- --- --- --- --- --- --- --- --- --- --- --- ---
[63] G   E   P   V   V   L   H   L   E   K   N   K   G   L   F   S   K   D  [80]

335             344             353             362             371             380
   TAC AGC GAG ACT CAT TAT TCC TCT GAT GGC AGA AAA ATT ACA ACA AAC CCT CCG
   --- --- --- --- --- --- --- --- --- --- --- --- --- --- --- --- --- ---
[81] Y   S   E   T   H   Y   S   S   D   G   R   K   I   T   T   N   P   P  [98]

389             398             407             416             425             434
   GTT GAG GAT CAC TGC TAT TAT CAT GGA CGC ATC CAG AAT GAT GCT GAC TCA ACT
   --- --- --- --- --- --- --- --- --- --- --- --- --- --- --- --- --- ---
[99] V   E   D   H   C   Y   Y   H   G   R   I   Q   N   D   A   D   S   T [116]

443             452             461
   GCA AGC ATC AGT GCA TGC AAC GGT TTG AAA GGA CAT TTC AAG CTT CAA GGG GAG
   --- --- --- --- --- --- --- --- --- --- --- --- --- --- --- --- --- ---
[117]A   S   I   S   A   C   N   G   L   K   G   H   F   K   L   Q   G   E [134]

497             506             515             524             533             542
   ACG TAC CTT ATT GAA CCC TTG AAG CTT TCC GAC AGT GAA GCC CAT GCA GTC TAC
   --- --- --- --- --- --- --- --- --- --- --- --- --- --- --- --- --- ---
[135]T   Y   L   I   E   P   L   K   L   S   D   S   E   A   H   A   V   Y [152]

551             560             569             578             587             596
   AAA TAT GAA AAC GTA GAA AAA GAA GAT CAG GCC CCC AAA ATG TGT GGG GTA ACC
   --- --- --- --- --- --- --- --- --- --- --- --- --- --- --- --- --- ---
[153]K   Y   E   N   V   E   K   E   D   Q   A   P   K   M   C   G   V   T [170]
```

FIG. 3B

```
          605            614            623            632            641            650
      CAG ACT AAT TGG GAA TCA GAT GAG CCC ATC AAA AAG GCC TCT CAG TTA AAT CTT
      --- --- --- --- --- --- --- --- --- --- --- --- --- --- --- --- --- ---
[171]  Q   T   N   W   E   S   D   E   P   I   K   K   A   S   Q   L   N   L  [188]

659            668            677            686            695            704
      ACT CCT GAA CAA CAA GGA TTC CCC CAA AGA TAC ATT GAG CTT GTT GTA GTT GCA
      --- --- --- --- --- --- --- --- --- --- --- --- --- --- --- --- --- ---
[189]  T   P   E   Q   Q   G   F   P   Q   R   Y   I   E   L   V   V   V   A  [206]

713            722            731            740            749            758
      GAT CAC AGA ATG TTC ACG AAA TAC AAC GGC AAT TTA AAT ACT ATT AGA ATA TGG
      --- --- --- --- --- --- --- --- --- --- --- --- --- --- --- --- --- ---
[207]  D   H   R   M   F   T   K   Y   N   G   N   L   N   T   I   R   I   W  [224]

767            776            785            794            803            812
      GTA CAT GAA CTT GTC AAC ACT ATG AAT GTG TTT TAC AGA CCT TTG AAT ATT CGT
      --- --- --- --- --- --- --- --- --- --- --- --- --- --- --- --- --- ---
[225]  V   H   E   L   V   N   T   M   N   V   F   Y   R   P   L   N   I   R  [242]

821            830            839            848            857            866
      GTC TCA CTG ACT GAC CTA GAA GTT TGG TCA GAC CAA GAT TTG ATC AAC GTG CAG
      --- --- --- --- --- --- --- --- --- --- --- --- --- --- --- --- --- ---
[243]  V   S   L   T   D   L   E   V   W   S   D   Q   D   L   I   N   V   Q  [260]

875            884            893            902            911            920
      CCA GCA GCG GCT GAT ACT TTG GAA GCA TTT GGA GAC TGG AGA GAG ACA GTC TTG
      --- --- --- --- --- --- --- --- --- --- --- --- --- --- --- --- --- ---
[261]  P   A   A   A   D   T   L   E   A   F   G   D   W   R   E   T   V   L  [278]

929            938            947            956            965            974
      CTG AAT CGC ATA AGT CAT GAT AAT GCT CAG TTA CTC ACG GCC ATT GAG CTT GAT
      --- --- --- --- --- --- --- --- --- --- --- --- --- --- --- --- --- ---
[279]  L   N   R   I   S   H   D   N   A   Q   L   L   T   A   I   E   L   D  [296]

983            992           1001           1010           1019           1028
      GGA GAA ACT ATA GGA TTG GCT AAC AGG GGC ACC ATG TGC GAC CCG AAG CTT TCT
      --- --- --- --- --- --- --- --- --- --- --- --- --- --- --- --- --- ---
[297]  G   E   T   I   G   L   A   N   R   G   T   M   C   D   P   K   L   S  [314]

1037           1046           1055           1064           1073           1082
      ACA GGA ATT GTT CAG GAT CAT AGT GCA ATA AAT CTT TGG GTT GCA GTT ACA ATG
      --- --- --- --- --- --- --- --- --- --- --- --- --- --- --- --- --- ---
[315]  T   G   I   V   Q   D   H   S   A   I   N   L   W   V   A   V   T   M  [332]

1091           1100           1109           1118           1127           1136
      GCC CAT GAG ATG GGT CAT AAT CTG GGT ATT AGT CAC GAT GGA AAT CAG TGT CAT
      --- --- --- --- --- --- --- --- --- --- --- --- --- --- --- --- --- ---
[333]  A   H   E   M   G   H   N   L   G   I   S   H   D   G   N   Q   C   H  [350]

1145           1154           1163           1172           1181           1190
      TGC GAT GCT AAC TCA TGC ATT ATG AGT GAA GAA CTA AGA GAA CAA CTT TCC TTT
      --- --- --- --- --- --- --- --- --- --- --- --- --- --- --- --- --- ---
[351]  C   D   A   N   S   C   I   M   S   E   E   L   R   E   Q   L   S   F  [368]
```

FIG. 3C

```
            1199        1208        1217        1226        1235        1244
        GAG TTC AGC GAT TGT AGT CAG AAT CAA TAT CAG ACA TAT CTT ACT GAT CAT AAC
        --- --- --- --- --- --- --- --- --- --- --- --- --- --- --- --- --- ---
   [369]E   F   S   D   C   S   Q   N   Q   Y   Q   T   Y   L   T   D   H   N [386]

1253        1262        1271        1280        1289        1298
        CCA CAA TGC ATG CTC AAT GAA CCC TTG AGA ACA GAT ATT GTT TCA ACT CCA GTT
        --- --- --- --- --- --- --- --- --- --- --- --- --- --- --- --- --- ---
   [387]P   Q   C   M   N   E   P   L   R   T   D   I   V   S   T   P   V [404]

1307        1316        1325        1334        1343        1352
        TCT GGA AAT GAA CTT TTG GAG ACG GGA GAA GAA AGT GAC TTT GAC GCT CCT GCA
        --- --- --- --- --- --- --- --- --- --- --- --- --- --- --- --- --- ---
   [405]S   G   N   E   L   L   E   T   G   E   E   S   D   F   D   A   P   A [422]

1361        1370        1379        1388        1397        1406
        AAT CCG TGC TGC GAT GCT GCA ACA TGT AAA CTG ACA ACA GGG TCA CAG TGT GCA
        --- --- --- --- --- --- --- --- --- --- --- --- --- --- --- --- --- ---
   [423]N   P   C   C   D   A   A   T   C   K   L   T   T   G   S   Q   C   A [440]

1415        1424        1433        1442        1451        1460
        GAT GGA CTG TGT TGT GAC CAG TGC AAA TTT ATG AAA GAA GGA ACA GTA TGC CGG
        --- --- --- --- --- --- --- --- --- --- --- --- --- --- --- --- --- ---
   [441]D   G   L   C   C   D   Q   C   K   F   M   K   E   G   T   V   C   R [458]

1469        1478        1487        1496        1505        1514
        AGA GCA AGG GGT GAT GAC CTG GAT GAT TAC TGC AAT GGC ATA TCT GCT GGC TGT
        --- --- --- --- --- --- --- --- --- --- --- --- --- --- --- --- --- ---
   [459]R   A   R   G   D   D   L   D   D   Y   C   N   G   I   S   A   G   C [476]

1523        1532        1541        1550        1559        1568
        CCC AGA AAT CCC TTC CAT GCC TAA CCA ACA ATG GAG ATG GAA TGG TCT GCA GCA
        --- --- --- --- --- --- --- --- --- --- --- --- --- --- --- --- --- ---
   [477]P   R   N   P   F   H   A   * [483]

1577        1586        1595        1604        1613        1622
        ACA GGC AGT GTG TTG ATC TGA ATA CAG CCT AAT AAT CAA CCT CTG GCT TCT CTC 1631        1640        1649        1658        1667        1676
        AGA TTT GAT CAT GGA GAT CCT TCT TCC AGA AGG TTT CAC TTC CCT CAA ATC CAA 1685        1694        1703        1712        1721        1730
        AGA GAC CCA TCT GCC TGC ATC CTA CTA GTA AAT CAC CCT TAG CTT CCA GAT GGT 1739        1748        1757        1766        1775        1784
        ATC CAA ATT CTG TAA TAT TTC TTC TCC ATA TTT AAT CTA TTT ACC TTT TGC TGT 1793        1802        1811        1820        1829        1838
        AAC AAA ACC TTT TTC CTG TCA CAA AGC TCC ATG GGC ATG TAC AGC TTA TCT GCT 1847        1856        1865        1874        1883        1892
        GTC AAG AAA AAA AAT GGC CAT TTT ACC GTT TGC CAG TTA CAA AGC ACA TTT AAT 1901        1910        1919        1928        1937        1946
        GCA ACA AGT TCT TCC TTT TGA GCT GAT GTA TTC AAA GTC AAT GCT TCC TCT CCC
```

FIG. 3D

```
        1955        1964        1973        1982        1991        2000
AAA ATT TCA TGC TGG CTT CCC AAG ATG TAG CTG CTT CCG TCA ATA AAC AAA CTA 2009        2018        2027
TTC TCA TTC AAA AAA AAA AAC CCG AAT TC 3'
```

FIG. 4A

Proprotein domain:

```
              1         10        20        30        40        50
              *         *         *         *         *         *
CN         MIQVLLVTLCLAAFPYQGSSIILESGNVNDYEVLYPQKVTALPKGAVQPKY
Trigramin  MIQVLLITICLAVFPYQGSSIILESGNLNDYEVVYPEKVTALPKGAVQQKY
Cat        MIQVLLVTICLAAFPYQGSSIILESGNVNDYEVIYPRKVTALPKGAVQPKY
Jararhagin                                   ATRPKGAVQPKY
Ht-e       MIQVLLVTICLAAFPYQGSSIILESGNVNDYEVIYPRKVTALPKGAVQPKY 110       120       130       140       150
              *         *         *         *         *
CN         DHCYYHGRIQNDADSTASISACNGLKGHFKLQGETYLIEPLKLSDSEAHAV
Trigramin  DHCYYHGRIENDADSTASISACDGLKGHFKLQGEMYLIEPLELSDSEAHAV
Cat        DHCYYHGRIENDADSTASISACNGLKGHFKLQGEMYLIEPLKLPDSEAHAV
Jararhagin DHCYYHGRIENDADSTASISACNGLKGYFKLQRETYFIEPLKLPDSEAHAV
Ht-e       DHCYYHGRIENDADSTASISACNGLKGHFKLQGEMYLIEPLKLSDSEAHAV
```

Metalloproteinase domain:

```
              200       210       220       230       240
              *         *         *         *         *
CN         EQQGF.PQRYIELVVVADHRMFTKYNGNLNTIRIWVHELVNTMNVFYRPLN
Trigramin  EQQRF.PQRYIKLGIFVDHGMYTKYSGNSERITKRVHQMINNINMMCRALN
Cat        EHQKYNPFRFVELFLVVDKAMVTKNNGDLDKIKTRMYEIVNTVNEIYRYMY
Jararhagin EQQRYDPYKYIEFFVVVDQGTVTKNNGDLDKIKARMYELANIVNEIFRYLY
Ht-e       EHQ.....RYVELFIVVDHGMYTKYNGDSDKIRQRVHQMVNIMKESYTYMY 290       300       310       320       330       340
              *         *         *         *         *         *
CN         LTAIELDGETIGLANRGTMCDPKLSTGIVQDHSAINLWVAVTMAHEMGHNL
Trigramin  LTATIFNGNVIGRAPVGGMCDPKRSVAIVRDHNAIVFVVAVTMTHEMGHNL
Cat        LTAIDL.DRVIGLAYVGSMCHPKRSTGIIQDYSEINLVVAVIMAHEMGHNL
Jararhagin LTAIDFNGPTIGYAYIGSMCHPKRSVGIVQDYSPINLVVAVIMAHEMGHNL
Ht-e       LTSIAFDEQIIGRAYIGGICDPKRSTGVVQDHSEINLRVAVTMTHELGHNL
```

Disintegrin domain:

```
              420       430       440       450
              *         *         *         *
CN         ETGEESDF---DAOABOCCDAATCJKTTGSQCADGKCCDQCJFNJEGTVCR
Trigramin  EAGEDCDCGSPA...NPCCDAATCKLIPGAQCGEGLCCDQCSFIEEGTVCR
Cat        EVGEECDCGTPENCQNECCDAATCKLKSGSQCGHGDCCEQCKFSKSGTECR
Jararhagin EVGEECDCGTPENCQNECCDAATCKLKSGSQCGHGDCCEQCKFSKSGTECR
Ht-e       EAGIECDGGSLE...NPCCYATTCKMRPGSQCAEGLCCDQCRFMKKGTVCR
```

C-terminal domain:

```
              490       500       510       520       530
              *         *         *         *         *
Cat        NGQPCLDNYGYCYNGNCPIMYHQCYDLFGADVYEAEDSCFERNQKGNYYGY
Jararhagin NGQPCLDNYGYCYNGNCPIMYHQCYALFGADVYEAEDSCFKDNQKGNYYGY 590       600
              *         *
Cat        PGTKCADGKVCSNGHCVDVATAY*
Jararhagin PGTKCADGKVCSNGHCVDVATAY
```

FIG. 4B

```
              60         70         80         90        100
               *          *          *          *          *
     EDTMQYEFKVNGEPVVLHLEKNKGLFSKDYSETHYSSDGRKITTNPPVE
     EDAMQYEFKVNGEPVVLHLEKNKGLFSEDYSEIHYSPDGREITAYPSVE
     EDAMQYELKVNGEPVVLHLGKNKGLFSKDYSETHYSPDGREITTYPLVE
     EDAMQYEFKVNGEPVVLHLEKNKGLFSKDYSEIHYSPDGREITTYPPVE
     EDTMQYELKVNGEPVVLHLEKNKGLFSKDYSETHYSFDGRKITTNPSVE
             160        170        180        190
               *          *          *          *
        YKYENVEKEDEAPKMCGVTQTNWESDEPIKKASQLNLTP
        FKYENVEKEDEPPKMCGVTQ.NWESYESTKKASQLNVTP
        YKYENVEKEDEALKMCGVTQ.NWESYEPIKKASQLVVTA
        FKYENVEKEDEAPKMCGVTQ.NWKSYEPIKKASQLAFTA
        FKLKNVEKEDEAPKMCGVTQ.NWESYEPIKKASDLNLNP 250        260        270        280
               *          *          *          *
     IRVSLTDLEVWSDQDLINVQPAAADTLEAFGD.WRETVLLNRISHDNAQL
     IVTTLSVLEIWSEKDLITVQ.ASAPTTLTLFGAWRETVLLNRTSHDHAQL
     IHVALVGLEIWSNEDKITVKPEAGYTLNA.FGEWRKTDLLTRKKHDNAQL
     MHVALVGLEIWSNGDKITVKPDVDYTLNS.FAEWRKTDLLTRKKHDNAQL
     IDILLAGIEIWSNGDLINVQPASPNTLNS.FGEWRETDLLKRKSHDNAQL
             350        360        370        380        390        400        410
               *          *          *          *          *          *          *
     GISHDGNQCHCDANSCIMSEELREQLSFEFSDCSQNQYQTYLTDHNPQCMLNEPLRTDIVSTPVSGNELL
     GMHHDEDKCNCN..TCIMSKVLSRQPSKYFSECSKDYYQTFLTNHNPQCILNAPLRTDTVSTPVSGNELL
     GINHDSGYCSCGDYACIMRPEISPEPSTFFSNCSYFECWDFIMNHNPECILNEPLGTDIISPPVCGNELL
     GIHHDTGSCSCGDYPCIMGPTISNEPSKFFSNCSYIQCWDFIMNHNPECIINEPLGTDIISPPVCGNELL
     GIHHDTDSCSCGGYSCIMSPVISDEPSKYFSDCSYIQCWEFIMNQKPQCILKKPLRTDTVSTPVSGNELL 460        470        480
              *          *          *
          RARGD.DLDDYCNGISAGCPRNPFHA*
          IARGD.DLDDYCNGRSAGCPRNPFHA
          ASMSECDPAEHCTGQSSECPADVFHK
          ASMSECDPAEHCTGQSSECPADVFHK
          VSMVDRN.DDTCTGQSADCPRNGLYG*

540        550        560        570        580
              *          *          *          *          *
     CRKENGNKIPCAPEDVKCGRLYCKDNSPGQNNPCKMFYSNEDEHKGMVL
     CRKENGKKIPCAPEDVKCGRLYCKDNSPGQNNPCKMFYSNDDEHKGMVL
```

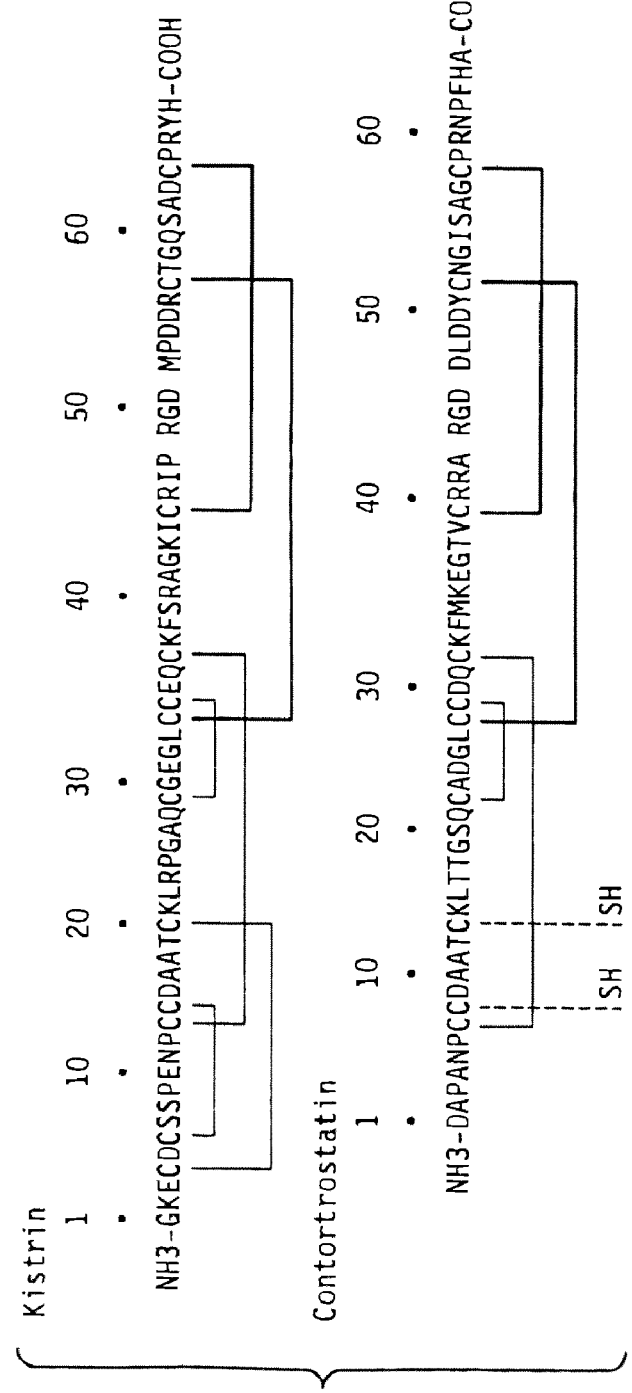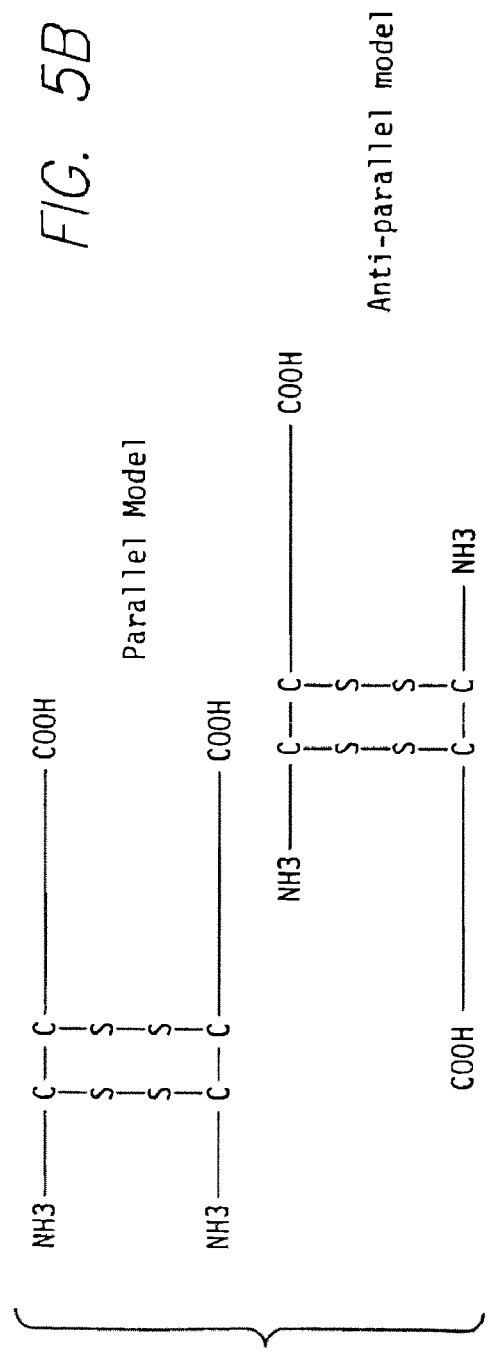
FIG. 5A
FIG. 5B

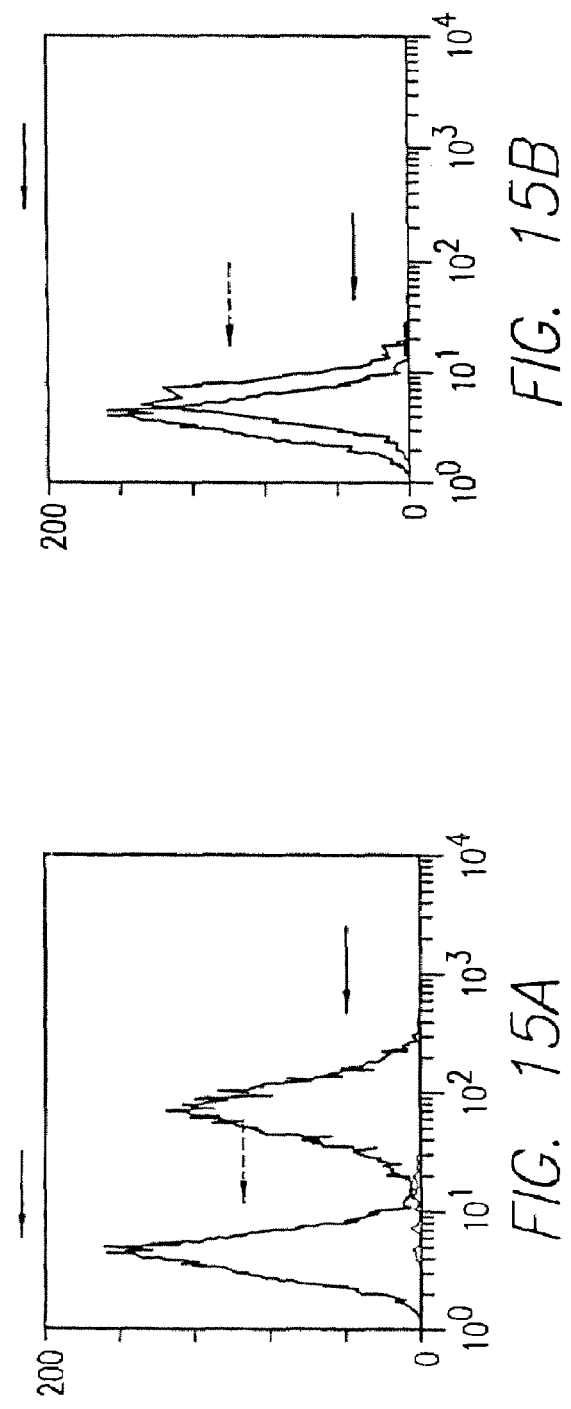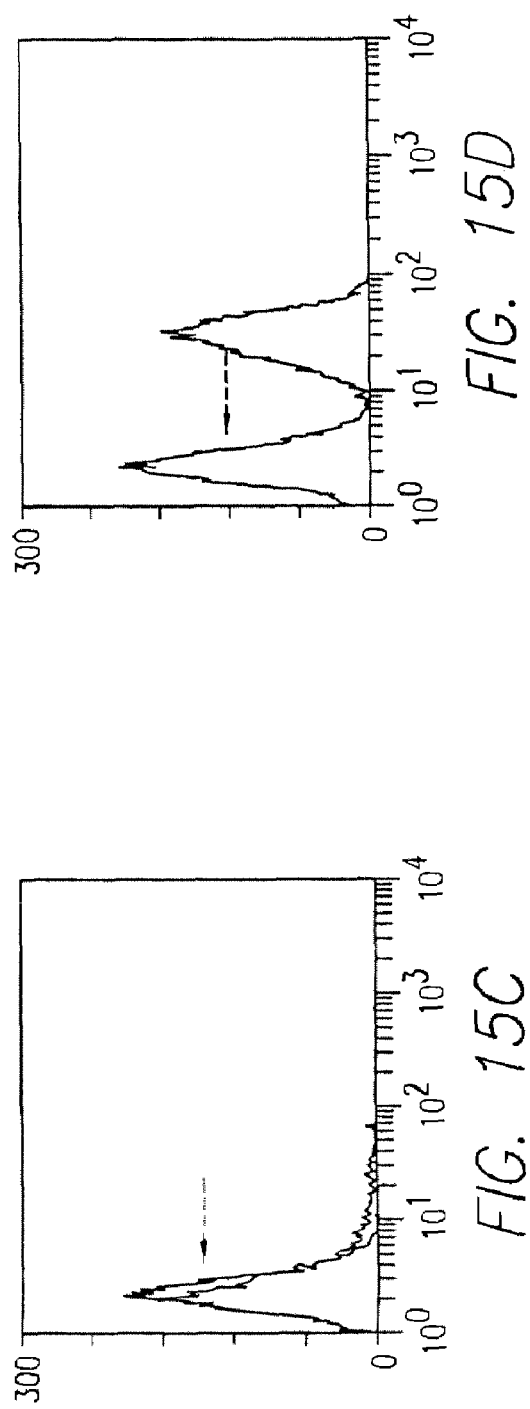

control    contortrostatin
phase contrast
F-actin
 
P-Tyr
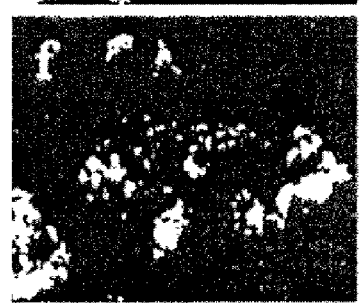
F-actin
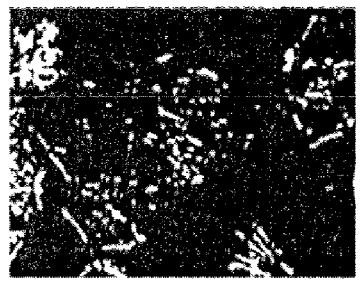
FAK
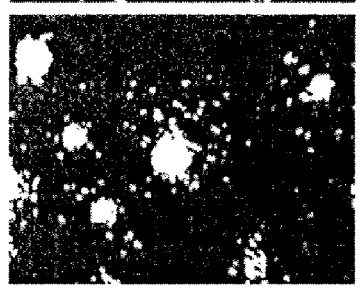
FIG. 25

CONTORTROSTATIN (CN) AND METHODS FOR ITS USE IN PREVENTING METASTASIS AND OTHER CONDITIONS

RELATED APPLICATIONS

This application is a divisional of U.S. Ser. No. 10/712,584, filed Nov. 12, 2003, now U.S. Pat. No. 7,220,724, which is a continuation of U.S. Ser. No. 09/591,552, filed Jun. 8, 2000, now abandoned which is a continuation-in-part of U.S. Ser. No. 09/460,295 filed Dec. 10, 1999, now U.S. Pat. No. 6,710,030, which is a continuation-in-part of U.S. Ser. No. 09/163,047, filed Sep. 29, 1998, now abandoned which is a continuation-in-part of U.S. Ser. No. 08/745,603, filed Nov. 8, 1996, which issued as U.S. Pat. No. 5,814,609 on Sep. 29, 1998, which is a continuation-in-part of U.S. Ser. No. 08/632,691, filed Apr. 15, 1996, which issued as U.S. Pat. No. 5,731,288 on Mar. 24, 1998, which is a division of application Ser. No. 08/540,423, filed Oct. 10, 1995, now abandoned, which is a continuation of application Ser. No. 08/141,321 filed Oct. 22, 1993, now abandoned, which are all incorporated herein by reference.

BACKGROUND OF THE INVENTION

Integrins on cancer cells play important roles in tumor invasion and spread. They are a family of proteins found on the cell surface of many cell types that mediate interactions between cells, and between cells and their surroundings. Integrins are heterodimers, composed of $\alpha$ and $\beta$ subunits involved in cell-cell and cell-substratum interactions. Integrins serve as receptors for extracellular matrix proteins such as fibronectin, fibrinogen, vitronectin, collagen and laminin. Some of these interactions have been shown to be mediated via an Arg-Gly-Asp (RGD) sequence present in the matrix proteins. Both the $\alpha$ and $\beta$ subunits are required for fibrinogen binding. For example, one of the members of the superfamily of integrin cell surface receptors is the platelet membrane glycoprotein (GP)IIb/IIIa which interacts with plasma fibrinogen in platelet aggregation.

CN binds to a specific integrin on the surface of blood platelets, and blocks the ability of platelets to adhere to one another (a process called platelet aggregation). Platelets are small fragments of bone marrow cells that are found in the blood stream. They have both beneficial and harmful activities. Their useful action is to stop bleeding following injury by facilitating the formation of a blood clot. But, under certain conditions they are involved in blocking arteries that supply nourishment to the heart—an action that can lead to a heart attack.

Integrin cell surface receptors have been investigated in the role of platelets in mediating coronary artery thrombosis and rethrombosis in the genesis of acute myocardial infarction [Zucker, M. B., *Sci. American* 242:86 (1990)]. For platelet aggregation an RGD sequence present in fibrinogen is essential for the interaction with (GP)IIb/IIIa [Ginsberg, M. H. et al., *Thrombos. Haemostas.* 59:1 (1988)]. Because of its inhibition of platelet aggregation, snake venom has been the subject of various investigations.

A number of proteins purified from venom of snakes of the Crotalidae and Viperidae families have been found to inhibit glycoprotein (GP)IIb/IIIa mediated platelet aggregation [see, e.g., Huang, T. F. et al., *J. Biol. Chem.* 262:16157 (1987); Gan, Z. R. et al., *J. Biol. Chem.* 263:19827 (1988); Yasuda, T. et al., *J. Am. Coll. Cardiol.* 16:714 (1990); Trikha, M. et al., *Fibrinolysis* 4 (Suppl. 1):105 (1990); Trikha, M. et al., *Blood* 76 (Suppl. 1):479a (1990); Holahan, M. A. et al., *Pharmacology* 42:340 (1991); Shebuski, R. J. et al., *Circulation* 82:169 (1990); Yasuda, T. et al., *Circulation* 83:1038 (1991)]. These proteins, classified as disintegrins, are typically disulfide rich. Moreover, all disintegrins isolated thus far, with the exception of barbourin [Scarborough, R. M. et al., *J. Biol. Chem.* 266: 9359 (1991)] contain an RGD (Arg-Gly-Asp) sequence that has been implicated as being involved in the inhibition of integrin-mediated interactions. In particular, the RGD sequence of the disintegrins may compete for fibrinogen binding sites on the platelet membrane, thereby inhibiting platelet aggregation induced by ADP or other agents.

Nonetheless, there appears to be increasing evidence that disintegrins may have unique surface geometry which facilitates interactions with integrins by mechanisms other than those based solely upon the RGD site. For example, the finding that a mutated, chemically synthesized derivative of echistatin (in which alanine was substituted for arginine in the RGD sequence) still possessed some biological activity, suggests that other regions in the protein may be involved in binding and that there may be some flexibility in the RGD binding site [Connolly, T. M. et al., *Circulation* 82 (Suppl. III):660 (1990)]. Synthetic RGD peptides, due to their small size, generally do not possess the molecular topography of the disintegrins and therefore cannot interact via the multiplicity of mechanisms likely to be involved in disintegrin binding.

One disintegrin of particular interest is CN, which has been isolated from the venom of *Agkistrodon contortrix contortrix* (the southern copperhead snake). The originally-reported purification procedure included molecular sieve chromatography on Sephadex G-100 SF, desalting on Sephadex G-25F and reverse phase HPLC. ADP-enhanced aggregation of stirred human platelet rich plasma and the inhibition thereof by CN were monitored at 37° C. It was found that preincubation for 1 minute of the platelet rich plasma ($3 \times 10^5/\text{mm}^3$) with 5 µl of the low molecular weight peak after Sephadex G-100 SF resulted in 76% inhibition of platelet aggregation induced by 10 µM ADP [Trikha et al. (1990), supra].

In a subsequent report it was noted that in crude venom, the inhibitor was not readily detectable due to the presence of platelet aggregating activity; however, following the first step of purification (hydrophobic interaction HPLC) inhibitory activity was separated from both aggregating activity and an α-chain degrading fibrinolytic enzyme present in the venom. Inhibitory activity was pooled following HPLC and applied to a hydroxylapatite HPLC column. In the final step of purification, $C_4$ reverse phase HPLC chromatography was employed. The yield of the homogeneous protein was 3-5 mg per gram of venom. CN was reported to have a molecular weight of 18-21 kDa under non-reducing conditions and 9 kDa under reducing conditions; thus, the molecule was believed to be a homodimer with the two subunits being held together by disulfide bond(s). Isoelectric focusing showed that the protein had an acidic pI. CN was reported not to exhibit fibrinolytic activity and was not a 5'-nucleotidase or a phospholipase based on molecular size and kinetics of inhibition of platelet aggregation. Following preincubation for 1 minute, CN at approximately 100 nM was reported to completely inhibit ADP-induced platelet aggregation [Trikha et al. (1990), supra].

It has further been reported that CN has 65 amino acids with five to six disulfide bridges, and that the sequence of CN appears to begin 10 amino acids downstream of applaggin (a platelet aggregation inhibitor from the venom of *Agkistrodon piscivorus piscivorus*). It was speculated that CN may have an insertion and/or a C-terminal extension of nine amino acids. It was further reported that a 50% inhibition ($IC_{50}$) of human platelet aggregation in platelet rich plasma was observed at 0.8 µg/ml of CN, and at 2.2 µg/ml with canine platelets [Trikha, M. et al., *Journal of Cellular Biochem.* 16F: 180 (1992)].

CN was reported to inhibit binding of human fibrosarcoma (HT-1080) and c-Ha-ras transfected rat embryo (4R) cells to fibronectin coated plates but not to matrigel coated plates. Inhibition of 4R cell binding to fibronectin in the presence of CN at 1 µg/ml and 5 µg/ml was 46% and 88%, respectively, and for HT1080 cells inhibition was 89% and 85%, respectively [Trikha, M. et al., *Proceedings of the American Association for Cancer Research* 33:34 (1992)].

Since it appears that CN can inhibit interactions between integrins and their receptors, the homodimeric disintegrin may prove useful in the management of diseases associated with these interactions. Consequently there exists a need for improved methods of making and using purified contortrostatin, substantially free other snake venom components.

SUMMARY OF THE INVENTION

The present invention fulfills the need for disintegrins, which can be used to inhibit biological processes such as platelet aggregation, cell growth, adhesion, metastasis, and neovascularization. In particular, homodimeric disintegrins, such as contortrostatin, are employed in methods and compositions, which modulate the adhesion, motility, and invasiveness of integrin expressing tumor cells. When formulated as a pharmaceutically acceptable composition, the proteins can be used to treat patients by inhibiting or disrupting disease processes associated with a ligand binding to an $\alpha v \beta 3$ or $\alpha v \beta 5$ integrin.

The present invention includes a method of decreasing the motility of an $\alpha v \beta 3$ integrin expressing cell comprising cross-linking at least two $\alpha v \beta 3$ integrins on the integrin expressing cells thereby inhibiting the motility of said cells. In one embodiment, the integrins are cross linked by a homodimeric disintegrin, preferably contortrostatin. The crosslinking disrupts FAK signaling and activates tyrosine phosphorylation of FAK and CAS. Moreover, the crosslinking induces an alteration in cell morphology, including changes in cytoskeletal or focal adhesion structures. In a most preferred embodiment the $\alpha v \beta 3$ integrin expressing cell is a tumor cell.

The present invention also includes a method of inhibiting the adhesion of integrin expressing cells to vitronectin by exposing the cells to contortrostatin. The contortrostatin inhibits adhesion by binding to integrin, in particular $\alpha v \beta 3$ or $\alpha v \beta 5$.

Another embodiment of the present invention is a homodimeric disintegrin comprising an amino acid sequence which is at least 90% percent identical to amino acid numbers 419 to 483 of SEQ ID NO: 2. The contortrostatin amino acid sequence is characterized by (i) binding to integrin $\alpha v \beta 5$ and (ii) inducing $\alpha v \beta 3$-mediated tyrosine phosphorylation of CAS and FAK in tumor cells. Preferably, the homodimeric disintegrin has an amino acid sequence at least 95% identical to amino acid numbers 419 to 483 of SEQ ID NO: 2, as determined by FASTA or BLAST using default opening and gap penalties and a default scoring matrix.

Yet another embodiment of the present invention is a pharmaceutically acceptable composition comprising a pharmaceutically acceptable carrier and a homodimeric disintegrin, such as contortrostatin.

The methods and compositions of the present invention can be used to inhibit platelet aggregation, tumor metastasis, angiogenesis, neovascularization, cell adhesion, invasiveness, or growth.

BRIEF DESCRIPTION OF THE DRAWINGS

The invention may be better understood with reference to the accompanying drawings, which include:

FIG. 1 illustrates the strategy for cloning contortrostatin cDNA, wherein FIG. 1A shows partial amino acid sequence of CN (CN) (amino acids 419 to 475 of SEQ ID NO:2) based on Edman Degradation Assay compared with other disintegrins, namely applaggin (SEQ ID NO:7), Trigramin (amino acids 480 to 551 of SEQ ID NO:8), albolabrin (SEQ ID NO:9), elegantin (SEQ ID NO:10), and kistrin (SEQ ID NO:10), illustrating common RGD sequences and highly conserved sequences, FIG. 1B shows the PCR primers, and FIG. 1C shows the principle of overlapping extension reaction used to generate the full-length cDNA of contortrostatin;

FIG. 3 shows the full-length nucleotide sequence of CN cDNA (SEQ ID NO:1) and the deduced amino acids (SEQ ID NO:2), including an 86 nucleotide 5N-end non-translatable region (NTR), an open reading frame between nucleotides 87 and 1535, a termination codon at nucleotides 1536 to 1538, and a 3N-NTR, which includes an AATAAA site and ends with a poly-A tail;

FIG. 4 shows the multi-domain structure of contortrostatin precursor (SEQ ID NO:2), compared with trigramin precursor (SEQ ID NO:8) and other snake venom hemorrhagic proteins Cat (SEQ ID NO:12), Jararhagin (SEQ ID NO:13) and Ht-E (SEQ ID NO:14);

FIG. 5 illustrates the formation of a contortrostatin homodimer, wherein FIG. 5A shows the amino acid sequence and disulfide bond pattern of the disintegrin kistrin (SEQ ID NO:10) compared to contortrostatin (amino acids 419 to 483 of SEQ ID NO:2), which has a 6-amino-acid truncation at the N-terminus, including two half cystine residues resulting in two cysteine residues being unpaired, and FIG. 5B shows the unpaired cysteines may participate in the formation of two intermolecular disulfide bonds to form a unique homodimeric structure, wherein the two monomers may be linked in a parallel or anti-parallel pattern;

FIG. 15. Expression patterns of integrins αvβ3 and αvβ5 in T24 and T24-β3 neg. cell lines. This figure shows the binding of antibodies, 7E3 (anti-αvβ3) and P1F6 (anti-αvβ5), to the cells. Binding of the antibodies was detected with a secondary antibody conjugated to FITC using flow cytometry. The background peak in each assay is labeled by the dashed arrow. The peaks represents the cells treated with specific antibodies are labeled with the solid arrows. 7E3 (10 μg/ml) binds to T24 cells and causes a right-shift of the peak (A), P1F6 (10 μg/ml) also binds to the cells and causes a slight right-shift (B), suggesting that T24 expresses both αvβ3 (major) and αvβ5 (minor). On T24-β3 neg. cells, no 7E3 binding is found, as shown by the overlapping peaks (C). However, P1F6 binds to the cells (D), indicating that the cells express only αvβ5. Data shown here is representative of three identical experiments.

FIG. 25. Contortrostatin causes changes in cell morphology, collapse of actin stress fibers and disassembly of focal adhesions in T24 cells adhering to Matrigel. Phase contrast microscopy of cells treated for 30 min with 0.5 μM contortrostatin (b) shows an altered morphology and decreased cell spreading compared to control cells (a). F-actin staining of control cells (c and g) shows large stress fibers while actin in contortrostatin- treated cells (d and h) appears to have collapsed into amorphous aggregates. Phosphotyrosine staining shows numerous well-defined focal adhesion structures (e). In contrast, focal adhesions are almost entirely absent in cells treated with contortrostatin (f). Specific staining for FAK in control cells (i) yielded a pattern similar to that observed for phosphotyrosine while FAK staining in contortrostatin-treated cells (j) was diffuse and lacked punctate appearance.

DETAILED DESCRIPTION OF THE INVENTION

Characterization, Cloning and Expression of CN

Figure 1:
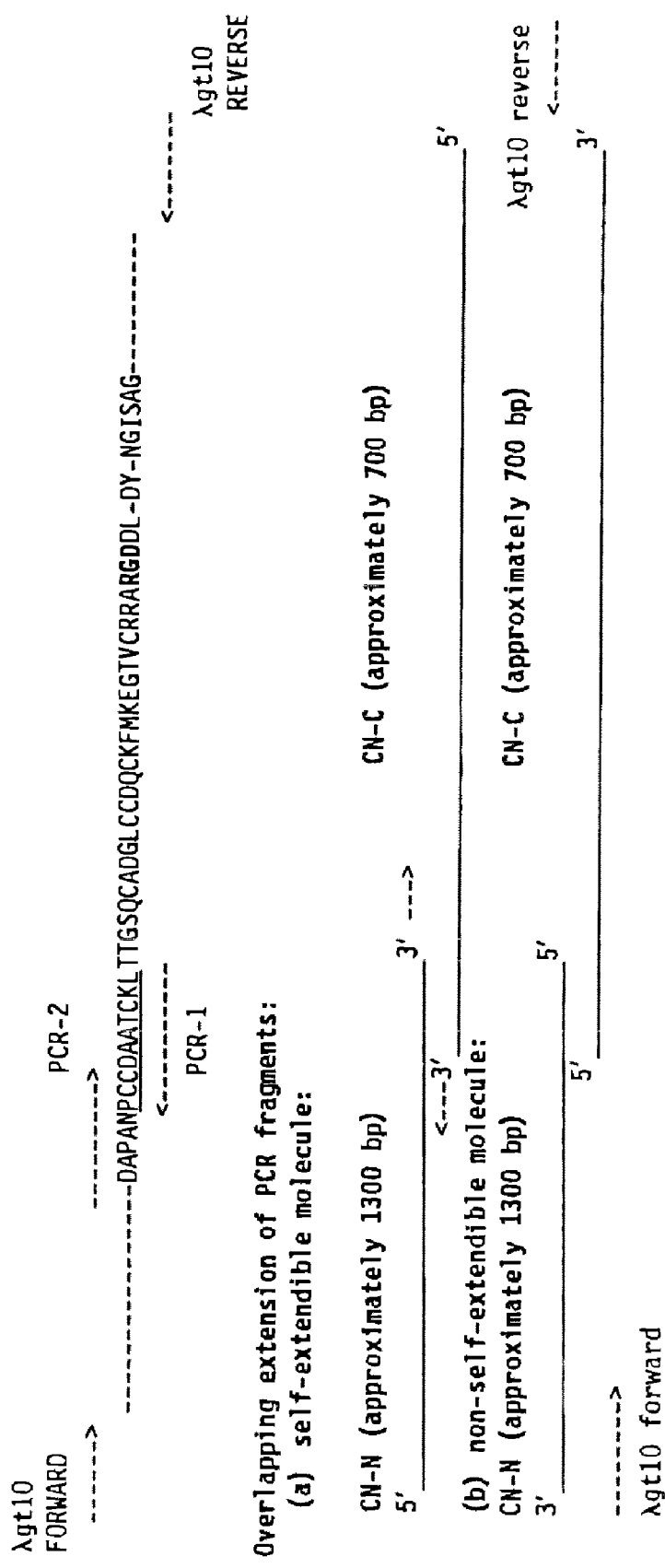

We have purified and characterized a disintegrin: contortrostatin (CN) from *A. c. contortrix* venom. CN is a homodimer with a mass of 13,505 for the intact protein and 6,956 for the reduced and pyridylethylated protein. To test binding affinity to platelet (GP)IIb/IIIa (fibrinogen receptor), competition of CN with [$^{125}$I]7E3, an antibody directed to (GP)IIb/IIIA, was analyzed using human platelet rich plasma (PRP). CN displayed an $IC_{50}$ of 25 nM. Thus, CN is a potent β3 integrin antagonist.

In further embodiments, we provide the protein contortrostatin from southern copperhead snake venom that possesses potent anti-tumor activity. A sophisticated technique has been developed to purify this protein from the complex mixture of proteins found in southern copperhead venom. As indicated above, originally CN was characterized as an inhibitor of platelet aggregation. We have purified several disintegrins from snake venoms. Contortrostatin (CN) was purified from southern copperhead venom. Disintegrins contain a constrained Arg-Gly-Asp (RGD) sequence at the tip of a flexible peptide loop, of about 13 amino acid residues flanked by Cys residues, protruding from the main protein core. See, e.g. amino acid residues 457 to 469 of SEQ ID NO: 1 or 2. This exposed RGD sequence enables disintegrins to bind to integrins with high affinity.

The cDNA of CN has been amplified from a library of *A.c. contortrix* venom gland cells, constructed in λgt10. Amino acid composition and partial amino acid sequences of CN have been determined by Edman degradation; see FIG. 1. Using this information a full-length cDNA of 2,027 nucleotides (SEQ ID NO: 1), which encodes a contortrostatin precursor protein, has been cloned and sequenced.

As a member of disintegrin super family, CN shares high similarity with other disintegrins including, trigramin whose nucleotide sequences were known. FIG. 1A shows a partial amino acid sequence of CN based on Edman degradation assay. The partial sequence is also compared with other disintegrins as indicated. The RGD sequence is bold-faced. The highly conserved PCCDAATCKL sequences on which PCR primers are designed are underlined. FIGS. 1A and 1B show how the cDNA of CN has been cloned by means of PCR using primers based on the highly homologous sequences among the disintegrin family as well as known λgt10 sequences flanking the cDNA inserts. The PCR primer pairs are: SEQ ID NO:5 (λgt10 forward primer) and SEQ ID NO:3 (PCR-1) 5'-GATTTACAGGTTGCAGCATCGC-3', which is anti-sense of trigramin cDNA encoding part of the underlined conserved sequence (FIG. 1A and 1B). SEQ ID NO:4 (PCR-2), which is complementary to PCR-1, and SEQ ID NO:6 (λgt 10 reverse primer). SEQ ID Nos. 5 and 3 amplify DNA coding for amino acids upstream to the underlined part. SEQ ID Nos. 4 and 6 amplify those coding for the downstream part of CN. Full length cDNA has been obtained by overlapping extension of the two pieces of PCR products (see FIGS. 1C and 2).

The cDNA sequence and deduced amino acid sequence of contortrostatin precursor are shown in FIG. 3. The full length sequence is composed of 2,029 nucleotides (SEQ ID NO:1). It is composed of an 86 nucleotide non-translatable region at the 5' end, an open reading frame coding for 483 amino acids (SEQ ID NO:2), and a 3' non-coding region.

FIG. 4 shows the multidomain structure of contortrostatin (SEQ ID NO:2) compared to that of four other snake venom hemorrhagic proteins: trigramin (SEQ ID NO:8); Cat (catrocollastatin from *Crotalus atrox* venom) (SEQ ID NO:12); jararhagin (from *Bothrops jararaca* venom) (SEQ ID NO:13); and Ht-e (from *C. Atrox* venom) (SEQ ID NO:14). According to the structural division of snake venom metalloproteinases, the precursor of contortrostatin can be divided into a pro-protein (amino acid residues 1 to 190 of SEQ ID NO: 1 or 2), metalloproteinase (residues 191 to 410 of SEQ ID NO: 1 or 2) and disintegrin (residues 419 to 483 of SEQ ID NO: 1 or 2) domains. The mature monomer of native disintegrin starts at D419, i.e., the aspartic acid residue at position 419. Underlined portions of FIG. 4 show the RGD sequences of both contortrostatin and trigramin, as well as the conserved HEMGHNLGIHH sequences (e.g., amino acids 334 to 344 of SEQ ID NO:8) of the zinc-binding motifs in the metalloproteinase domains of each molecule.

According to the present invention, therefore, there is also provided a protein consisting essentially of purified contortrostatin or purified contortrostatin variants retaining the properties of a disintegrin, or a precursor of contortrostatin having pro-protein, metalloproteinase, and disintegrin domains. This protein can be purified from natural sources such as snake venom or can be made by recombinant techniques as will be understood by those skilled in the art with reference to the disclosure herein.

Still further, the present application claims both the native and synthetic amino acid and nucleotide sequences. Unless otherwise modified, the term "protein" as used herein encompasses both native and synthetic polypeptides and peptides. Synthetic protein includes recombinant and chemically synthesized protein. Unless otherwise indicated, the term "contortrostatin" include both the native and synthetic versions of the proteins.

The term "nucleotide sequence" includes both the DNA and RNA sequences. For example, the nucleotide sequence for a contortrostatin protein ("contortrostatin nucleotide sequence") includes the gene ("contortrostatin gene") encoding the native and precursor protein, its complementary DNA, and the RNA corresponding to the foregoing; also included are messenger RNA encoding for the contortrostatin protein, its complementary RNA, and the DNA corresponding to the foregoing. Further, as used in this application the nucleotide sequences include: (1) the DNA sequences encoding the contortrostatin proteins, (2) the nucleotide sequences (which may be RNA or DNA) complementary to the foregoing sequences, (3) the corresponding RNA sequences to the DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methyl-cytosine replacing cytosine, and (5) nucleotide sequences that are for example, at least 90% identical, or more preferably at least 95% identical, as determined by FASTA or BLAST using default opening and gap penalties and a default scoring matrix.

Since nucleotide codons are redundant, also within the scope of this invention are equivalent nucleotide sequences which include: nucleotide sequences which code for or can be translated into the contortrostatin proteins, their protein variants, functional equivalents, or derivatives. These nucleotide sequences may also be used in the practice of the invention.

In addition to the above, contortrostatin nucleotide sequences also include: (1) nucleotide sequences that are capable of hybridizing to the coding sequences of the respective nucleotide sequences, under stringent hybridization conditions, and (2) fragments of or mutagenized nucleotide sequences of those disclosed herein which can encode or can be translated into proteins having substantially the same biological characteristics/activities of the respective contortrostatin proteins, e.g. integrin antagonist, zinc-binding, proteinase, anti-angiogenic factor, and further activities as disclosed herein in further embodiments and examples.

The terms "contortrostatin proteins", as used in relation to proteins include the respective proteins described in the Example section, below, and precursor proteins obtainable by the methods of the present invention, most preferably proteins exhibiting the properties of a disintegrin obtainable from the isolation methods of the Example section below. As will be appreciated by those of skill in the art, the contortrostatin proteins may be subject to allelic variations. Accordingly contortrostatin proteins include: (1) protein variants of these proteins; e.g. these protein variants may contain amino acid sequences that are, for example, at least 90% identical, or more preferably at least 95% identical to the pro-protein, metalloproteinase, disintegrin and/or native contortrostatin regions of the protein; (2) the functional equivalents of these proteins and their variants, respectively; and (3) the derivatives, including fragments, of the contortrostatin proteins and their variants, respectively. The percent identity of the amino acid sequences of contortrostatin proteins are as determined by FASTA or BLAST using default opening and gap penalties and a default scoring matrix (available at the National Center for Biotechnology Information website; http:\\www.ncbi.nlm.nih.gov\).

The variants can result from, e.g. substitution, insertion, or deletion of the amino acid sequences of the contortrostatin proteins. The derivatives of the proteins and their variants, include fragments of these proteins and immunorective peptides that specifically bind with antibody to contortrostatin.

Two amino acid sequences are functionally equivalent if they have substantially the same biological activities such as the ability to bind to integrin receptors. The proteins may be fused to other proteins, for example, signal sequence fusions may be employed in order to more expeditiously direct the secretion of recombinant contortrostatin proteins.

Substitutional variants of the proteins disclosed herein are those in which at least one residue in the disclosed sequences has been removed and a different residue inserted in its place. Preferably, the amino acid change is conservative. Thus, modifications of the contortrostatin proteins' primary amino acid sequences also include conservative variations. The term "conservative variation" as used herein denotes the replacement of an amino acid residue by another, biologically similar residue. Examples of conservative variations include the substitution of one hydrophobic residue such as isoleucine, valin, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that the polypeptide retains its biological activity, e.g., antibodies raised to the substituted polypeptide also immunoreact with the unsubstituted polypeptide.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of contortrostatin proteins. They include variants completely lacking in glycosylation (unglycosylated) and variants having at least one less glycosylated site than the native form (deglycosylated) as well as variants in which the glycosylation has been changed.

As illustrated in the examples, native CN may be isolated from the venom of *Agkistrodon contortrix contortrix* in a relatively straightforward manner. Alternatively, CN may also be prepared by exploiting a variety of biochemical methods in current use, such as recombinant DNA technology or the like. Moreover, the sequence information reported herein can be used for making probes to identify variants, fragments, conserved domains or pro-proteins having substantial homology to CN and its precursor(s). Once identified, the genes may be isolated, further manipulated, and cloned into expression vectors.

There is also provided a vector containing a DNA molecule encoding a contortrostatin protein made according to techniques understood by those with skill in the art with reference to the disclosure herein. In the present invention, the contortrostatin nucleotide sequence may be inserted into a recombinant expression vector. The term "recombinant expression vector" refers to a plasmid, virus or other vehicle known in the art that has been manipulated by insertion or incorporation of a contortrostatin genetic sequence. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. These vectors may be used to transform competent hosts to produce transformants that are capable of producing the snake venom protein.

Further, there is provided, a prokaryotic or eukaryotic host cell stably transformed or transfected by the vector, as well as a method of making the contortrostatin protein or its biological variants. The method includes the steps of, first culturing a prokaryotic or eukaryotic host cell transformed with DNA encoding for contortrostatin protein; and then, recovering the contortrostatin protein. The host cell can be mammalian cells, plant cells, insect cells, yeast and other fungi, or bacteria.

Further, the sequence encoding the native protein may then be manipulated (for example, by single or multiple mutations or deletions) in a manner well known in the art to provide modified proteins, in which changes of one or more amino acids have been introduced. Following the procedures described herein, the determination of whether a particular polypeptide exhibits an activity profile characteristic of CN would then be a matter of routine experimentation. Accordingly, the present invention contemplates both the native CN and mutations thereof which exhibit the characteristic activity profile defined herein. Moreover, CN may also be employed in the form of a fusion protein with a suitable thrombolytic agent. Fusion proteins of this type may be prepared in a manner analogous to that described for formation of platelet aggregation inhibitor/anti-thrombin polypeptide fusion proteins in the aforementioned U.S. Pat. Nos. 5,182,260 and 5,196,403 to Maraganore et al.

Despite the high sequence homology with other disintegrins (shown in FIG. 1A) [Niewiarowski, S., et al., *Seminars in Hematology.* 31:289-300 (1994)], contortrostatin displays a unique amino-terminal sequence with a truncation of about 8 amino acids. In comparison with other disintegrins, two cysteine residues are missing at the amino-terminus of contortrostatin. It is well established that monomeric disintegrins possess an even number of cysteines, all of which are involved in disulfide bond formation. The missing two cysteines in the contortrostatin precursor may lead to disruption of disulfide bond pairing. This in turn may lead to the formation of two intermolecular disulfide bonds between two identical chains to form the homodimeric structure of contortrostatin. FIG. 5 presents a hypothetical model of the structure of the dimeric disintegrin as compared to a disintegrin, kistrin, whose disulfide bond positioning is known [Adler, M., et al., *Biochemistry* 32:282-9 (1993)]. In FIG. 5A, the sequences of the two disintegrins are compared. It can be readily seen that kistrin, with 12 half-cystines, forms 6 disulfide bonds. By comparison, contortrostatin, which has two unpartnered cysteine residues, can form the homodimeric structures presented in FIG. 5B. We are not sure at present which alignment is preferred, but we are confident, based on mass spectral analysis and SDS-PAGE of native and reduced contortrostatin, that a homodimeric structure most probably identical to one of the two shown, is formed.

CN is clearly quite different from applaggin, as the latter has been demonstrated unmistakably to be a monomer [Wencel-Drake et al. (1993), supra]. Moreover, CN does not inhibit platelet release reactions, as has been demonstrated to be the case with applaggin in the aforementioned U.S. Pat. Nos. 5,182,260 and 5,196,403 to Maraganore et al. Finally, despite the similarities in sequence there are also significant differences between the sequences with respect to both the start site and the ensuing sequences.

Methods of Use

Homodimeric disintegrins, such as contortrostatin, are employed in methods and compositions of the present invention to modulate the adhesion, motility, and invasiveness of integrin expressing tumor cells. When formulated as a pharmaceutically acceptable composition, the proteins can be used to treat patients by inhibiting or disrupting disease processes associated with a ligand binding to an $\alpha v\beta 3$ or $\alpha v\beta 5$ integrin.

The present invention includes a method of decreasing the motility of an $\alpha v\beta 3$ integrin expressing cell comprising cross-linking at least two $\alpha v\beta 3$ integrins on the integrin expressing cells thereby inhibiting the motility of said cells. In one embodiment, the integrins are cross linked by a homodimeric disintegrin, preferably contortrostatin. The crosslinking disrupts FAK signaling and activates tyrosine phosphorylation of FAK and CAS. Moreover, the crosslinking induces an alteration in cell morphology, including changes of cytoskeletal or focal adhesion structures. In a most preferred embodiment the $\alpha v\beta 3$ integrin expressing cell is a tumor cell.

The present invention also includes a method of inhibiting the adhesion of integrin expressing cells to vitronectin by exposing the cells to contortrostatin. The contortrostatin inhibits adhesion by binding to an integrin, in particular $\alpha v\beta 3$ or $\alpha v\beta 5$.

CN has been found to be a potent inhibitor of human, rabbit and canine platelet aggregation in vitro. Unlike applaggin, however, CN does not inhibit platelet release reactions. Platelets comprise a plurality of different granules, including alpha granules and dense granules, whose contents are released when the platelets aggregate. The finding that CN does not inhibit platelet release of granule contents (including ATP from the dense granules) signifies that the platelets may still release their contents (and thus maintain some semblance of normal physiological activity) notwithstanding the inhibition of aggregation. By contrast, when applaggin inhibits platelet aggregation it also inhibits platelet release (as measured by, e.g., inhibition of serotonin release from the dense granules). Thus, normal platelet physiological processes are necessarily further perturbed with administration of applaggin.

Several lines of evidence indicate that CN inhibits platelet aggregation by binding specifically to the (GP)IIb/IIIa integrin receptor. For example, in a fibrinogen-(GP)IIb/IIIa ELISA [Dennis, M. S. et al., *Proc. Natl. Acad. Sci.* (*USA*) 87 :2471 (1990)], in which the extent of purified (GP)IIb/IIIa bound to immobilized fibrinogen can be quantitated, CN effectively blocks (GP)IIb/IIIa binding. Additionally, the partial amino acid sequence of CN indicates considerable similarity with other disintegrins known to bind to (GP)IIb/IIIa. Finally, CN blocks 7E3 binding to (GP)IIb/IIIa. 7E3 is a murine monoclonal antibody that specifically binds to (GP) IIb/IIIa, thereby inhibiting human and canine platelet aggregation [Coller, B. S. et al., *J. Clin. Invest.* 72:325 (1983)]. In the presence of a low concentration of CN, 7E3 binding to platelets is significantly inhibited.

Three snake venom disintegrins, kistrin [Yasuda et al. (1990), supra], echistatin [Holahan et al. (1991), supra] and bitistatin [Shebuski, R. J. et al. (1990), supra], have demonstrated a potential role as antithrombotic agents for use in thrombolytic therapy by enhancing and sustaining arterial thrombolysis in conjunction with recombinant tissue plasminogen activator. Based on the low $IC_{50}$ values of CN, its in vivo efficacy as an antithrombotic agent has been examined. Using a canine reoccluding carotid arterial thrombosis model, CN has been found to efficiently sustain opening of the carotid artery in conjunction with anisoylated plasminogen streptokinase activator complex (APSAC). APSAC alone was found insufficient to prevent the rapid reocclusion of the carotid artery. Heparin was not needed to sustain opening when CN was administered with APSAC. This is a significant distinction over other disintegrins (e.g., echistatin, bitistatin and kistrin) which have been evaluated in models of coronary artery thrombosis [Cousins, G. R. et al., *FASEB J.* 9:A938 (1995)].

The compositions of the present invention are particularly useful for treatment of thrombotic diseases in mammals, alone or in conjunction with one or more thrombolytic agents. In particular, the compositions of the present invention have utility in treating or preventing arterial, venous and microvascular thrombosis and thromboembolism. Thus, the compositions have utility in treating stroke, transient ischemic attacks, arteriosclerosis, atherosclerosis, pulmonary embolism, aneurisms and angina. In particular, the compositions have utility in preventing or treating myocardial infarctions.

The compositions of the present invention also have utility in inhibiting metastasis in melanoma, carcinoma and sarcoma patients. CN has been observed to bind to at least two sites on human melanoma M24met cells: a high affinity site with a dissociation constant (Kd) of 1.1 (±0.7) nM and 96,000 (±39,000) sites per cell; and a lower affinity site with a Kd of 41 (±13) nM and 480,000 (±90,000) sites per cell. Moreover, CN has been found to inhibit human melanoma M24met cell adhesion to fibronectin and vitronectin, and to a lesser extent to collagen and laminin Thus, methods and compositions for preventing metastases in melanoma, carcinoma and sarcoma patients are also contemplated as within the scope of the present invention.

In accordance with the present invention, the unique properties of disintegrins are exploited in methods and compositions for preventing metastasis in carcinoma, sarcoma and melanoma patients. In particular embodiments the positions and methods are provided for preventing metastasis in breast cancer patients.

We have developed a metastatic breast cancer model by implanting human breast cancer cells into the mammary fat pads of mice. The mice we use were genetically manipulated so that their immune system is deficient and they are unable to reject the implanted human cancer cells. We observed that palpable tumor masses developed in the mammary fat pads two weeks after cancer cell implantation, and that tumor cells spread to the lungs in untreated animals within 12 weeks. CN or placebo was injected daily into tumors in several different groups of mice. Following treatment we found that the size of the tumor masses in the CN treated mice were significantly smaller than those in placebo-treated mice. Significantly, the CN-treated group showed >90% inhibition of tumor spread to other sites in the body (metastasis), as compared to the placebo group. Our studies indicate that CN blocks the attachment of breast cancer cells to proteins which are essential components of blood vessel walls. CN also inhibited new blood vessel formation (neovascularization) induced by breast cancer cells following incubation on a chick embryo membranous respiratory organ called the chorioallantoic membrane while placebo treatment did not. Since neovascularization is critical to continued proliferation of a growing tumor the ability to inhibit the growth of new vessels is an important anti-cancer action of CN.

Based on these studies it appears that disintegrins such as the snake venom protein contortrostatin possess anti-metastatic activity. Our findings suggest that CN blocks several critical steps in metastasis and is, therefore, more potent than other agents which only block a single step.

The disintegrin-containing compositions of the present invention are also useful in treatment of osteoporosis. Osteoclasts are multinucleated cells up to 400 µm in diameter which resorb mineralized tissue in vertebrates. Bone resorption appears to proceed by a combination of processes involving attachment to bone, polarized secretion of acid and proteases, and active motility of osteoclasts along the bone substrate; osteoclasts bind to bone via an RGD-sequence as an obligatory step in bone resorption, and this RGD-binding integrin is at adhesion structures [Sato, M. et al., *J. Cell Biol.* 111:1713 (1990)]. The molecular mechanisms whereby osteoclasts attach to bone are not well understood; however, by analogy to other cells, members of the integrin superfamily of divalent cation-dependent adhesion molecules are believed to mediate this interaction. Disintegrins, such as echistatin [Sato et al. (1990), supra] and presumably CN, inhibit bone resorption by isolated osteoclasts; the mechanism of action is presumably by disrupting adhesion structures. Accordingly, compositions and methods for treatment of osteoporosis employing an amount of CN effective to inhibit bone resorption by osteoclasts are also contemplated as within the scope of the present invention [Mercer, B. et al., *J. Bone Mineral Res.* 13:409-414 (1998)].

Finally, CN has utility in the promotion of wound healing. Events involved in wound healing are known to include alterations in integrin expression or functional activity and suggest that integrin receptor modulation plays a central role in wound repair and inflammation. Fibronectin is also known to play a number of roles in the wound healing process. Although fibronectin function is thought to be critical to effective wound healing, there are reports that at least one of its activities (the binding of bacteria) may be counterproductive [Grinnell, F., *J. Cell. Biochem.* 26:107 (1984); Clark, R. A. F., *Arch. Dermatol.* 124:201 (1988)]; the presence of fibronectin in the wound bed may thus promote bacterial attachment and infection. Fibronectin also appears to be intimately involved in keloid formation. Keloids are a pathological consequence of wound healing that affects a significant proportion of non-Caucasian patients. Keloids are benign tumors of connective tissue that grow beyond the boundary of the original wound and are rich in fibronectin and type I collagen [Sible, J. C. & Oliver, N., *J. Cell Biochem. Suppl.* 16F:170 (1992)]. By virtue of their inhibition of cell-cell and cell-extracellular matrix interactions (including interaction with fibronectin), disintegrins such as CN would be expected to have a profound effect on processes involved in wound repair, including keloid formation.

A major problem following obstetrical and gynecological surgery is the formation of adhesions. This widespread phenomenon observed in peritoneal wound repair is a leading cause of pain, intestinal obstruction and infertility. Adhesion formation appears to involve an imbalance in the fibrinolytic and fibroproliferative inflammatory responses and may also involve a modulation of the cell-cell or cell-extracellular matrix interactions. There is strong evidence for an important role of fibrin during the initial stages of adhesion formation [diZerega, G. S., *Prog. Clin. Biol. Res.* 381:1 (1993)]. The presence of cellular elements, including platelets, further exacerbates the role of fibrin. In view of the role of platelets and fibrin in adhesion formation, the use of disintegrins such as CN as a potential therapeutic agent is most attractive.

In preliminary studies in a rabbit model of adhesion formation, abrasion and devascularization of the uterine horns of rabbits were employed to induce adhesion formation during wound healing in untreated animals [Rodgers, K. et al., *Int. J. Fertil.* 35:40 (1990)]. Alzet pumps were employed to continuously deliver CN at a rate of 10 µl/hr (36 µg/ml). In this model system, decreased adhesion formation was observed in treated animals compared to controls. Therefore, compositions and methods for preventing adhesion formation whereby an amount of CN effective to prevent adhesion formation is administered to a patient in need of such treatment are also contemplated as within the scope of the present invention.

The compositions of the present invention comprise at a minimum an amount of CN effective to achieve the desired effect (i.e., prevent thrombus formation, prevent metastasis in carcinoma patients, prevent adhesion formation, etc.) and a suitable carrier or excipient. Generally, in these compositions, CN is present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day. Such compositions have particular utility in the prevention of thrombus formation.

Alternatively, CN is administered in combination with at least one thrombolytic agent present in an amount effective to achieve thrombolysis. Suitable thrombolytic agents include, but are not limited to, the following: anisoylated plasminogen streptokinase activator complex (APSAC); tissue-type plasminogen activator (tPA); urokinase-type plasminogen activator (uPA); and fibrolase, a snake venom fibrinolytic agent as described in U.S. Pat. No. 4,610,879 to Markland, Jr. et al.

CN may be administered by a variety of heretofore known means suitable for delivery thereof into the blood stream in substantial amounts. Intravenous administration of CN in a suitable liquid vehicle or excipient is presently contemplated as the preferred route of administration. CN is soluble in water, and may therefore be effectively administered in a suitable aqueous solution (e.g., phosphate buffered saline). Alternatively, CN may be administered orally (in the form of tablets or capsules formulated with a suitable binder or excipient material, or in the form of aqueous or oily suspensions, solutions, emulsions, syrups or elixirs) or as a parenteral suspension. As is well known in the art, adjuvants such as local anesthetics, preservatives, buffering agents, lubricants, wetting agents, colorants, flavorings, fillers and diluents may suitably be included in any of these formulations.

EXAMPLES

These additional embodiments may be better understood with reference to the accompanying examples, which are intended for purposes of illustration only and should not in any sense be construed as limiting the scope of the invention as defined in the claims appended hereto.

In conducting the following examples, lyophilized venom from *Agkistrodon contortrix contortrix* was obtained from Biotoxins, Inc., St. Cloud, Fla. All chemicals were of the highest grade available. Pierce protein assay kit using bicinchoninic acid was employed to determine protein concentrations [Smith, P. K. et al., *Anal. Biochem.* 150:76 (1985)].

For hydrophobic interaction (HIC)-HPLC a Perkin Elmer 410 LC pump was employed with a LC-95 UV/VIS detector. For reverse phase HPLC a Spectra Physics LC 8810 pump was employed with an SP 8450 UV/VIS detector. Absorbance for HIC-HPLC was monitored at 280 nm and for RP-HPLC at 215 nm. A polypropyl aspartamide (250×21 mm) column (Poly LC, Columbia, Md.) was used for hydrophobic interaction HPLC. C18 (218TP54 and 218TP510) columns were used for reverse phase (RP) HPLC (Vydac, Hesperia, Calif.). For cation exchange chromatography a CM (carboxymethyl) 300 column (SynChrom, Inc., Lafayette, Ind.) was employed.

Example 1

Purification and Characterization of CN

CN was purified from *Agkistrodon contortrix contortrix* (Southern copperhead) venom using a four step HPLC procedure. For the first step of purification crude venom (1 g) was dissolved in 0.1 M phosphate buffer containing 1 M ammonium sulphate, pH 6.8 (buffer A) and applied to the polypropyl aspartamide HIC-HPLC column. Elution was achieved as follows: 50 minutes isocratically with 100% buffer A; a linear gradient for 90 minutes to 0.1 M phosphate, pH 6.8 (buffer B); 40 minutes isocratic at 100% buffer B. Fractions of 10 ml were collected in a Pharmacia Frac 100 fraction collector at 4° C. using a flow rate of 5 ml/min. Fractions containing platelet aggregation inhibiting activity were pooled and concentrated by ultra-filtration using an Amicon stir cell with a YM3 membrane. Proteins were detected at 280 nm; platelet aggregation inhibiting activity was observed in the flow through.

Further purification was achieved by C18 RP-HPLC. Fractions containing platelet aggregation inhibiting activity were pooled and concentrated for this second step. The C18 column (218TP510) was equilibrated with 95% of 0.1% TFA in water (solvent A) and 5% of 80% acetonitrile in 0.1% TFA in water (solvent B). Elution was achieved as follows: isocratic at 95% solvent A and 5% solvent B for 10 minutes; a linear gradient to 40% solvent B in 65 minutes; linear gradient to 100% solvent B in 20 minutes; isocratic at 100% solvent B for 25 minutes. Fractions were collected manually every minute at a flow rate of 7 ml/minute. CN eluted at 28% acetonitrile (66 minutes).

Fractions containing platelet aggregation inhibiting activity were pooled and rerun on the same C18 RP-HPLC column using a shallower gradient. Elution was achieved as follows: isocratic at 80% solvent A and 20% solvent B for 20 minutes; a linear gradient to 30% solvent B over 90 minutes; and a 25 minute linear gradient to 100% solvent B. CN eluted as a sharp peak at 22% acetonitrile (82 minutes). The minor peak eluting just before CN also contained platelet aggregation inhibiting activity and had a similar molecular weight to that of CN; due to the low yield, this peak was not further characterized.

A final purification step was performed using pooled fractions from the previous step. These pooled fractions were applied to a cation exchange, CM300, HPLC column and elution was achieved by an increasing gradient of sodium chloride. CN elutes at 52.5 minutes (160 mM NaCl). This step achieved a separation of CN from isoforms thereof. Yields of 1-2 mg of the four-step purified CN were obtained per gram of crude venom.

For SDS-polyacrylamide gel electrophoresis (SDS-PAGE) Tris-Tricine 16.5% gel was used according to published protocols under reducing and non-reducing conditions [Schagger, H. & Von Jagow, G., *Anal. Biochem.* 166:368 (1987)]. The gel was run using a BioRad minigel system and stained with silver [Morrisey, J. H., *Anal. Biochem.* 117:307 (1981)] or Coomassie blue R250.

SDS-PAGE analysis of CN revealed that it has a molecular mass of approximately 15,000 Daltons under non-reducing conditions and 5,000-7,000 Daltons under reducing conditions. This strongly suggests that CN is composed of two subunits. Another possibility, albeit unlikely, is that the large difference in migration may be attributed to differential uptake of SDS under non-reducing and reducing conditions.

The molecular weight of CN was confirmed by mass spectrometry using a triple quadrupole instrument with an electrospray ion source. A mass of 13,507 Daltons was determined for intact CN; the analysis also indicated a high degree of purity. Mass spectrometry of the reduced and pyridylethylated protein gave a mass of 7,996 Daltons. This is the expected value for the individual chains of a homodimer of this molecular weight, taking into account the incorporation of 1,248 mass units for the 12 pyridylethyl groups incorporated into the 6 reduced disulfide bounds (based on homology with known disintegrins, there should be 6 disulfide bonds). These findings place CN in a unique position among all the disintegrins reported to date in that it exists as a dimer. Scatchard analysis of CN binding to unactivated human platelets revealed a single class of binding sites with a dissociation constant ($K_d$) of 37 nM and number of binding sites ($B_m$) equal to 100,000. Reduction of the disulfide bonds completely eliminated platelet aggregation inhibitory activity, even at concentrations ten times the $IC_{50}$, suggesting that structural parameters are critical for maintaining activity.

Example 2 cDNA Cloning of Contortrostatin Using Polymerase Chain Reaction

Partial amino acid sequence analysis of contortrostatin using Edman degradation methods suggested that the subunit of contortrostatin is homologous with other disintegrins (FIG. 1A) with the cysteine residues aligned, as well as the RGD sequences [Niewiarowski, S. et al., *Seminars in Hematology* 31: 289-300 (1994)]. The strategy for cloning contortrostatin cDNA with PCR is based on the structural homology among the disintegrin family. Design of the PCR primers is schematically illustrated in FIG. 1. The underlined sequences in FIG. 1A are highly conserved among disintegrin family. PCR primers were synthesized based on this region. The nucleotide sequence coding this region in the cDNA of trigramin from *Trimeresurus gramineus* was used to synthesize the primers PCR-1 and PCR-2 (FIG. 1B). PCR-1 and PCR-2 are complimentary primers corresponding to the coding sequence of a consensus sequence PCCDAATCKL (e.g., amino acids 424 to 433 of SEQ ID NO:2) among disintegrins. Their nucleotide sequences are:

```
                                        (SEQ ID NO: 3)
PCR-1:  5'-GTTTACAGGTTGCAGCATCGC-3'

(SEQ ID NO: 4)
PCR-2:  5'-GCGATGCTGCAACCTGTAAAC-3'
```

λgt10 forward and reverse primers which flanks the EcoRI site of the vector were used for PCR. Nucleotide sequences of the primers are listed below:

```
λgt10 forward primer:
                                        (SEQ ID NO: 5)
5'-AGCAAGTTCAGCCTGGTTAAG-3'

λgt10 reverse primer:
                                        (SEQ ID NO: 6)
5'-CTTATGAGTATTTCTTCCAGGGTA-3'
```

Oligonucleotide primers were synthesized by the Microchemical Core Facility of the University of Southern California Comprehensive Cancer Center. Primers were provided in a deprotected lyophilized form, and were resuspended and diluted to the appropriate concentration with water prior to use.

Example 3

PCR Amplification of Contortrostatin cDNA

We used the cDNA library of *Agkistrodon contortrix contortrix* venom gland constructed in λgt 10 vector at the EcoRI site. The estimated titer of the library was $10^{10}$ plaque-forming units (pfu)/ml and the complexity was 50,000. 500 µl of the cDNA library phage solution was mixed with 500 µl of 20% polyethylene glycol (PEG)/1M NaCl solution in an Eppendorf tube. The Eppendorf tube was inverted twice and incubated at room temperature for 30 min. The solution was then centrifuged at 14,000 rpm for 10 min. The supernatant was discarded and the pellet was resuspended in 100 µl of sterile water. The suspension was incubated with 10 µl of proteinase K (10 mg/ml) at 50° C. for 1 hr. The phage particle suspension was extracted with phenol/chloroform twice and the DNA was precipitated with 1/10 volume of 3M sodium acetate and 2 volumes of absolute ethanol followed by washing with 80% ethanol. DNA was resuspended in 10 µl of sterile water in preparation for PCR.

Figure 2:
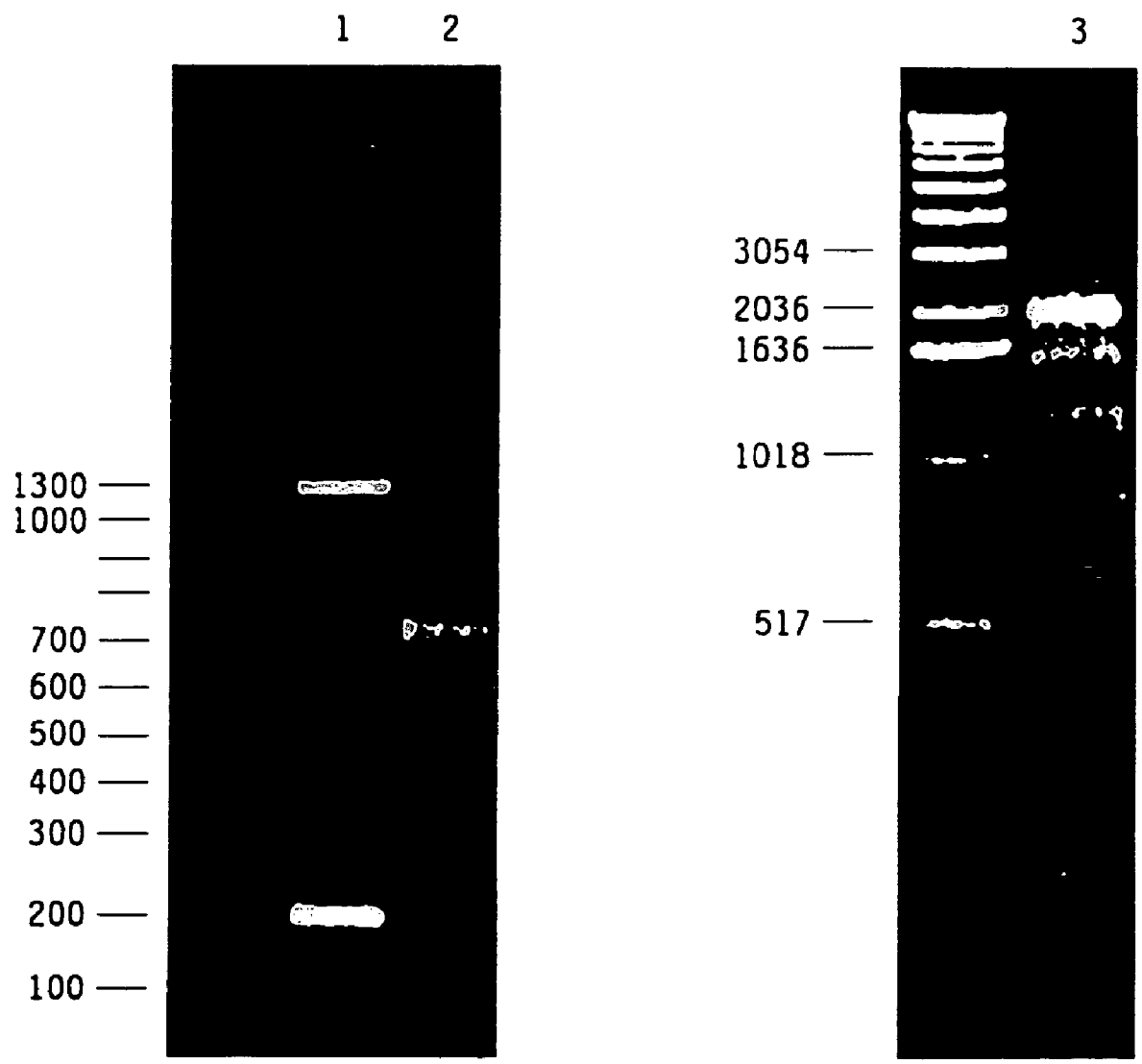
FIG. 2 shows electrophoresis of the PCR products, wherein a major band of about 1,300 bp was amplified with PCR primed by λgt10 forward and PCR-2 (lane 1), a band of approximately 700 bp resulted from PCR primed by PCR-2 and λgt10 reverse (lane 2), and the overlapping product of the two fragments is shown in lane 3, with a molecular size of about 2,000 bp.

The PCR reaction was set up as follows: 5 µl of DNA solution was mixed with 1 µl of 25 mM dNTP's (Pharmacia), 1 µl (100 ng/µl) each of forward and reverse PCR primers, and 5 µl of 10× PCR buffer. The final volume of the reaction was brought up to 50 µl with water. After mixing, one drop of mineral oil was applied on top of the liquid. The Eppendorf tubes were pre-heated to 98° C. for 5 min, then incubated at 70° C. and 60° C. for 1 min respectively before cooled down to room temperature. 2.5 units of Taq DNA polymerase (Pharmacia) was added to each mix. The thermal cycler was programmed as follows: 96° C. for 15 sec, 55° C. for 30 sec, 72° C. for 1 min. PCR amplification was performed for 30 cycles. Following the last cycle, a final 72° C. extension step for 7 min was allowed before the samples were cooled down to 30° C. The PCR product was extracted with chloroform before it was analyzed by agarose gel electrophoresis. The bands resolved by electrophoresis were recovered from the agarose gel using Geneclean kit (Bio 101, Inc.) according to the manufacturer's manual for direct DNA sequencing.

λgt10 forward and PCR-1 primers were used to amplify the up stream region of the adhesion site (FIG. 1B). Similarly, PCR-2 and λgt10 reverse primers were coupled to amplify the down stream part of the cDNA (FIG. 1B). A major band of about 1300 bp (designated CN-N) was obtained with the first pair of primers (FIG. 2, lane 1), and a major band of approximately 700 bp (designated CN-C) resulted from PCR using the later pair of primers (FIG. 2, lane 2). CN-N and CN-C were subjected to nucleotide sequencing analysis prior to the overlapping extension. As expected, CN-N demonstrated high similarity to cDNA of trigramin which encodes its N-terminal signal peptide. CN-C nucleotide deduced amino acid sequence was very similar to the disintegrin COOH-terminal sequence encoding the RGD site.

Since PCR-1 and PCR-2 were complimentary, CN-N and CN-C overlap at this site, and therefore, can be assembled into a full length cDNA. To accomplish this goal, we used an overlapping extension method as shown in FIG. 1C. Briefly, equal molar amount of double-strand PCR products CN-N and CN-C were mixed with λgt10 forward and reverse primers. After denaturation of both double-strands, the subsequent reannealing results in two kinds of molecules. One is annealed CN-N and CN-C at the adhesion site with the recessive ends as 3'-ends. This molecule can be automatically elongated into full length double-strands using PCR. The other molecule is similarly annealed, but with the recessive ends as 5'-ends. Although these molecules are not self-elongated, the recessive parts can be filled in with priming by λgt10 primers at each end. FIG. 2, lane 3 shows the products of overlapping extension as resolved by agarose gel electrophoresis. The size of the major band is estimated to be 2,000 bp which equals the sum of CN-N and CN-C, and is thus designated "full length". The full length band was recovered from the gel and treated with EcoRI. Subsequently, this piece of DNA was subcloned into the plasmid vector pcDNA3.1(+).

Example 4

Subcloning of PCR Product into Plasmid Vector

Plasmid pcDNA3.1(+) was digested with EcoRI (Pharmacia) followed by dephosphorylation using T4 phosphatase (Boehringer-Mannheim). PCR overlapping extension product was also digested with EcoRI. The PCR product was inserted into the linearized vector by ligation reaction using T4 ligase (Pharmacia) at 16° C. overnight. All the reactions were set up and performed according to standard protocols. Successful ligation was selected by plating transformed E. coli (DH5α) on ampicillin containing plates. Plasmids containing the insert were amplified in E. coli. Purified plasmid DNA was obtained with Qiagene DNA Miniprep columns.

Example 5 cDNA Sequencing

Automated DNA sequencing was performed by the Microchemical Core Facility. PCR primers were used as sequencing primers for direct sequencing of PCR products. For sequence analysis of the insert in plasmid pcDNA3.1(+), T7 promoter primer and BGH reverse primer, which flanks the multiple cloning sequence (MCS), was utilized to initiate the assay. Typical reactions gave readable sequences of 400 to 600 bp. The sequencing reactions were performed on double-stranded DNA in the case of plasmid DNA. With the synthesis of new sequencing primers, additional sequences were obtained, and these were assembled into overlapping contiguous sequences using DNAsis computer program.

FIG. 3 shows the full length nucleotide sequence inserted between the EcoRI sites. It is composed of 2,029 nucleotides, which is the size of the full length band of the overlapping extension (FIG. 2, lane 3). Following an 86-nucleotides 5N-end non-translated region (5N-NTR), an open reading frame is found between nucleotides number 87 and 1535. Nucleotide 1536 to 1538 is the termination codon. The 3N-NRT possesses an AATAAA site in the 3N-end noncoding region, and ends with poly(A) tail, suggesting that the cDNA we obtained with the overlapping extension was indeed a complete cDNA (FIG. 3). The open reading frame encodes 483 amino acids (SEQ ID NO:2). The structure of cDNA deduced amino acid sequence can be divided into three domains. The first 190 amino acids of SEQ ID NO:2, starts with methionine, are highly similar to the pro-protein of many cloned snake venom proteins (comparison is shown in FIG. 4). From amino acid 191 to 418 of SEQ ID NO:2 is the metalloproteinase domain including a Zinc-binding motif HEMGHNLGISH (aa 334 to 344 of SEQ ID NO:2). The remaining 65 amino acids of SEQ ID NO:2 belong to contortrostatin monomer which is identical to the known partial amino acid sequence of contortrostatin determined by Edman methodology. This sequence is very similar to those of many disintegrins whose sequences have been determined (FIG. 4 and 1A). The calculated molecular weight of the disintegrin is 6.77 kDa, which is equal to that of CN monomer. The RGD (aa 461 to 463) sequence is in bold face letters. The three-domain structure matches the precursor model of snake venom metalloproteinase and disintegrin proposed by Kini et al. [*Toxicon* 30:265-296, (1992)]. There is evidence that disintegrins are synthesized in the snake venom gland cells as a multi-domain precursor which undergo post-translational proteolysis and folding to generate a mature disintegrin.

Example 6

CN Effects on Mammary Carcinoma Adhesion & Invasion

Figure 6:
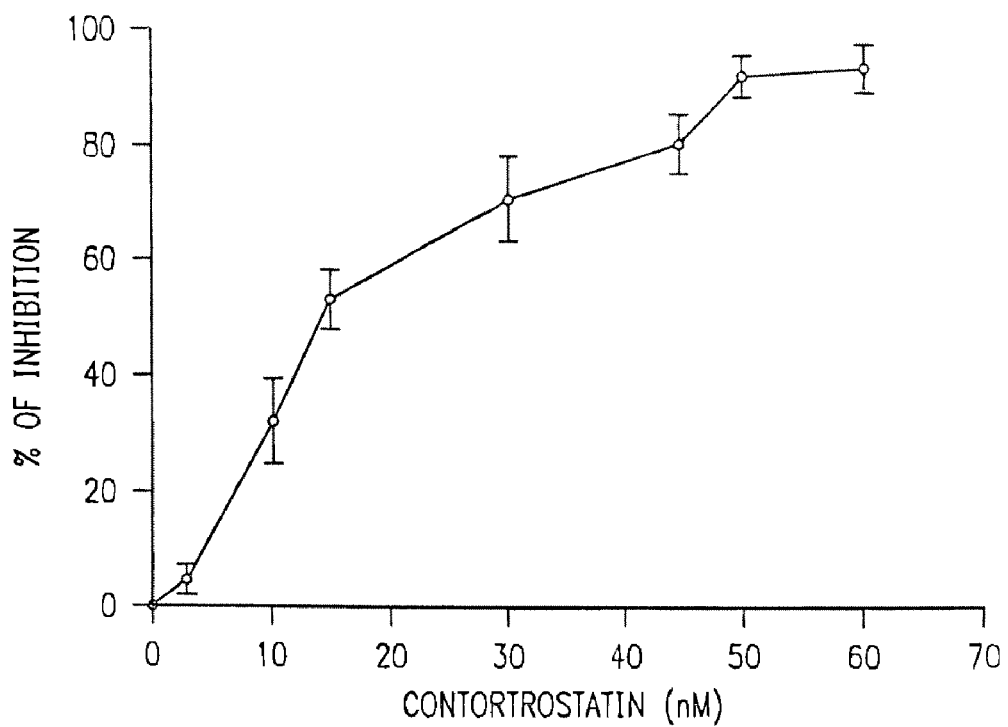
FIG. 6 shows CN inhibited adhesion of MDA-MB-435 to fibronectin.
Figure 7:
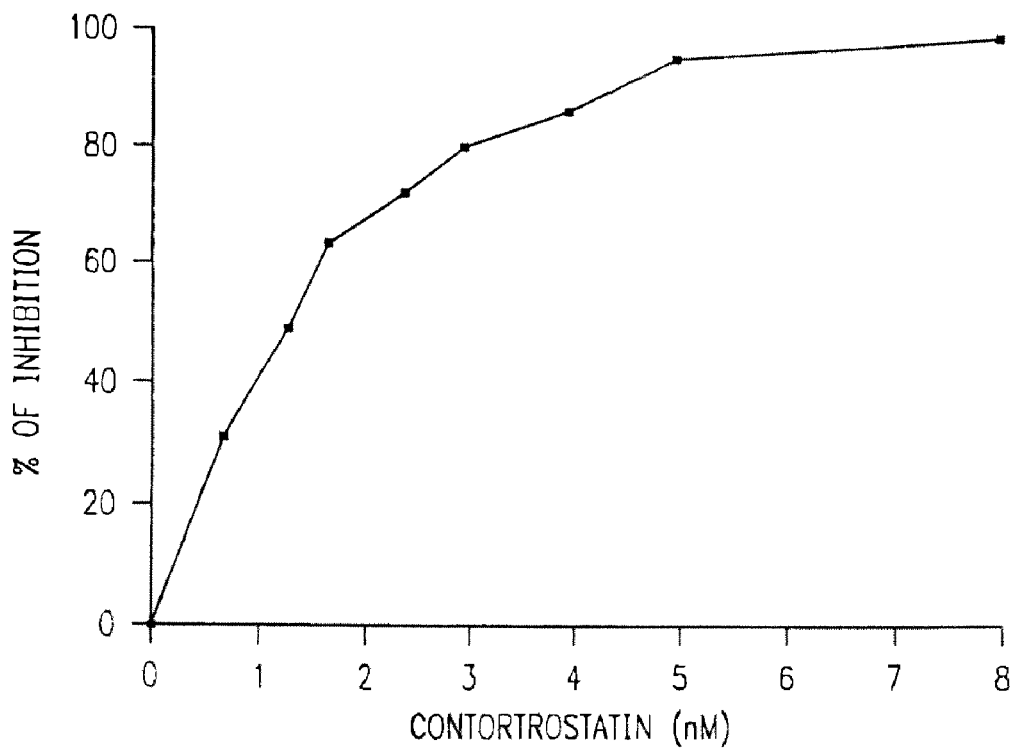
FIG. 7 shows CN inhibited adhesion of MDA-MB-435 to vitronectin.

The effect of CN on binding of highly metastatic human breast cancer cells, MDA-MB-435 cell line, to ECM proteins was examined. Human fibronectin and vitronectin were immobilized in the wells of 96-well microtiter plates. Referring to FIGS. 3 and 4, CN inhibited adhesion of MDA-MB-435 to both ECM proteins in a dose dependent manner. $IC_{50}$ for adhesion to fibronectin is 18 nM (FIG. 6) and for vitronectin the $IC_{50}$ is 1.5 nM (FIG. 7). CN had minimal effect on the weak adhesion seen by MDA-MB-435 cells to human type I collagen, or to rat type I collagen to which the MDA cells have a relatively strong affinity.

Figure 8:
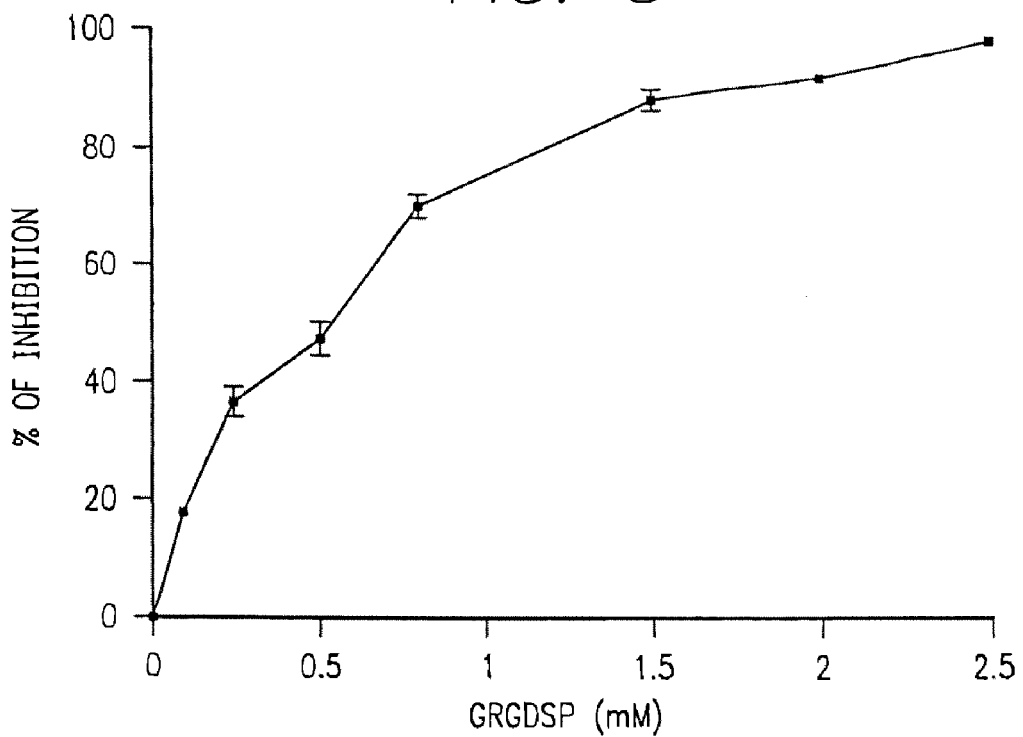
FIG. 8 shows the inhibition of binding of human mammary carcinoma cells to immobilized CN with GRG-DSP (SEQ ID NO:15)
Figure 9:
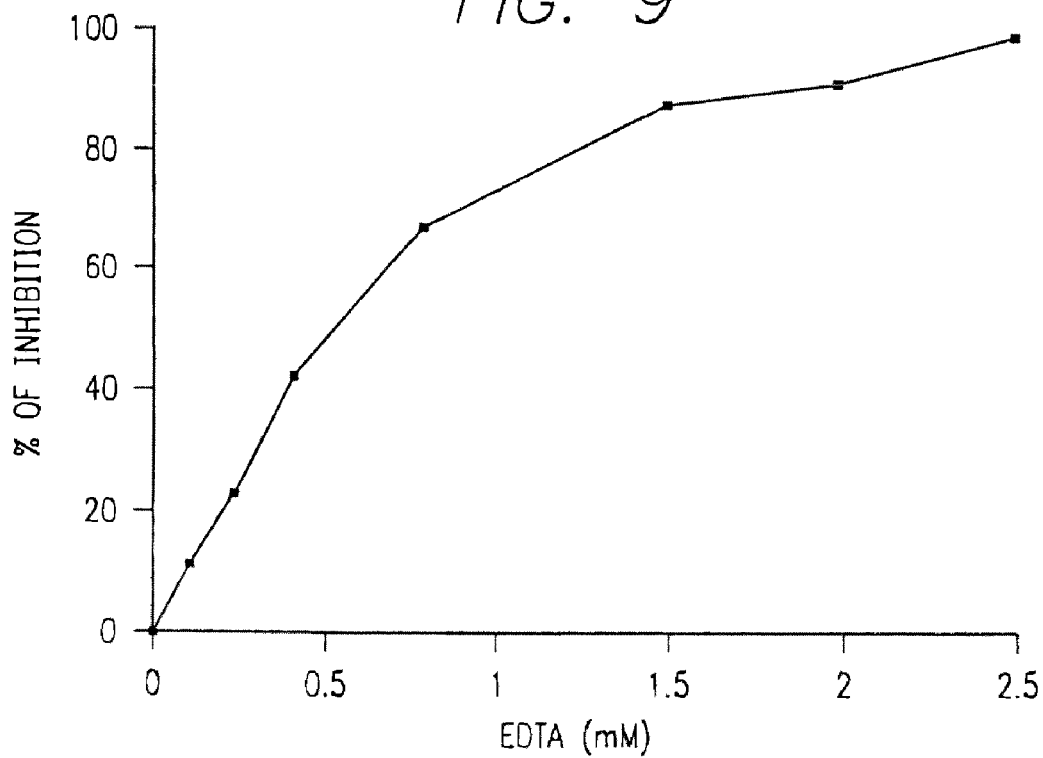
FIG. 9 shows the inhibition of binding of human mammary carcinoma cells to immobilized CN with EDTA.

In a variation of the above experiments, CN was immobilized. It was found that CN can support binding of MDA-MB-435 cells in a dose dependent manner. Binding of MDA-MB-435 cells to immobilized CN is blocked by an RGD peptide, GRGDSP (SEQ ID NO:15) ($IC_{50}$=0.4 mM), and by EDTA ($IC_{50}$=0.8 mM). Since integrin receptors require metal ions for non covalent association of their subunits, our findings indicate that CN binds to integrin receptors on the surface of MDA-MR-435 cells via an RGD-mediated mechanism. The finding that immobilized CN can support adhesion of MDA-MB-435 cells suggests that this binding involves cell surface receptors on the tumor cells. Referring to FIGS. 8 and 9, varying concentrations of GRGDSP (FIG. 8) or EDTA (FIG. 9) were used to inhibit binding of human mammary carcinoma cells to immobilized CN. CN was at 0.1 μg/well. The vertical line at each data point indicates the y-axis error bar. All experiments were conducted as three sets of triplicates for each data point. Since adhesion of MDA-MB-435 cells to immobilized CN is completely blocked by GRGDSP and by EDTA (FIGS. 8 and 9), CN binds solely to integrin receptors of MDA-MB-435 cells via an RGD—dependent mechanism.

Example 7

Contortrostatin is a More Potent Inhibitor of Tumor Cell Motility than Monomeric Disintegrins.

Figure 10:
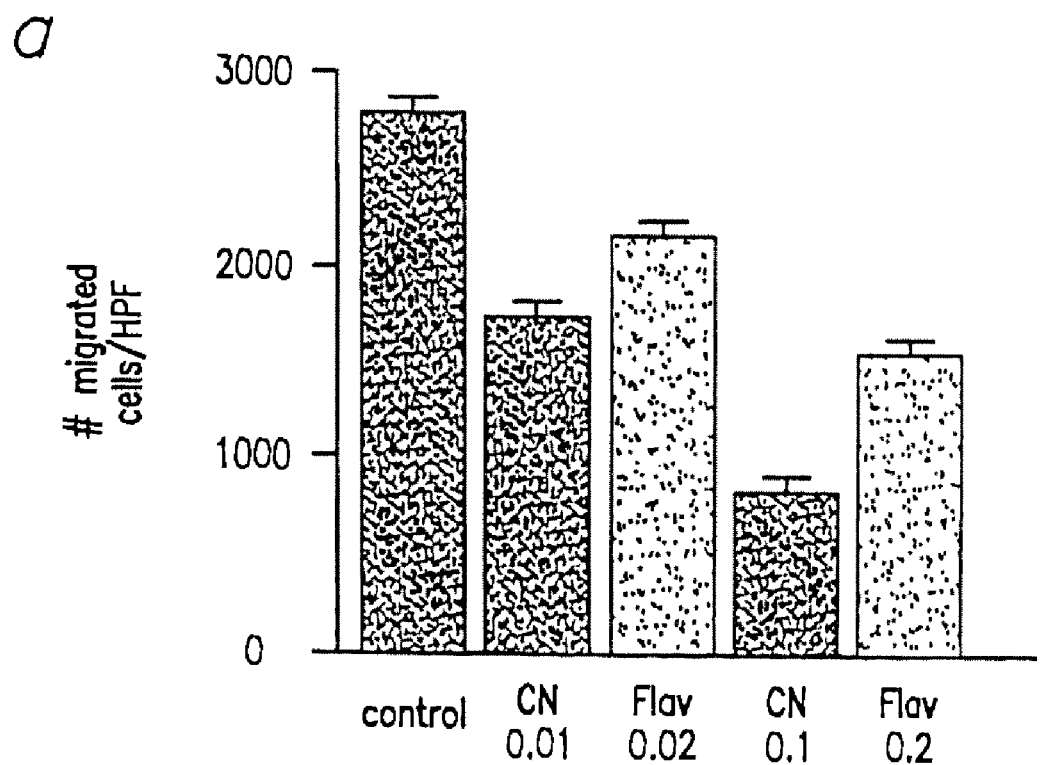
FIG. 10 shows the inhibition of motility by contortrostatin and a monomeric disintegrin. (a) The homodimeric disintegrin contortrostatin (CN) at the indicated µM concentrations inhibits motility of MDA-MB-435 cells on Matrigel, and does so more effectively than the monomeric disintegrin, flavoridin (Flav), even when the monomer is used at twice the concentration of contortrostatin. Data shown represents mean values. Error bars represent SEM. (b) Images of stained cells migrated to the bottom side of the Matrigel-coated membrane. These experiments were performed four times to confirm results.

To test the hypothesis that integrin blockage will inhibit motility of tumor cells, a Boyden chamber assay was used to determine the effect of disintegrins on cell migration. Tumor cell motility was quantitated using a modified Boyden chamber (Repesh, L. A. A New in vitro Assay for Quantitating Tumor Cell Invasion, *Invasion and Metastasis.* 9: 192-208, 1989). Transwell chambers with 12 µm pore size (Corning Costar, Cambridge, Mass.) were coated with Matrigel diluted 1:100 with serum-free medium. Treated or untreated MDA-MB-435 cells were added to the upper chamber, and the lower chamber was filled with HT1080 conditioned medium. Cells were incubated at 37° C. for 10 h and after removal of non-migrating cells, cells migrating to the bottom side of the coated membrane were fixed, stained and quantitated using digital image analysis (NIH Image). It was observed that contortrostatin inhibited cell migration under these conditions by 70% at a concentration of 0.1 µM (FIGS. 10a and b). In comparison, the monomeric disintegrin flavoridin, at twice the concentration (0.2 µM) inhibited migration by only 45%. Thus, contortrostatin appears to possess additional inhibitory activity not present in the monomer. Similar results were obtained when another monomeric disintegrin, echistatin, was used (data not shown). The ability of contortrostatin to inhibit motility is not restricted to MDA-MB-435 cells. We have observed an inhibitory effect in a variety of tumor cells including T24 bladder carcinoma, KSY-1 Kaposis's sarcoma, and various glioma cell lines (unpublished observations).

Figure 11:
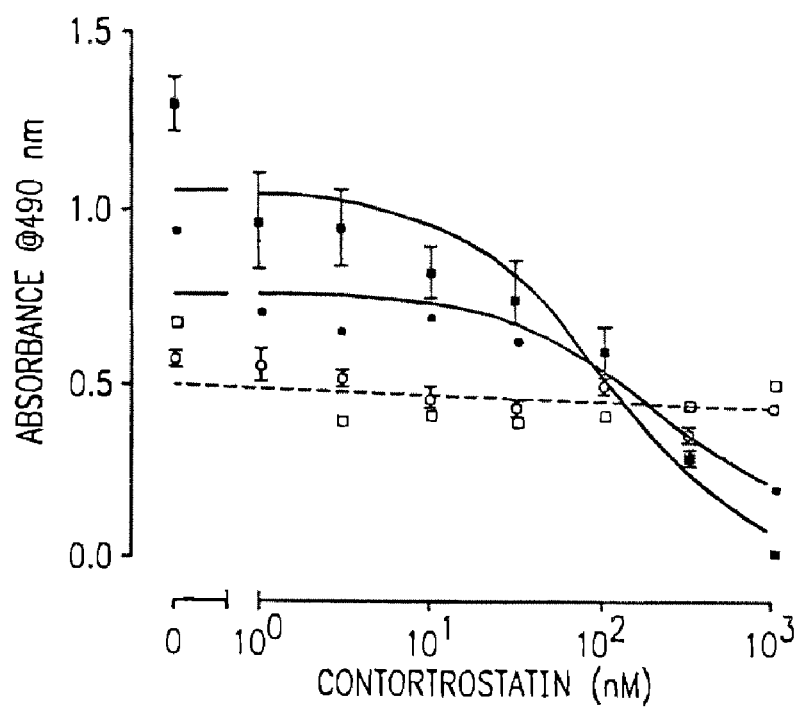
FIG. 11. Contortrostatin has no effect on T24 cell adhesion to Matrigel (☐), but completely blocks adhesion to vitronectin (■). T24 cells selected for the absence of αvβ3 integrin expression are similarly unaffected in binding to Matrigel by contortrostatin (○) but are effectively inhibited on vitronectin (●). Similar results were obtained in adhesion assays with MDA-MB-435 cells.

The inhibitory activity of contortrostatin on motility is not due to detachment from the substratum. Cellular adhesion to solid phase substrates was measured by immobilizing Matrigel (diluted 1:100) or vitronectin (10 µg/ml) into the wells of a 96-well culture plate by overnight incubation at 4° C. Unbound protein was removed by washing with PBS and remaining surfaces were blocked by incubation with 1% BSA/PBS for 1 h at room temperature. Cells were harvested and washed four times with serum-free medium. After adjusting density to $5 \times 10^5$ cells/ml, cells were treated with various concentrations of contortrostatin and incubated 20 min at room temperature prior to addition to the coated wells. Cells were allowed to adhere 30 min at which time unbound cells were removed. The number of cells remaining was quantitated calorimetrically using the CellTiter 96 Nonradioactive Cell Proliferation Kit (Promega, Madison, Wis.) and data was processed using Prism software (Graph Pad, La Jolla, Calif.). FIG. 11 shows that while contortrostatin can effectively inhibit cell adhesion to vitronectin, this disintegrin has no effect on T24 cell adhesion to Matrigel. This is a consistent observation made with all cell lines tested.

Example 8

CN Inhibits Growth and Metastasis of MDA-MB-435 Breast Cancer in Nude Mouse Experimental Model A spontaneous (orthotopic) metastatic model of nude mice has been established by implantation of MDA-MB-435 cells ($5 \times 10^5$ in 0.1 ml) in the mammary fat pads (mfp). Palpable tumors appeared by the 10th day post-implantation. Daily injections of CN into the tumor masses of each of the groups are carried out, started at the 14th day post-implantation. By the 8th week post-implantation, tumors were removed. The animals were allowed to survive for 2 more weeks without CN administration. The animals were then sacrificed and lung metastases were carefully examined.

Figure 12:
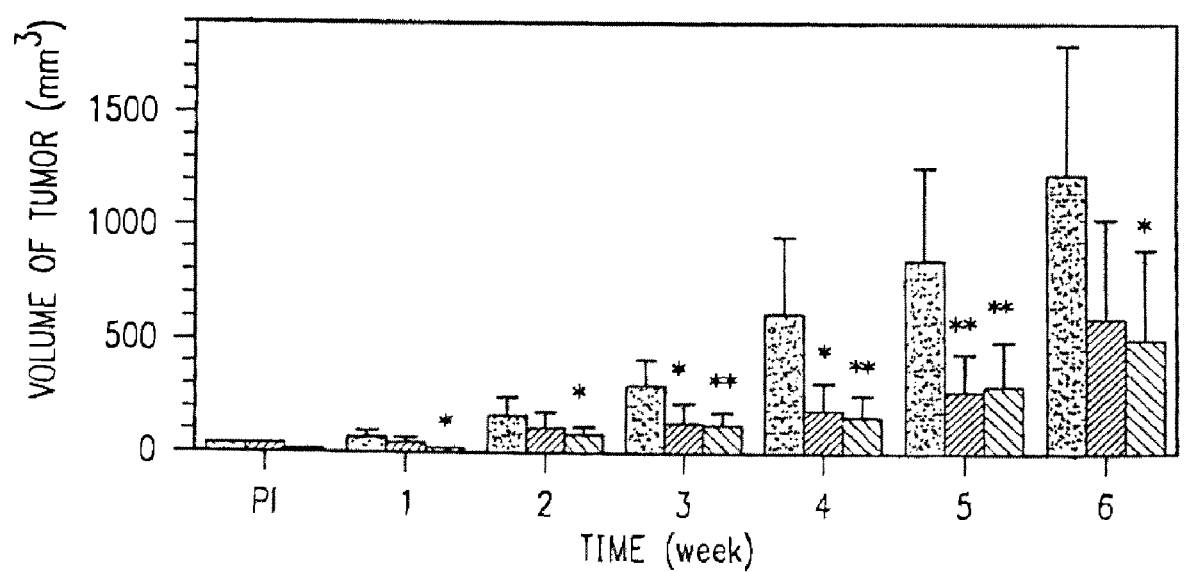
FIG. 12 shows the effect of CN on the growth MDA-MB-435 tumor in experimental nude mice.

Referring to FIG. 12, our findings indicate that local injection of CN substantially inhibited the growth rate of the tumor. The volumes of tumor masses (mean±S.D.) of control (dark bars), low-dosage (0.5 µg/day, gray bars), and high-dosage (5µ/day, light gray bars) CN-treated group are shown. The seven clusters of bars from left to right represent the data of pre-injection (PI, 14th day post-implantation) and the 1st through 6th week of injection. Student t-tests were employed to test the significance of differences. * and ** indicate $P<0.05$ and $p<0.01$, respectively. The mean weight of tumors treated by high-dose CN (5 µg/day) is significantly lower than control group ($P<0.05$). Table I shows the incidence of lung metastasis based on gross examination and counting of surface nodules. Metastatic spread in the control group is much more extensive than the high dose CN group which showed >90% inhibition of metastasis. These data demonstrate the potential therapeutic role of CN in the treatment of human breast cancer.

TABLE I

Effect of Contortrostatin on the Incidence of Metastatic MDA-MB-435 Breast Cancer in Nude Mouse Experimental Model.

| | Metastasis Incidence | | | |
|---|---|---|---|---|
| Groups | In situ relapse | Mean size of relapse tumor (mm³) | # of nodules in lung (median) | Other Organs[1] |
| Control | 4/5 | 66.7 ± 51.7 | 47.5[2] | 5/5 |
| CN (5 µg/day) | 2/6 | 48.7 ± 10.5 | 4.5 | 2/6 |

[1]Organs include: Chest wall, mediastinum, diaphragm, and pleurae
[2]In 2/5 animals, lungs are directly invaded by cancer cells from pleurae and mediastinum.

Example 9

CN Inhibits Angiogenesis Induced by MDA-MB-435 Tumor in CAM

Figure 13A:
FIG. 13 is a photograph demonstrating tumor induced angiogenesis in a control chick embryo chorioallantoic membrane (CAM) (FIG. 13A), CAM treated with 20 μg of CN (FIG. 13B), and CAM treated with 150 μg of CN (FIG. 13C)
Figure 13B:
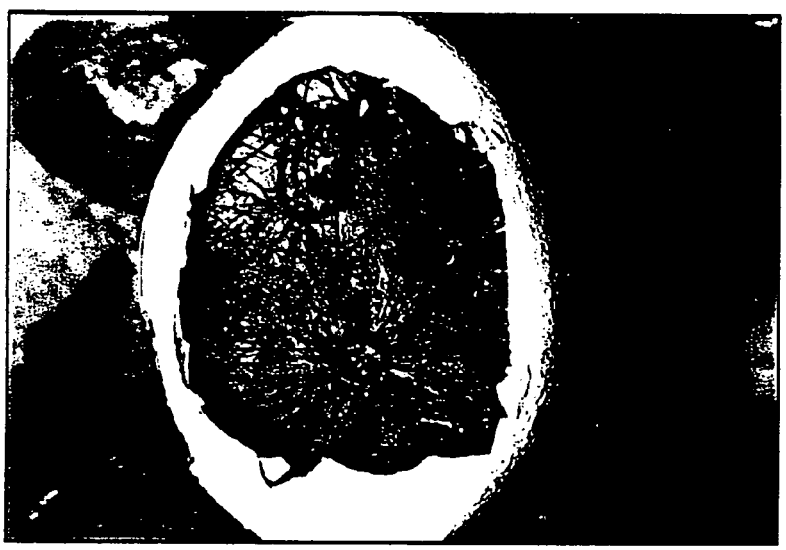
Figure 13C:

The hypothesis that an inhibitory effect on the growth of tumors probably results at least in part from the blockage of angiogenesis by CN has been preliminarily verified by observing the effect of CN on tumor induced angiogenesis on chick embryo chorioallantoic membrane (CAM). MDA-MB-435 tumor masses were inoculated on CAM of 10-day chick embryos. CN at various dosages were injected intravenously into CAM on day 2 post-inoculation. Tumor induced angiogenesis and inhibitory effect of CN on angiogenesis can be easily observed in CAM after 3 days of incubation. As shown in FIG. 13, vessels are distributed in a convergent manner with the tumor mass in the center in control embryo. Chick embryo is immunodeficient, and thus allows the growth of implanted MDA-MB-435 tumor. The embryos are incubated at 37° C. with humidity at 60%. CN at various dosages was injected intravenously into CAM on day 2 post-inoculation. Tumor induced angiogenesis on the 3rd day is demonstrated the photos. On the top (FIG. 13A) is the control embryo. The vessels are distributed in a convergent manner with the tumor mass in the center. In the middle (FIG. 13B) is the CAM treated with 20 µg of CN. On the bottom (FIG. 13C) is the CAM treated by 150 µg of CN. The 20 µg CN treated embryo vessels are thinner and less dense than control; tumor mass is smaller than that on control CAM. On CAM treated by 150 µg of CN the vessels are even thinner and the convergent distribution pattern disappears completely; there is a necrotic tumor mass with a volume significantly smaller than control and low dose CN, presumably due to the lack of blood supply (FIG. 13).

Example 10

CN has no Effect on Growth of MDA-MB-435 Cells in Vitro

Figure 14:
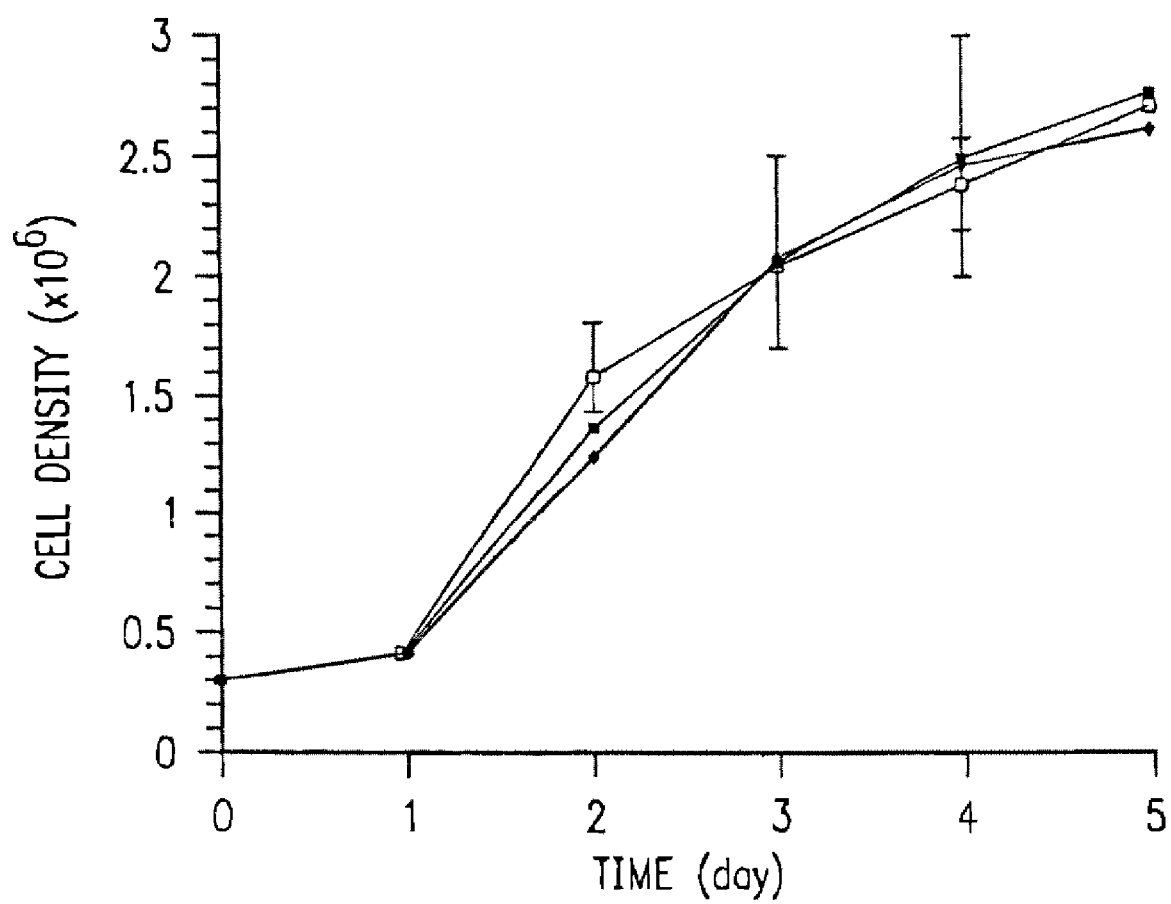
FIG. 14 shows the effect of CN on the proliferation of MDA-MB-435 cells in vitro.
Figure 16A:
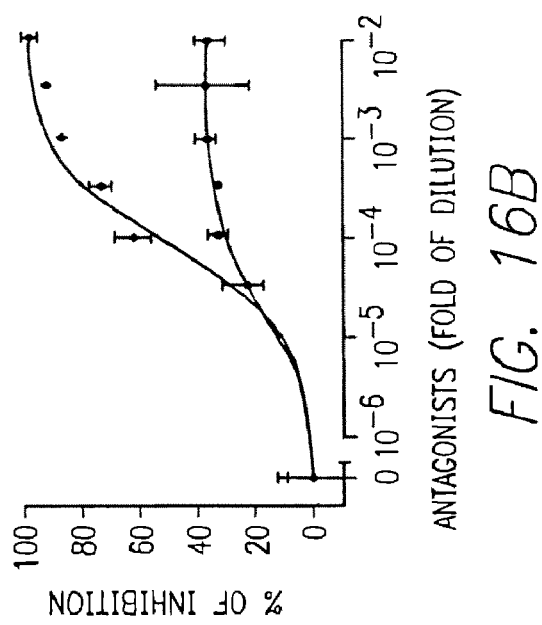
FIG. 16. Inhibition of adhesion of T24 and T24-β3 neg. cells to vitronectin by different antagonists of vitronectin receptors. (A): contortrostatin inhibits adhesion of T24 completely (squares), whereas 7E3 only partially inhibits adhesion (triangles). (B): P1F6 alone (solid circles) only partially inhibits adhesion of T24, but in combination with 7E3 (10 μg/ml), P1F6 (diamonds) is able to inhibit adhesion completely. (C): contortrostatin inhibits adhesion of T24-β3 neg. completely (squares), whereas 7E3 has no effect on adhesion (triangles). (D): P1F6 alone (solid circles) significantly inhibits adhesion of T24-β3 neg. The presence of 7E3 (10 μg/ml) does not enhance the inhibitory ability of P1F6 (diamonds). Each data point represents mean±standard deviation of three individuals replicates which were linked by non-linear regression curves. The experiments were repeated three times with identical results.
Figure 16B:
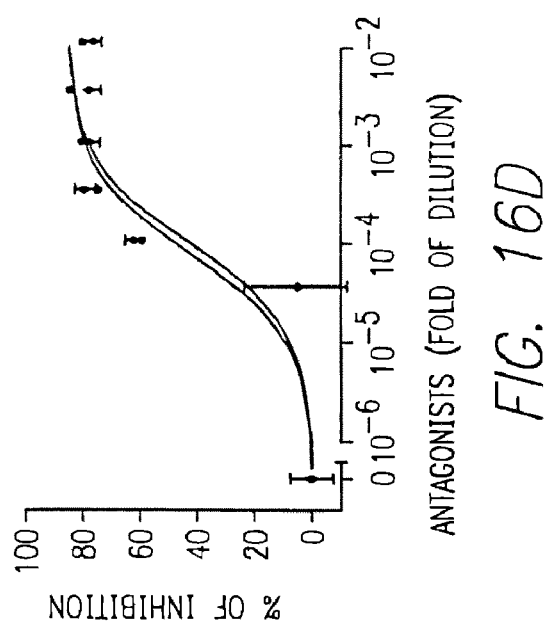
Figure 16C:
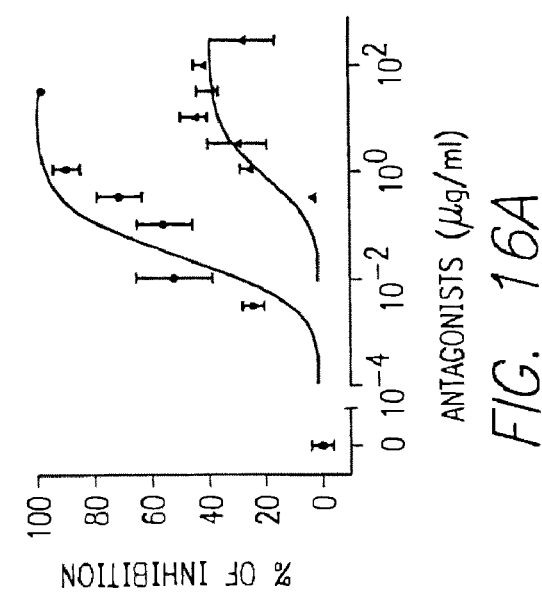
Figure 16D:
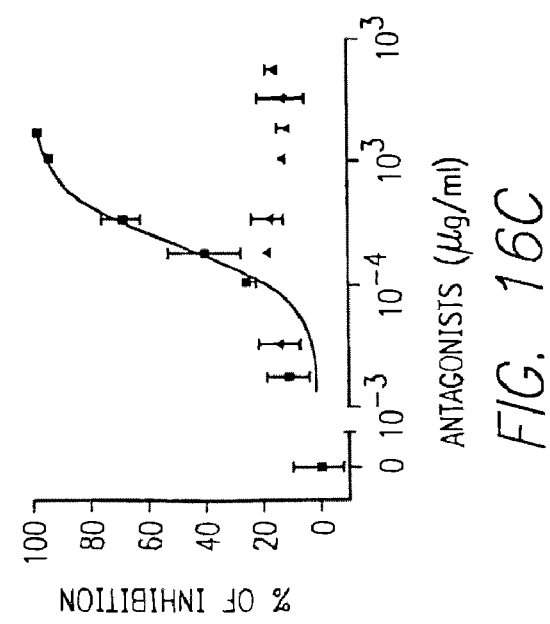

MDA-MB-435 cells (0.3×106/m]) were added to each well of a 6-well cell culture plates coated with 1/100 dilution of Matrigel. Cells were then treated with CN at various concentration. Growth curves of MDA-MB-435 cells in vitro without CN (circles), and with CN at 100 nM (triangles), and 500 nM (diamonds) are illustrated. Six-well cell culture plates coated with Matrigel (1/100 dilute) were seeded with 3 ml of MDA-MB-435 cell suspension (0.3×10$^6$/ml). Cell density was determined every 24 hours. Referring to FIG. 14, cells in the presence of CN proliferate equally well as control cells. The result indicate that CN has no direct cytotoxicity during in vitro culture of MDA-MB-435 cells.

Example 11

CN is Effective and Well Tolerated in Vivo

It can be concluded from the chronic experiment with nude mice mentioned above that CN is not toxic. Despite its platelet aggregation inhibitory activity, no spontaneous hemorrhage is observed during the experiment. Some bleeding at the injection sites in CN treated animals, however, was noticed.

CN is a novel antimetastatic agent. We hypothesize that CN blocks several critical steps (e.g. adhesion, invasion, angiogenesis) in cancer metastasis and progression. Therefore, it is more potent than other agents which block a single step.

Example 12

Contortrostatin Binds to Integrin $\alpha v\beta 5$ as a Mechanism of its Antineoplastic Activity Introduction: Disintegrins, the most potent known inhibitors of integrin function, are a class of cysteine-rich peptides isolated from the venom of the Viperidae and Crotalidae families of snakes. They bind with high affinity to integrins on the surface of platelets and other cells. The sequence RGD (Arg-Gly-Asp) is conserved in all of these peptides. This sequence is believed to bind to the platelet surface fibrinogen receptor $\alpha IIb\beta 3$, which results in the inhibition of fibrinogen-dependent platelet aggregation. Except for barbourin, a KGD-containing (instead of RGD) disintegrin which is a relatively specific antagonist for $\alpha IIb\beta 3$, other disintegrins are rather unspecific and can block the function of other $\beta 3$ integrins, as well as $\beta 1$ integrins.

Contortrostatin is a disintegrin from *Agkstrodon contortrix contortrix* (southern copperhead) venom. Unlike other disintegrins, contortrostatin is a homodimer with a mass of 13,505 for the intact protein and 6,956 for the reduced and pyridylethylated protein as shown by mass spectrometry. In addition to its platelet aggregation inhibitory activity by binding to $\alpha IIb\beta 3$, contortrostatin is also a novel antiangiogenic agent. Our recent studies indicate that $\alpha v\beta 3$ on vascular endothelial cells is an important integrin to which contortrostatin binds. We have observed that contortrostatin blocks several critical steps including cell adhesion, invasion, and angiogenesis in cancer metastasis and progression. In previous studies, we found that contortrostatin inhibits VEGF-induced angiogenesis, which is reported to be regulated via an $\alpha v\beta 5$-mediated signal transduction pathway. In this example, we prove that contortrostatin binds directly to $\alpha v\beta 5$ and blocks the function of this integrin.

Significance: The function of $\alpha v\beta 5$ has been indicated by many studies. Friedlander and colleagues found that blockade of $\alpha v\beta 3$ only affects bFGF induced angiogenesis, whereas blockade of $\alpha v\beta 5$ exclusively inhibits VEGF induced angiogenesis, suggesting that the growth factors utilize distinct signal transduction pathways which depend on different integrins. Interestingly, contortrostatin inhibits angiogenesis induced by both bFGF and VEGF in a chick chorioallantoic membrane model. Although $\alpha v\beta 5$ participates in the initiation of cell adhesion to vitronectin, unlike $\alpha v\beta 3$ which mediates cell migration constitutively, $\alpha v\beta 5$ mediates migration only when activated by growth factors, such as insulin-like growth factor-1 (IGF-1), epidermal growth factor (EGF), and transforming growth factor-$\alpha$(TGF-$\alpha$).

Cooperation of growth factors and $\alpha v\beta 5$-dependent migration and signal transduction have also been revealed. Although focal adhesion kinase (FAK) colocalizes with $\alpha v\beta 5$ upon adhesion of the host cells, tyrosine phosphorylation of FAK does not increase until protein kinase C (PKC) is activated, perhaps as a result of upstream tyrosine kinase activation by growth factor receptors. Specific PKC inhibitor blocks VEGF-induced angiogenesis. On the downstream side of signal transduction pathway, Yebra et al reported that $\alpha v\beta 5$ mediated cell migration requires a late activation event involving NF$\kappa$B induced de novo gene transcription and protein synthesis. Recent research by the same group of investigators showed that activation of PKC and the consequent increase of $\alpha v\beta 5$-dependent cell migration requires up regulation of urokinase-type plasminogen activator/urokinase-type plasminogen activator receptor (uPA/uPAR) complex and uPA enzymatic activity. The $\alpha v\beta 5$-dependent intracellular signal cascade is clearly distinct from that of $\alpha v\beta 3$, and it specifically regulates migration on vitronectin, but not other ECM proteins.

These findings support the idea that $\alpha v\beta 5$ has an important role in mediating cell motility during angiogenesis and metastasis. Therefore, contortrostatin, as an antagonist of $\alpha v\beta 5$, may be of significant utility for anti-angiogenic and anti-metastatic therapy. We discovered a novel mechanism of action for the anti-metastatic and anti-angiogenic activity of contortrostatin. This is the first observation that a disintegrin binds to $\alpha v\beta 5$, an important integrin in tumor metastasis and angiogenesis.

Cell adhesion assay: Human bladder carcinoma T24 cells were purchased from ATCC, and grown in RPMI1640 medium containing 5% fetal bovine serum. T24-$\beta 3$ neg. cells were isolated by 6 rounds of negative FACS selection with anti-$\alpha v\beta 3$ monoclonal antibody (mAb) LM609. FACS analysis was then performed as follows. The cells were resuspended in 1% BSA/PBS at a density of $1\times 10^7$/ml. Aliquots of 100 µl were incubated with anti-$\alpha v\beta 3$ mAb 7E3 or anti-$\alpha v\beta 5$ mAb P1F6 (final concentration 5 µg/ml) at room temperature for 30 minutes. The cells were washed twice and resuspended in 1% BSA/PBS. Goat anti-mouse IgG conjugated with FITC was added to the suspension at a final titer of 1:200. After 30 minutes incubation at room temperature in darkness, unbound FITC-conjugated IgG was washed off, and the fluorescent intensity of the cells was analyzed using flow cytometry (FACScan, Becton Dickinson, Bedford, Mass.). Tests were performed in duplicate and the experiment was repeated three times. The results clearly indicate that T24 cells express both integrins $\alpha v\beta 3$ (major) and $\alpha v\beta 5$ (minor), but T24-$\beta 3$ neg. cells only express $\alpha v\beta 5$ (FIG. 15).

Individual wells of 96-well plates were coated at 4° C. overnight with 100 µl of vitronectin (1 µg/well). Excess proteins were washed off with three washes of phosphate buffered saline (PBS), followed by blocking with 1% bovine serum albumin (BSA) in PBS. Aliquots (100*l) of cells ($5\times 10^5$ cells/ml) were incubated at room temperature for 20 minutes with antibodies or contortrostatin before being applied to the coated wells. Treated cells were allowed to adhere to the wells for 30 minutes at 37° C. Unbound cells were washed off with serum-free medium. Cell adhesion was quantified either by CellTiter 96™ Aqueous Proliferation Assay kit (Promega, Madison, Wis.). Each inhibitor concentration was tested in triplicate, and assays were performed at least three times yielding identical results.

It was previously demonstrated that contortrostatin inhibits adhesion of human breast cells (MDA-MB-435) on vitronectin coated plate. Integrin $\alpha v\beta 3$ was identified as a binding site of the disintegrin in this cell line. Similarly in this study, contortrostatin inhibited adhesion of human bladder carcinoma T24 cells to immobilized vitronectin in a dose-dependent manner, with 100% inhibition at a concentration less than 10 µg/ml (FIG. 15-A). As already shown, FACS analysis indicated that T24 cells express both $\alpha v\beta 3$ and $\alpha v\beta 5$. While the maximum effect of anti-$\alpha v\beta 3$ (7E3) was no higher than 40% at concentrations up to 100 µg/ml (FIG. 16-A), the effect of anti-$\alpha v\beta 5$ (P1F6) on adhesion was below 40% at 1:100 dilution (FIG. 16-B). However, the combination of 7E3 (with constant concentration of 10 µg/ml at which maximal inhibition was reached) and increasing concentrations of P1F6 eventually lead to almost 100% inhibition of adhesion. The results suggest that both $\alpha v\beta 3$ and $\alpha v\beta 5$ mediate the adhesion of T24 cells to vitronectin. Complete elimination of cellular attachment to vitronectin requires combination of antibodies against both integrins. On the other hand, contortrostatin effectively blocks the adhesion of these cell lines to vitronectin. This finding strongly support our hypothesis that contortrostatin binds to $\alpha v\beta 5$ as well as $\alpha v\beta 3$.

To further distinguish the functional blockage by contortrostatin of the two integrins, $\alpha v\beta 3$-negative T24 mutant cells (T24-$\beta 3$ neg.) were employed for the adhesion assay. Although inhibition by 7E3 was negligible, contortrostatin completely inhibited adhesion of the cell line (FIG. 16-C). The adhesion of T24-$\beta 3$ neg. cells to vitronectin was predominantly mediated by $\alpha v\beta 5$, since the inhibitory effect of P1F6 was as high as 80% (FIG. 16-D) in contrast with below 40% on T24 cells (FIG. 16-B). The inhibition curve of P1F6 was not altered by addition of 7E3 (FIG. 15-D). The result of this assay indicated that adhesion of the $\alpha v\beta 3$ negative cell line T24-$\beta 3$ is mediated by $\alpha v\beta 5$. Blockage of $\alpha v\beta 5$ by a monoclonal antibody completely inhibits adhesion. Contortrostatin was shown to be able to prevent adhesion of these cells to vitronectin. Thus, contortrostatin must bind to integrin $\alpha v\beta 5$.

Figure 17:
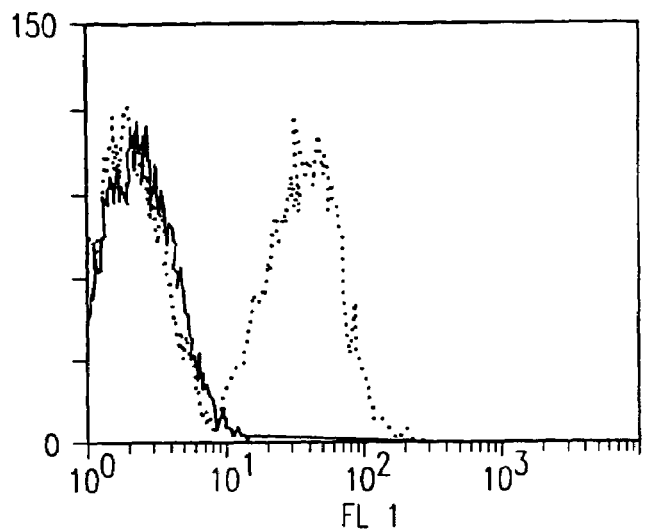
FIG. 17. The expression pattern of integrins in the OVCAR-5 cell line. The expression pattern of integrins in the OVCAR-5 cell line was analyzed by FACS using monoclonal antibodies anti-αvβ3 (7E3) and anti-αvβ5 (P1F6). The solid peak is the background, the dotted peak that merges with the background represents bound 7E3, and the dotted peak to the right represents P1F6. This shows conclusively that the OVCAR-5 cells possess integrin αvβ5 but not αvβ3.

Cell invasion assay: To test whether the binding of contortrostatin to $\alpha v\beta 5$ inhibits invasion of cancer cells, invasion assays were performed with highly invasive human ovarian carcinoma cell OVCAR-5, which express $\alpha v\beta 5$ but not $\alpha v\beta 3$. The expression pattern of integrins in the OVCAR-5 cell line was analyzed by FACS using monoclonal antibodies anti-$\alpha v\beta 3$ (7E3) and anti-$\alpha v\beta 5$ (P1F6). As shown in FIG. 17, the solid peak is the background, the dotted peak that merges with the background represents bound 7E3, and the dotted peak to the right represents P1F6. This shows conclusively that the OVCAR-5 cells possess integrin $\alpha v\beta 5$ but not $\alpha v\beta 3$.

Modified Boyden chambers were employed to measure invasion. Filters of 12 mm Boyden chamber with 12 µm pore size (Corning Costar, Cambridge, Mass.) were coated with 1:50 dilution of Matrigel in serum free medium. Cells ($2.5 \times 10^5$ cells in 200 µl of medium) pre-treated with contortrostatin, antibodies against different integrins, or vehicle (control), were applied to the upper wells. HT1080 conditioned medium was added to the bottom well. The cells were incubated at 37° C. for 8 hr., at which point cells on the top side of the membrane were removed with a wet cotton swab. Cells which invaded through the filter membrane were fixed and stained with Diff-Quik™ staining kit (Dade Diagnostics of P. R. Inc., Aguada, Puerto Rico). The membranes were removed from the holder, and were mounted on slides. Migration was quantitated by determining the number of cells in five randomly selected high power vision field using a microscope. Each inhibitor concentration was tested in duplicate, and the experiments were repeated three times to confirm results.

Figure 18:
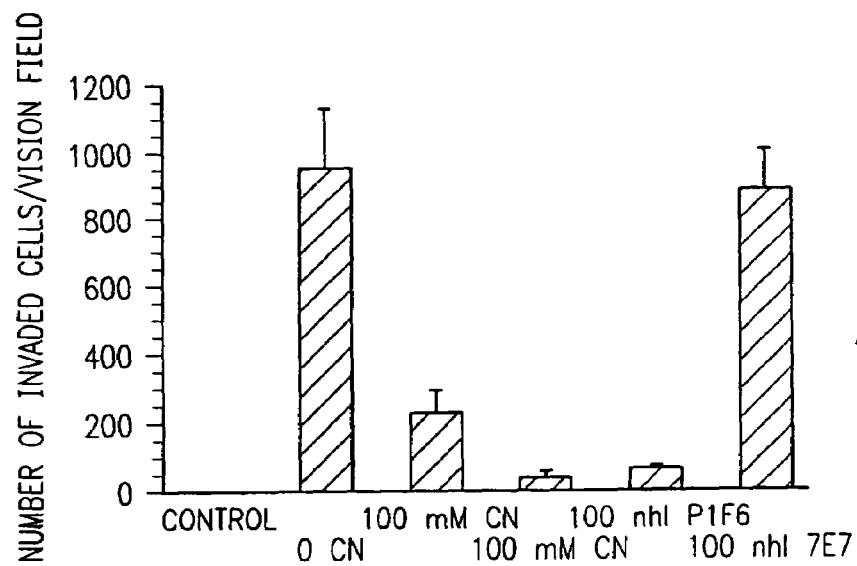
FIG. 18. CN and other antagonists of αvβ5 inhibits adhesion of OVCAR-5 cells to vitronectin. Adhesion of cancer cells to the matrix is one of the critical steps of cancer spreading and metastasis. It is well established that integrin αvβ5 mediates adhesion of cells to vitronectin. In an adhesion assay, we were able to demonstrate that adhesion of OVCAR-5 cells to vitronectin coated plate was inhibited by both CN and mAb against αvβ5 (P1F6). However, anti-αvβ3 (7E3) did not affect cell adhesion. The data suggest that CN, by blocking integrin αvβ5, disrupts adhesion of the cancer cells to vitronectin.

Neither contortrostatin, nor antibodies alone, nor the combination of the antibodies inhibited attachment and spreading of the cells to Matrigel. Therefore, the anti-invasive activities of these vitronectin receptor antagonists were independent of their anti-adhesive effect. FIG. 18 illustrates that contortrostatin (1000 nM) almost completely inhibited invasion of OVCAR-5 cells through Matrigel. Comparable inhibition was achieved with 100 nM of P1F6. However, at the same molar concentration, 7E3 showed no effect on invasion. The results strongly suggested that integrin $\alpha v\beta 5$ mediates invasion of OVCAR-5 cells through Matrigel. Contortrostatin effectively inhibits invasion of these cells due to the blockage of $\alpha v\beta 5$.

Figure 19:
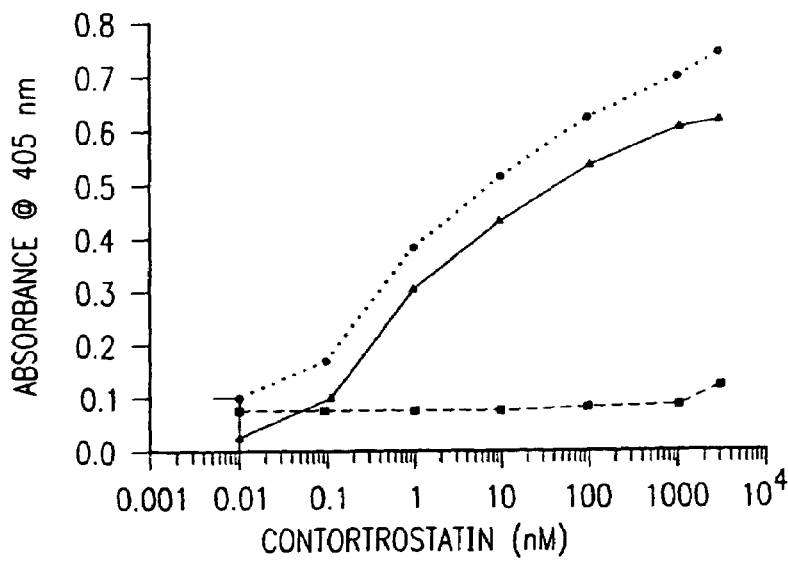
FIG. 19. Direct binding of contortrostatin to purified αvβ5: Purified αvβ5 (100 ng) immobilized in individual wells of microtiter plates. Contortrostatin at various concentration was allowed to bind to the integrin. Bound contortrostatin was quantitated using anti-serum against the disintegrin as the total binding (solid circles). Contortrostatin bound to bovine serum albumin is defined as the non-specific binding (opened squares). The specific binding (triangles) is calculated by subtraction of the non-specific binding from the total binding. Each point represents mean absorbance at 405 nm±SD from triplicate analyses. The experiment was repeated to confirm results.

Detection of the binding of contortrostatin to $\alpha v\beta 5$: Direct evidence that contortrostatin binds to $\alpha v\beta 5$ was collected by solid-phase binding assay using purified $\alpha v\beta 5$ and a modified ELISA. Soluble $\alpha v\beta 5$ (100 ng) was immobilized on wells of a 96-well plate at 4° C. overnight. Excess protein was washed off, and unbound sites were blocked with 1% BSA/PBS. Contortrostatin at various concentrations was allowed to bind to the coated plate at room temperature for one hour. After three washes with PBS, the bound contortrostatin molecules were detected with 1:1,000 antiserum against contortrostatin. Goat anti-rabbit antibody conjugated with alkaline phosphotase was used as a secondary antibody. The bound antibodies were quantitated by applying substrate disodium p-nitrophenyl phosphate (pNPP) and determining the light absorbance at 405 nm 15 minutes after the initiation of the chromagenic reaction. The background is defined by the binding of antiserum against the disintegrin to immobilized $\alpha v\beta 5$. Specific binding is obtained by subtracting the background from the total binding. Analyses of each concentration of ligand were performed in triplicate. FIG. 19 indicates that contortrostatin binds to $\alpha v\beta 5$ in a dose-dependent and saturable manner, suggesting that contortrostatin specifically binds to $\alpha v\beta 5$.

In summary, we identified $\alpha v\beta 5$ as a novel binding site for the disintegrin contortrostatin. Functional blockade of $\alpha v\beta 5$ not only inhibits the adhesion of cancer to vitronectin, but also blocks invasion of cancer cells through Matrigel artificial basement membrane. Binding of contortrostatin to $\alpha v\beta 5$ is most likely part of its anti-adhesion and anti-invasion activity.

Example 13

Contortrostatin Induces $\alpha v\beta 3$-Mediated Tyrosine Phosphorylation of CAS and FAK in Tumor Cells Summary: Contortrostatin is a homodimeric disintegrin that inhibits platelet aggregation and cell adhesion to extracellular matrix proteins by blocking integrins. The effect of contortrostatin on integrin-mediated signaling in tumor cells was investigated by studying tyrosine phosphorylation events and activation of specific signaling molecules. We found that at concentrations as low as 1 nM, soluble contortrostatin activates integrin signals leading to increased tyrosine phosphorylation of FAK and CAS, and that these signals are abolished by inhibiting Src family activity. Using transfected 293 cells expressing specific integrins, we determined that contortrostatin-generated signals are mediated exclusively by the αvβ3 integrin. This observation was extended by showing that cells lacking αvβ3 but expressing αvβ5 and αvβ1, do not respond in this way to contortrostatin treatment. In cells expressing αvβ3, blocking contortrostatin binding with antibodies against αvβ3 completely abrogates contortrostatin signals. Monovalent disintegrins echistatin and flavoridin were incapable of affecting tyrosine phosphorylation alone, but when added simultaneously with contortrostatin, completely inhibited contortrostatin-initiated signals. We propose that the homodimeric nature of contortrostatin imparts the ability to crosslink αvβ3 integrins, causing Src activation and hyperphosphorylation of FAK and CAS. This activity may represent a novel mechanism by which tumor cell motility can be inhibited.

Introduction: Integrins provide both physical anchorage to the extracellular matrix and signaling information to the interior of the cell. Both of these functions are critical to the cellular process of motility and disruption of either can lead to reduced motility [Aznavoorian, S., et al., *J. Biol. Chem.* 271: 3247-54 (1996); Wong, N. C., et al., *Clinical Exp. Metastasis.* 16: 50-61 (1998); and Garton, A. J. and Tonks, N. K., *J. Biol. Chem.* 274: 3811-3818 (1999)]. The machinery that is responsible for driving motility is complex and highly regulated, but the action of the molecular components is not fully understood. Protein tyrosine kinases are major players in mediating integrin function and their substrates are well-studied components of the integrin signaling pathways (Giancotti, F. G. and Ruoslahti, E., *Science.* 285: 1028-1032, 1999). Of the thousands of proteins in the cell, a small fraction of these undergo tyrosine phosphorylation. Many tyrosine phosphorylated proteins are found associated with integrin cytoplasmic domains in focal adhesion complexes (Burridge, K., et al., *A. Rev. Cell Biol.* 4: 487-525 (1988)]. Focal adhesion kinase (FAK) is a nonreceptor tyrosine kinase that has been implicated in a wide range of integrin- and nonintegrin-regulated cellular processes [Rodriguez-Femandez, J. L., *Bioessays.* 21: 1069-75 (1999)]. FAK associates with integrin β subunits near the cytoplasmic face of the cell membrane where, upon integrin clustering, it can undergo trans-autophosphorylation at a specific tyrosine residue [Schaller, M. D., et al., *Mol. Cell. Biol.* 14: 1680-1688 (1994)]. This creates a binding site for the SH2 domain of another tyrosine kinase, Src, which can then catalyse the phosphorylation of FAK at other sites [Cobb, B. S., et al., *Molecular & Cellular Biology.* 14: 147-55 (1994)]. Another Src substrate is CAS, an adapter protein that contains multiple tyrosines that can be phosphorylated [Vuori, K., et al., *Mol. Cell. Biol.* 16: 2606-2613 (1996)]. Although its function is not completely understood, CAS has been shown to be involved in the regulation of motility [Garton, A. J. et al. (1999) supra; Klemke, R. L., et al., *J. Cell Biol.* 140: 961-972 (1998); and Cary, L. A., et al., *J. Cell Biol.* 140: 211-221 (1998)]. Integrin signaling events are initiated by cellular adhesion to ECM proteins which leads to two-dimensional relocation of integrin receptors in the plasma membrane and reorganization of the actin cytoskeleton [Burridge, K., et al., *J. Cell Biol.* 119: 893-903 (1992)]. These events can trigger recruitment of other focal adhesion proteins as well as initiate diverging pathways such as the RAS/MAPK pathway by recruiting the Grb2 adapter protein [Schlaepfer, D. D., et al., *Mol. Cell. Biol.* 18: 2571-2585 (1998)]. Integrin clustering by the ECM has been simulated by crosslinking receptors with anti-integrin monoclonal antibodies [Komberg, L. J., et al., *Proc. Natl. Acad. Sci. USA.* 88: 8392-8396 (1991)] or with soluble multivalent integrin ligands such as vitronectin [Bhattacharya, S., et al., *J. Biol. Chem.* 270: 16781-16787 (1995)]. Both of these methods induce tyrosine phosphorylation events, including phosphorylation of FAK.

Coinciding with the increased interest in integrin biology relating to cancer and angiogenesis, disintegrins have been used to study the effects of integrin antagonism in these processes [Trikha, M., et al., *Cancer Res.* 54:4993-8. (1994); Sheu, J.-R., et al., *Biochim. Biophys. Acta.* 1336: 445-454 (1997); Yeh, C. H., et al., *Blood.* 92: 3268-3276 (1998); Kang, I.-C., et al., *Cancer Research.* 59: 3754-3760 (1999); and Zhou, Q., et al., *Angiogenesis* 3:259-269 (1999)]. One integrin, αvβ3, has received attention recently for its role in cancer, and particularly for its role in angiogenesis. This vitronectin receptor has been shown to be necessary for angiogenesis and blockage of αvβ3 induces endothelial cell apoptosis in newly sprouting blood vessels [Brooks, P. C., et al., *Science.* 264: 569-571 (1994a); and Brooks, P. C., et al., *Cell.* 79: 1157-1164 (1994b)]. Contributing to its regulation of angiogenesis and tumor invasiveness is the ability of αvβ3 to bind the extracellular matrix-degrading protease, MMP2, localizing its activity to the leading edge of a migrating cell and facilitating penetration through the matrix [Brooks, P. C., et al., *Cell.* 85: 683-693 (1996)]. The αvβ3 integrin has been shown to be involved in tumor cell motility and metastasis and antagonists of this receptor inhibit these processes [Aznavoorian, S., et al. (1996) supra; and Beviglia, L., et al., *Oncology Research* 7: 7-20 (1995)]. Small peptides containing the RGD sequence are commonly used integrin antagonists, but can be up to 10,000-fold less potent than disintegrins [Pfaff, M., et al., *Cell Adhesion Commun.*, 2: 491-501 (1994)]. In the reports using disintegrins as inhibitors of angiogenesis [Sheu, J.-R. et al. (1997) supra; Yeh, C. H., et al. (1998) supra; and Kang, I.-C., et al. (1999) supra] these proteins are described as passive integrin antagonists, preventing αvβ3 from binding to the ECM and blocking normal signals mediated by this integrin.

Contortrostatin is an αvβ3-binding disintegrin that is also an inhibitor of angiogenesis [Zhou, Q., et al., (1999) supra] and has a structure that is unique among other members of the family. This protein is a member of a growing subfamily of dimeric disintegrins [Marcinkiewicz, C., et al., *J. Biol. Chem.* 274: 12468-12473 (1999a); and Marcinkiewicz, C., et al., *Biochemistry.* 38: 13302-9 (1999b)] but is distinguished since it is a homodimer with each subunit containing an RGD motif [Trikha, M., et al., *Thrombosis Research* 73:39-52 (1994); and Zhou, Q., et al., *Archs Biochem. Biophys.* 375: 278-288 (2000)]. In this example, we demonstrate that contortrostatin acts as an effective inhibitor of tumor cell motility, and we provide data suggesting that the contortrostatin mechanism represents a novel means by which cell motility can be inhibited. Contortrostatin accomplishes this inhibition by combining passive integrin blockade with active disruption of αvβ3 signaling, likely through integrin crosslinking, which causes major alterations in the actin cytoskeleton and focal adhesion structure. Moreover, contortrostatin has the unique ability to act as an integrin agonist by stimulating αvβ3-mediated tyrosine phosphorylation of important signaling molecules in tumor cells, an activity not found in monomeric disintegrins.

Experimental Procedures:

Materials—MDA-MB-435 human mammary carcinoma cells were obtained from Janet Price (M.D. Anderson Cancer Center Houston, Tex.). T24 human bladder carcinoma cells were purchased from ATCC (Manassas, Va.). 293 human embryonic kidney cells transfected with cDNA for β3 and β5 integrin subunits and parental 293 cells were provided by Dr.

Jeffrey Smith (The Burnham Institute, La Jolla, Calif.) [Lin, E. C. K., et al., *J. Biol. Chem.* 272(38), 23912-23920 (1997)]. OVCAR-5 human ovarian carcinoma cells were from Dr. Thomas Hamilton (Fox Chase Cancer Center, Philadelphia, Pa.). Contortrostatin was purified from the venom of the southern copperhead (*Agkistrodon contortrix contortrix*) as described previously [Trikha et al, (1994) *Thrombosis Research*, supra; and Trikha et al., (1994) *Cancer Research*, supra]. The monomeric disintegrins echistatin and flavoridin, and the general protease inhibitor cocktail used in lysis buffers were obtained from Sigma (St. Louis, Mo.). Vitronectin was purchased from Becton Dickinson (Bedford, Mass.). PPI Src inhibitor was from Calbiochein (La Jolla, Calif.). Anti-phosphotyrosine monoclonal antibody (mAb) PY99 was obtained from Santa Cruz Biotechnology (Santa Cruz, Calif.). Anti-FAK and anti-CAS mAbs were purchased from Transduction Laboratories (Lexington, Ky.) and 7E3 mAb was provided by Centocor (Malvern, Pa.).

Cell culture, preparation and stimulation—T24 cells were maintained in RPMI 1640 medium containing 5% fetal bovine serum, and MDA-MB-435 and 293 cells were maintained in Dulbecco's modified Eagle's medium with 10% serum at 37° C. in 5% $CO_2$. Cells were washed with phosphate-buffered saline (PBS) and starved in the appropriate serum-free medium for 6 h at 37° C. Cells were detached by brief treatment with 0.05% trypsin/0.02% EDTA in PBS and collected by centrifugation, resuspended in soybean trypsin inhibitor (1 mg/ml in serum-free medium), and washed in 2% bovine serum albumin/serum-free medium. Cells were maintained in suspension for 1 h in 2% bovine serum albumin/serum-free medium at 37° C. with end-over-end agitation. Quiescent cells ($3 \times 10^6$/ml) were treated with disintegrins or other reagents while in suspension, or were allowed to adhere to Matrigel (Becton Dickinson, Bedford, Mass.) diluted 1:100 with serum-free medium during treatment.

Lysate preparation and immunoprecipitation—Suspended and adherent cells were washed twice with cold PBS and lysed in cold lysis buffer (50 mM Tris, pH 8.0, 150 mM NaCl, 1% Nonidet P-40, 0.5% deoxycholate, 0.1% SDS, protease inhibitor cocktail, 1 mM sodium pyrophosphate, 1 mM sodium orthovanadate, 50 mM sodium fluoride). After 10-15 min incubation on ice, insoluble material was removed by centrifugation at 14,000 RPM in a microcentrifuge for 15 min. Supernatants were collected and total protein concentrations standardized by the BCA protein assay (Pierce, Rockford, Ill.). Immunoprecipitation was carried out by incubating whole cell lysates (200 μg total protein) with 1.25 μg anti-FAK or anti-CAS mAb 4-6 h at 4° C. followed by 20 μl protein G-agarose overnight at 4° C. Immunoprecipitates were washed 4 times in lysis buffer without inhibitors and dissociated by adding SDS-PAGE sample buffer and boiling 5 min. Whole cell lysates (30 μg total protein) or immunoprecipitates were resolved by 7.5% SDS-polyacrylamide gel electrophoresis and transferred to nitrocellulose membranes.

Immunoblotting—Membranes were blocked with 5% nonfat milk/Tris-buffered saline/0.1% Tween 20 (blocking buffer) 1 h at room temperature or overnight at 4° C. Primary antibody incubations were performed in blocking buffer for 1 h at room temperature. After washing in Tris-buffered saline/0.1% Tween 20, membranes were incubated with horseradish peroxidase-conjugated secondary antibody in blocking buffer 1 h at room temperature. Membranes were washed extensively. Immunoblots were developed using Super Signal West Pico Chemiluminescent Substrate from Pierce. Densitometry was performed using UN-SCAN-IT$_{Tm}$ software (Silk Scientific, Orem, Utah))

Figure 20:
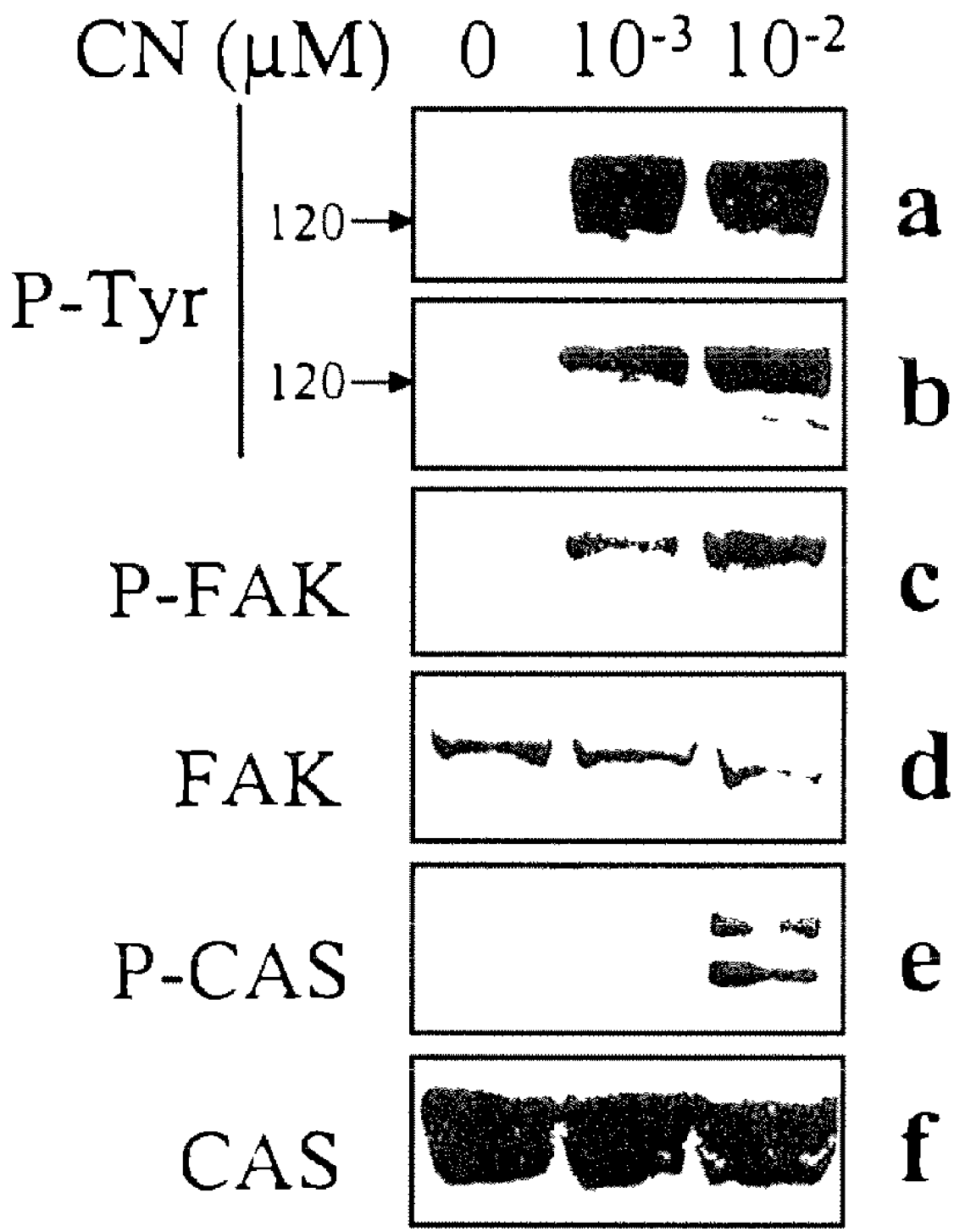
FIG. 20. Contortrostatin induces tyrosine phosphorylation events in tumor cells. Using suspended T24 cells (a) or MDA-MB-435 cells (b) it is demonstrated that contortrostatin, at the indicated concentrations, stimulates tyrosine phosphorylation of 120-140 kDa proteins after treatment for 10 min. By specific immunoprecipitation and phosphotyrosine immunoblotting, it is shown that FAK and CAS undergo tyrosine phosphorylation in MDA-MB-435 cells in response to contortrostatin treatment (c and e). Antibodies used for immunoprecipitation were used for immunoblotting to demonstrate equal loading of protein (d and f).

Results:

Contortrostatin treatment induces protein tyrosine phosphorylation in tumor cells—To investigate the role of contortrostatin in regulating overall tyrosine phosphorylation in tumor cells, MDA-MB-435 human breast carcinoma cells were treated for 10 min with various concentrations of soluble contortrostatin while in suspension. The cells showed a dramatic increase in tyrosine phosphorylation of proteins with molecular weights from 120-140 kDa following contortrostatin treatment (FIG. 20). Maximal levels of tyrosine phosphorylation were observed at 10 nM contortrostatin. Tyrosine phosphorylation of proteins in this size range was also observed in T24 human bladder carcinoma cells (FIG. 20) and KSY-1 Kaposi's sarcoma cells (data not shown) following contortrostatin treatment using the same methods, indicating that this phenomenon is not cell-type specific.

Figure 21:
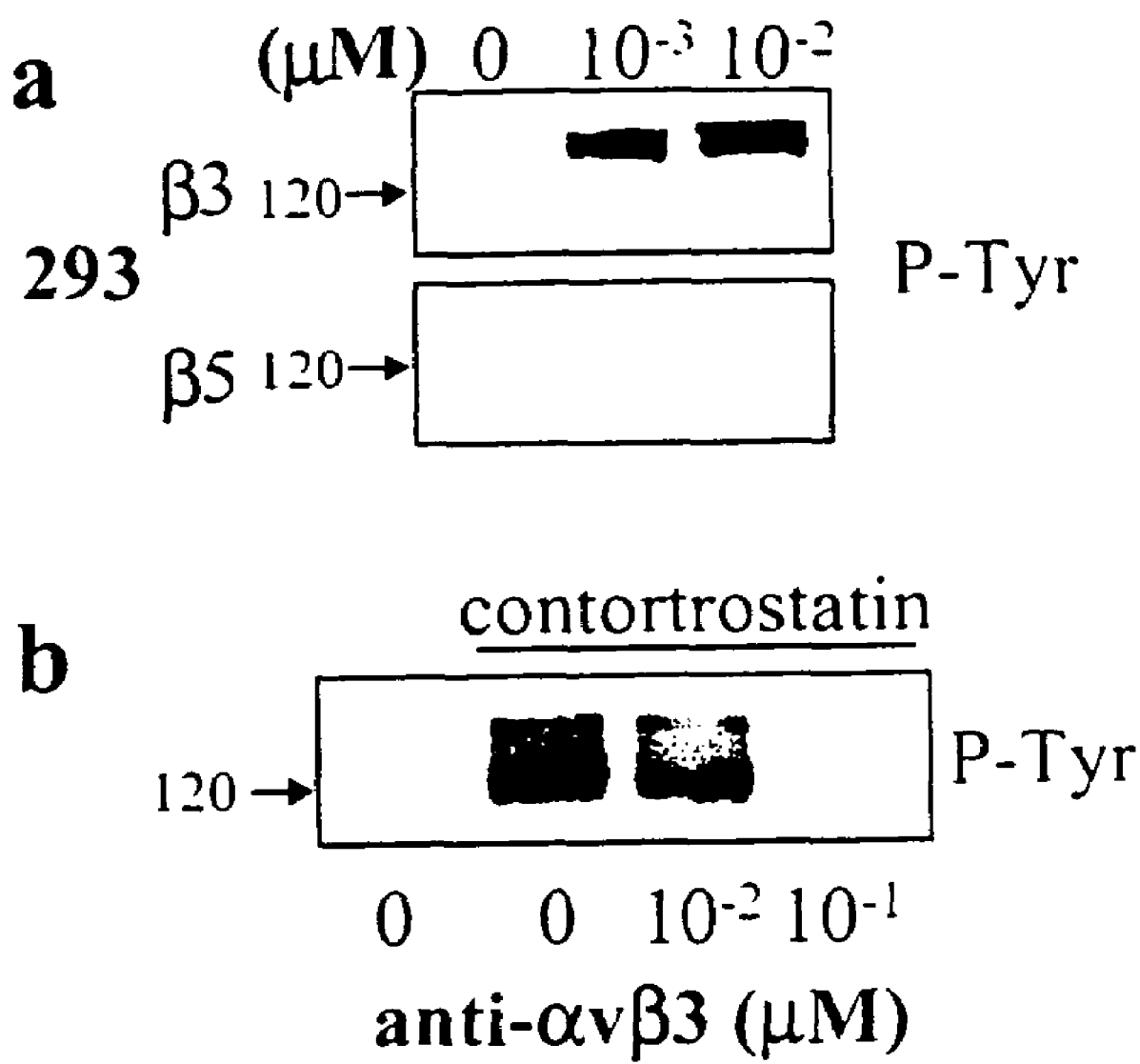
FIG. 21. The αvβ3 integrin exclusively mediates contortrostatin-stimulated tyrosine phosphorylation events. 293 cells expressing αvβ3 (β3) respond to the indicated concentrations of contortrostatin treatment with increased tyrosine phosphorylation of 120-140 kDa proteins after 10 min, while control cells expressing αvβ5 (β5) show no response (a). Treatment of T24 cells with the indicated concentrations of αvβ3, an anti-αvβ3 mAb, abrogates tyrosine phosphorylation of 120-140 kDa proteins induced by 0.01 μM contortrostatin treatment for 10 min (b).

Contortrostatin-induced tyrosine phosphorylation is mediated exclusively by the αvβ3 integrin—The integrin receptor responsible for transmitting contortrostatin-induced signals was identified by several independent experiments. 293 Human embryonic kidney cells express negligible levels of αvβ3 while expressing relatively high levels of the αv integrin subunit [Lin, E. C. K., et al., *J. Biol. Chem.* 272: 23912-23920 (1997)]. This provides an opportunity to study the function of αvβ3 by transfecting parental 293 cells with cDNA coding for the β3 subunit which results in significant expression of the αvβ3 heterodimer [Lin, E. C. K., et al. (1997) supra]. The ability of contortrostatin to induce tyrosine phosphorylation events was tested in the β3 transfectants and compared to cells transfected with the β5 integrin subunit. Integrin expression in these cells was confirmed in our laboratory. Stimulation of tyrosine phosphorylation was observed only in cells expressing αvβ3 and not in αvβ5-expressing cells (FIG. 21a). No changes in tyrosine phosphorylation were observed in parental cells (data not shown). Similarly, OVCAR-5 cells which lack αvβ3 expression were not altered in phosphotyrosine levels by contortrostatin treatment (data not shown). Furthermore, blockage of contortrostatin binding to αvβ3 with a mAb (7E3) was shown to completely abrogate tyrosine phosphorylation induced by contortrostatin in MDA-MB-435 cells (FIG. 21b).

Figure 22:
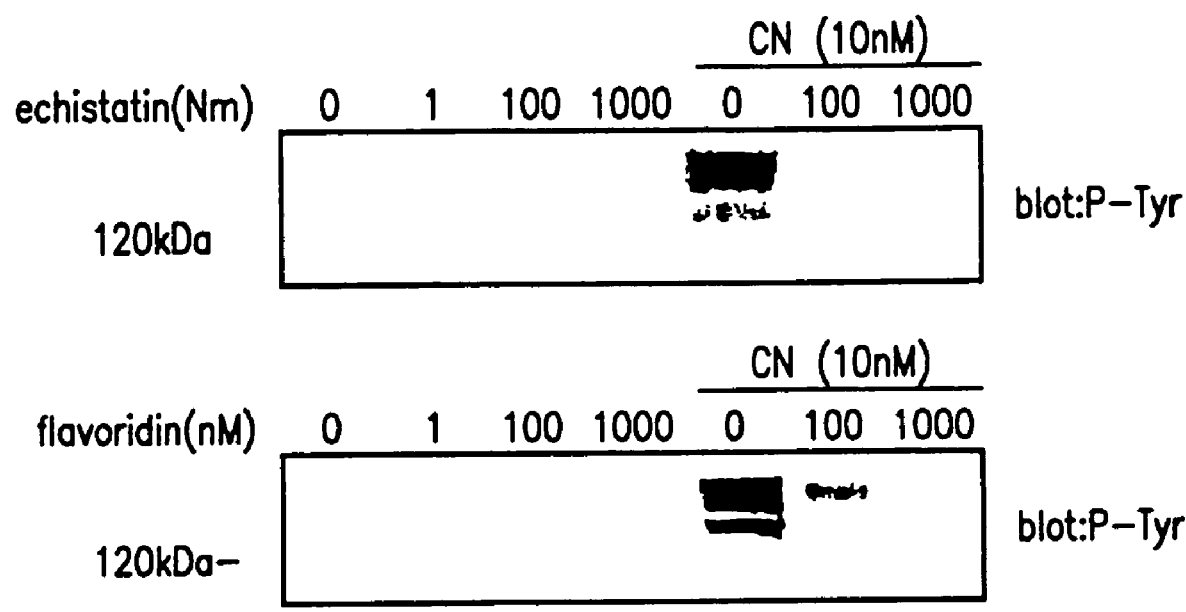
FIG. 22. Effects of monomeric disintegrins on tyrosine phosphorylation in tumor cells. MDA-MB-435 cells were treated with the indicated concentrations of echistatin (upper panel) or flavoridin (lower panel) or were treated simultaneously with monomeric disintegrins and 10 nM contortrostatin (CN) as indicated for 10 min. Lysates were analyzed for phosphotyrosine content by immunoblot as described in Experimental Procedures.

Monomeric disintegrins have no effect on tyrosine phosphorylation alone, but completely block contortrostatin-induced phosphorylation—To investigate the significance of the homodimeric structure of contortrostatin at the biochemical level, the ability of the monomeric disintegrin flavoridin to affect tyrosine phosphorylation was studied. It was found that flavoridin alone had no effect on tyrosine phosphorylation in MDA-MD-435 cells at concentrations up to 1 μM. However, flavoridin was able to completely eliminate tyrosine phosphorylation induced by contortrostatin when cells were treated simultaneously with the two disintegrins (FIG. 22). These findings were duplicated using another monomeric disintegrin, echistatin [Ritter, M. R., et al., *J. Cell. Biochem.* 79:28-37 (2000); and Ritter, M. R. and Markland, F. S., *Toxicon.* 39:283-9 (2001)]. Thus monomeric disintegrins are able to competitively inhibit the binding of contortrostatin to αvβ3, preventing crosslinking of this receptor and the initiation of tyrosine phosphorylation events, strongly suggesting that the homodimeric structure of contortrostatin enables it to function as a unique integrin agonist.

Contortrostatin binding to αvβ3 results in tyrosine phosphorylation of CAS and FAK—In order to identify the specific proteins that are tyrosine phosphorylated in response to contortrostatin treatment, lysates prepared from contortrostatin-treated cells were subjected to immunoprecipitation with CAS or FAK monoclonal antibodies followed by anti-phosphotyrosine immunoblotting. CAS and FAK were selected as likely candidates based on the similarity of their molecular weights (130 and 125 kDa, respectively) with those observed on the anti-phosphotyrosine immunoblots with whole cell lysates. We found that CAS and FAK are both tyrosine phosphorylated in response to contortrostatin treatment (FIG. 20), and immunoprecipitated CAS and FAK co-migrate with the major bands observed after anti-phosphotyrosine immunoblot with whole cell lysates, indicating that these are the major proteins phosphorylated by contortrostatin treatment.

Figure 23:
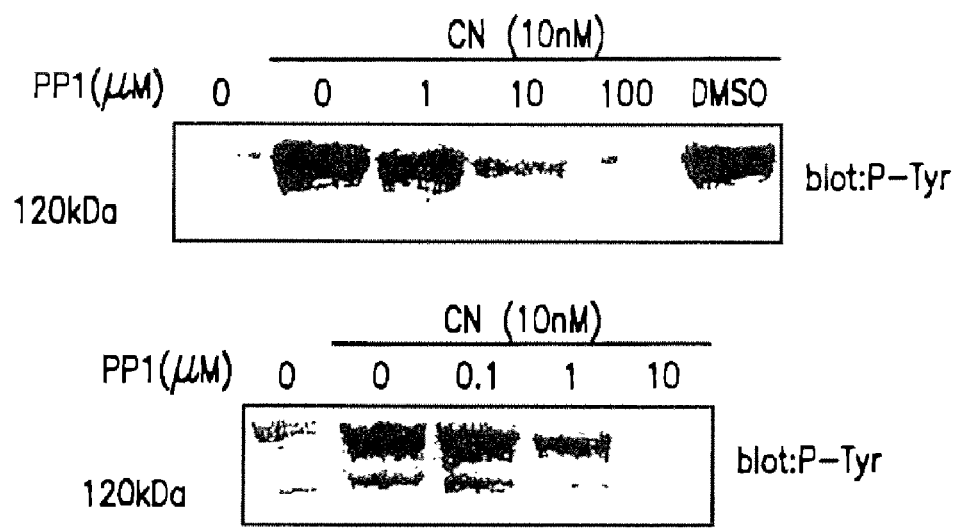
FIG. 23. Involvement of Src family kinases in contortrostatin-induced tyrosine phosphorylation. T24 cells (upper panel) or MDA-MB-435 cells (lower panel) were pretreated with the indicated concentrations of the Src family inhibitor PPI for 30 min prior to stimulation with 10 nM contortrostatin (CN). Lysates were prepared and analyzed by anti-phosphotyrosine immunoblot. Stock solutions of PP I are prepared in DMSO, but DMSO alone had no effect on contortrostatin-induced tyrosine phosphorylation (upper panel).

Src activity is necessary for contortrostatin-induced tyrosine phosphorylation events—The Src tyrosine kinase is known to play a central role in integrin signaling, In order to determine if Src participates in transmitting contortrostatin-induced signals from $\alpha v \beta 3$, T24 cells were pretreated in suspension for 30 min with the Src family inhibitor, PP1 [Hanke, J. H., et al., *J. Biol. Chem.* 271:695-701 (1996)], prior to stimulation with 10 nM contortrostatin. As shown in FIG. 23 (upper panel), PP1 demonstrates a dose-dependent inhibition of tyrosine phosphorylation with complete elimination of contortrostatin-induced signals at a concentration of 100 µM. Similar results were obtained following PP1 treatment of MDA-MB-435 cells, although complete inhibition was achieved at 10 µM PP1 (FIG. 23, lower panel). These findings confirm the involvement of a Src family kinase in integrin signaling stimulated by contortrostatin.

Figure 24:
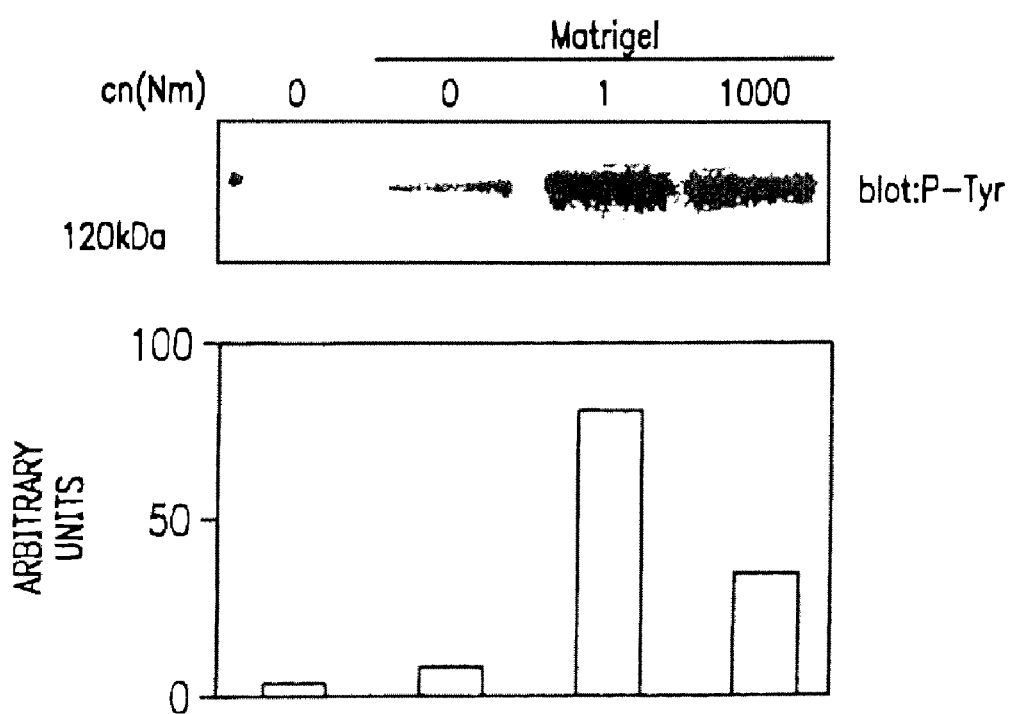
FIG. 24. Contortrostatin-induced tyrosine phosphorylation is independent of cellular adhesion. T24 cells were pretreated with the indicated concentrations of contortrostatin (CN) for 5 min prior to addition to Matrigel-coated plates. Control cells were maintained in suspension. Lysates were prepared after incubating cells on Matrigel for 20 min and analyzed by anti-phosphotyrosine immunoblot (upper panel). The lower panel shows the relative intensity of the corresponding bands as determined by densitometry.

Contortrostatin-induced tyrosine phosphorylation is independent of cellular adhesion—In order to determine if contortrostatin is able to affect tyrosine phosphorylation in adherent cells where integrin ligation and cytoskeletal structure exist, T24 cells were pretreated with contortrostatin before allowing them to adhere to Matrigel-coated plates. It should be noted that contortrostatin does not significantly inhibit cellular binding to laminin. Therefore, contortrostatin does not inhibit cellular binding to Matrigel, which is rich in laminin. Phosphotyrosine immunoblotting revealed that T24 cells showed modest increases in tyrosine phosphorylation after adhesion to Matrigel, but contortrostatin treatment of adherent cells causes a significant additional increase in these signals, including the 120-140 kDa bands shown to contain CAS and FAK (FIG. 24). It was again observed that high concentrations of contortrostatin (1000 nM) generated reduced levels of tyrosine phosphorylation. In similar experiments, T24 cells were allowed to adhere to Matrigel for 30 min prior to treatment with contortrostatin. Following an additional 30 min incubation on Matrigel in the presence of contortrostatin, cells showed similar increased tyrosine phosphorylation of the 120-140 kDa bands. Thus, contortrostatin induction of tyrosine phosphorylation can occur in adherent cells, in the presence of stimuli from ECM proteins, as well as in non-adherent cells.

Contortrostatin causes morphological changes and a breakdown of the actin cytoskeleton and focal adhesion structures—To explore the effects of contortrostatin on cell morphology and cytoskeletal structure, we examined tumor cells under phase contrast microscopy and performed immunocytochemical analysis, focusing our attention on the actin cytoskeleton and focal adhesion structures. Cells were harvested and plated onto glass coverslips coated with Matrigel diluted 1:100 with serum-free medium and blocked with 1% bovine serum albumin (BSA)/phosphate buffered saline (PBS). Cells were incubated overnight at 37° C. Cells were then treated with disintegrins in serum-containing medium or serum-containing medium alone for 30 min at 37° C. Coverslips were washed with PBS, fixed with 4% formaldehyde/PBS for 10 min at 37° C., permeablized with 0.1% Triton X-100/PBS for 1 min and blocked with 1% BSA/PBS for 30 min at 37° C. Coverslips were then incubated with primary antibodies for 1 h at 37° C. followed by fluorescein (FITC)-conjugated secondary antibody plus rhodamine-labeled phalloidin for 1 h. After washing with PBS, coverslips were mounted and images documented on a Olympus AX70 fluorescent microscope equipped with a SPOT digital camera.

In contortrostatin-treated T24 cells adhering to Matrigel, we observed a distinct alteration in cellular morphology where less cell spreading was observed and cells displayed sharp projections from the cell body (FIGS. 25*a* and *b*). We also observed dramatic disruptions in the appearance of the cytoskeleton following 0.5 µM contortrostatin treatment for 30 min in which actin stress fibers present in control cells appeared to collapse (FIGS. 25*c*, *d*, *g* and *h*). Accompanying the cytoskeletal disruptions is a dramatic decrease in the size and number of focal adhesions as shown by phosphotyrosine staining (FIGS. 25*e* and *f*). The subcellular localization of the focal adhesion protein FAK was also examined. In control cells, FAK staining was punctate and displayed a distribution similar to that observed for phosphotyrosine (FIG. 25*i*). In contrast, FAK staining in contortrostatin-treated cells was diffuse and lacked the punctate appearance of control cells (FIG. 25*j*).

Integrin $\alpha v \beta 3$ is required for contortrostatin to disrupt the cytoskeleton and focal adhesions—Disintegrins are known to bind to $\beta 1$ and $\beta 3$ integrins. To test the potential involvement of $\alpha v \beta 3$ in the cytoskeletal disruptions observed after contortrostatin treatment, T24 cells were selected by fluorescence activated cell sorting as described previously (Brooks, P. C., et al.) that lack expression of this integrin and were analyzed by immunocytochemistry. Integrin expression was detected by incubating cells with primary antibodies for 30 min at room temperature. Cells were washed twice with 1% BSA/PBS prior to incubation with FITC-conjugated secondary antibody for 30 min at room temperature. Cells were washed three times prior to analysis on a FACScan flow cytometer (Becton Dickinson, Bedford, Mass.).

Figure 26:
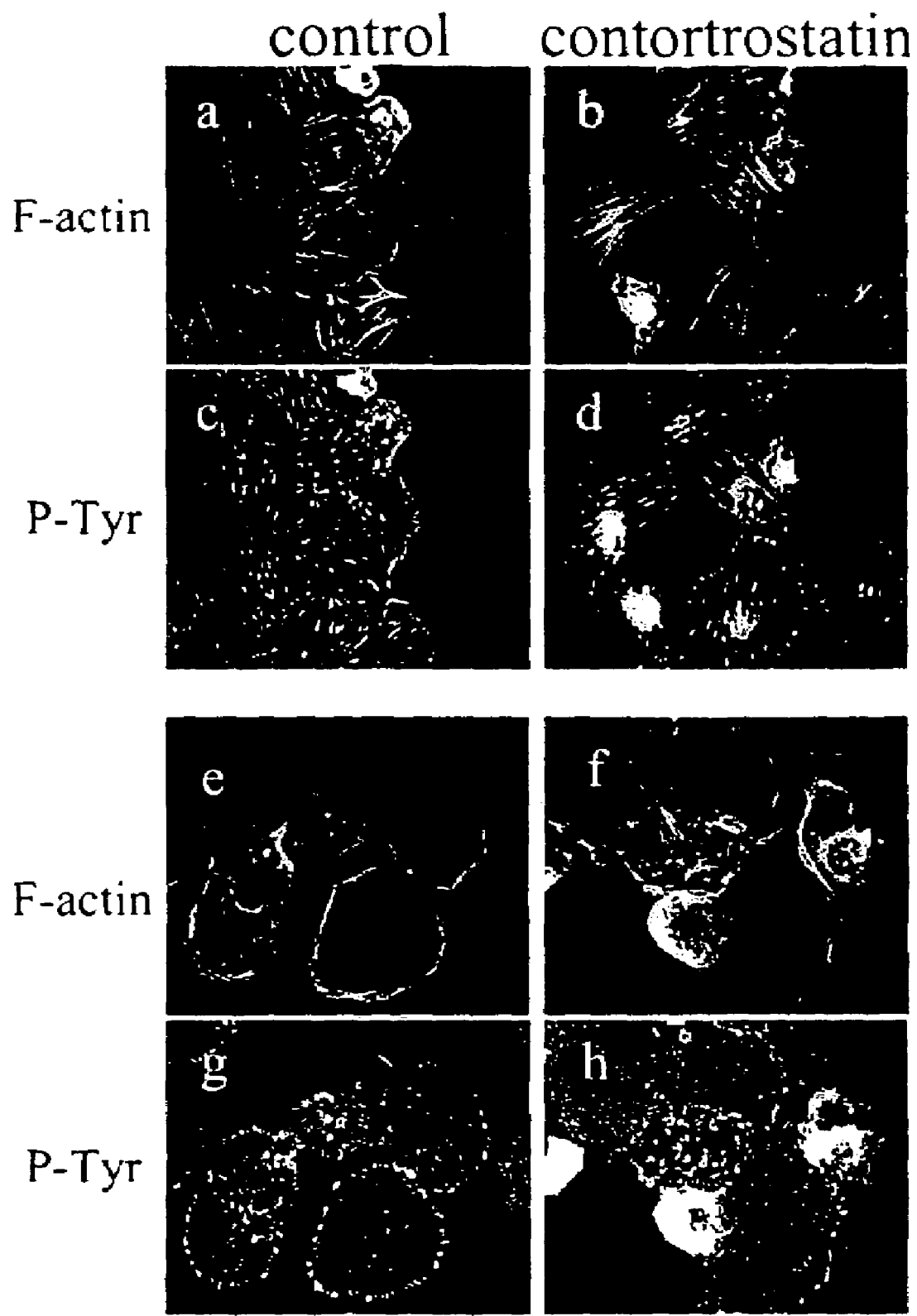
FIG. 26. The presence of the αvβ3 integrin is required for contortrostatin to cause structural disruptions. A subpopulation of T24 cells selected for the absence of αvβ3 (a-d) and OVCAR-5 human ovarian carcinoma cells (e-h) were examined by immunofluorescent microscopy for F-actin and phosphotyrosine. In contrast to αvβ3-expressing cells (FIG. 25) these cells showed no changes in morphology, cytoskeletal or focal adhesion structure after 30 min with 0.5 µM contortrostatin treatment (b, d, f, h) when compared to control cells (a, c, e, g).

Immunofluorescent staining for F-actin and phosphotyrosine was performed as described above. Unlike the $\alpha v \beta 3$-expressing population, T24 cells lacking expression of this integrin showed no alterations in the appearance of the actin cytoskeleton (FIGS. 26*a* and *b*) or focal adhesions (FIGS. 26*c* and *d*) after treatment with 0.5 µM contortrostatin for 30 min. In an extension of these findings, OVCAR-5 human ovarian carcinoma cells, which also lack expression of $\alpha v \beta 3$, similarly showed no cytoskeletal (FIGS. 26*e* and *f*) or focal adhesion alterations (FIGS. 26*g* and *h*) after contortrostatin treatment. These findings indicate that contortrostatin causes structural disruptions exclusively though the $\alpha v \beta 3$ integrin.

Figure 27:
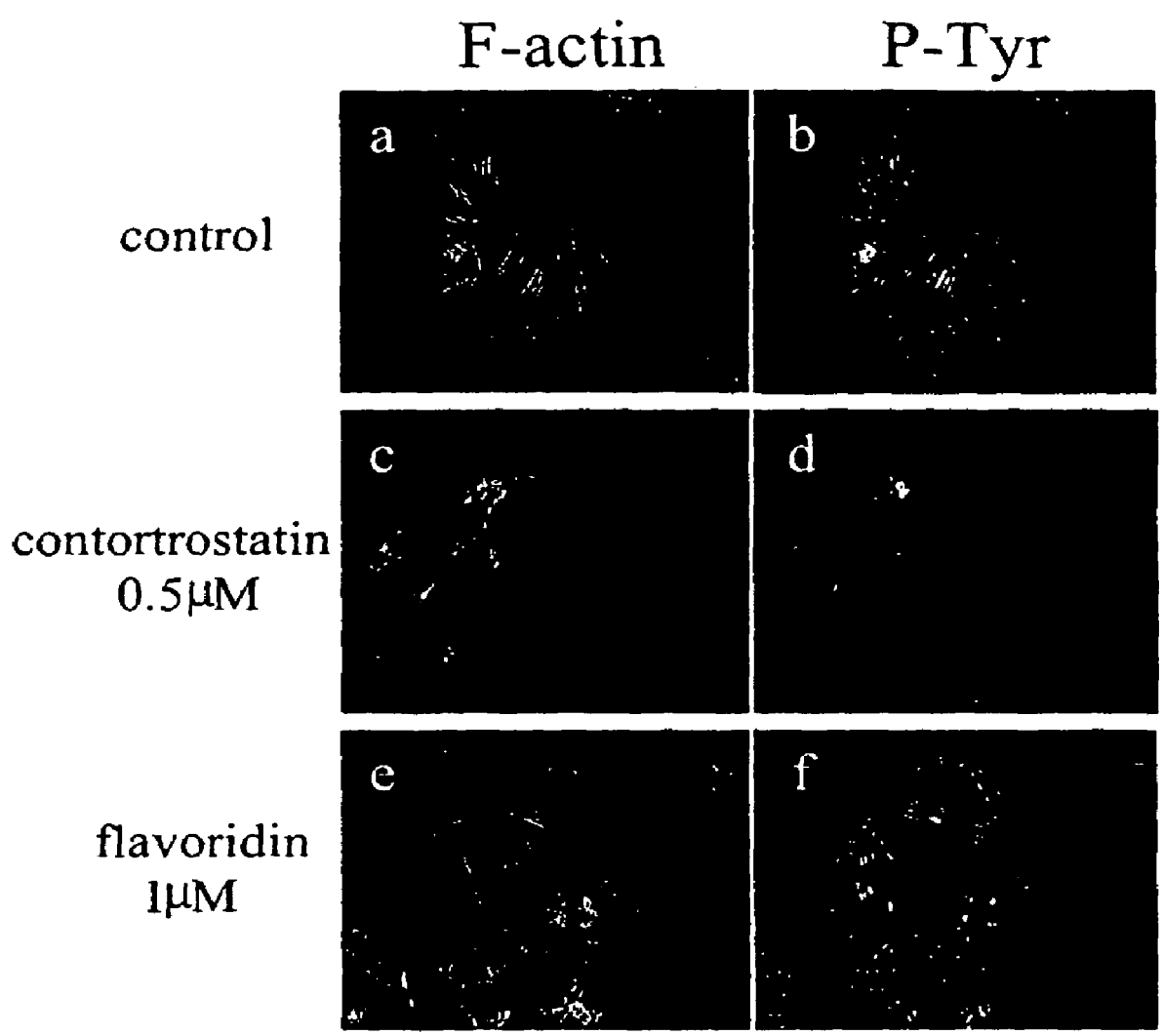
FIG. 27. The monomeric disintegrin flavoridin has no significant effect on the actin cytoskeleton or focal adhesion structure. Contortrostatin was compared directly to the monomeric disintegrin flavoridin for the ability to affect subcellular structures. To equalize the number of integrin-binding RGD motifs present, cells were treated with flavoridin at double the concentration of contortrostatin. While disruptions in F-actin (c) and phosphotyrosine (d) staining are seen after contortrostatin treatment, flavoridin-treated cells (e and f) have an appearance similar to control cells (a and b).

Treatment with a monomeric disintegrin has no effect on cytoskeletal or focal adhesion structure in T24 cells—To determine the role of the homodimeric structure of contortrostatin in inducing cellular disruptions, we directly compared cells treated with the monomeric disintegrin, flavoridin, to those treated with contortrostatin. T24 cells treated with the monomer at 1 µM (FIGS. 27*e* and *f*) had an appearance similar to control cells (FIGS. 27*a* and *b*), while contortrostatin-treated cells (0.5 µM) showed the expected disruptions of the cytoskeleton (FIG. 27*c*) and focal adhesions (FIG. 27*d*). These results were obtained using flavoridin at twice the concentration of contortrostatin, strongly suggesting that the observed disruptions are directly related to the homodimeric structure of contortrostatin.

Figure 28:
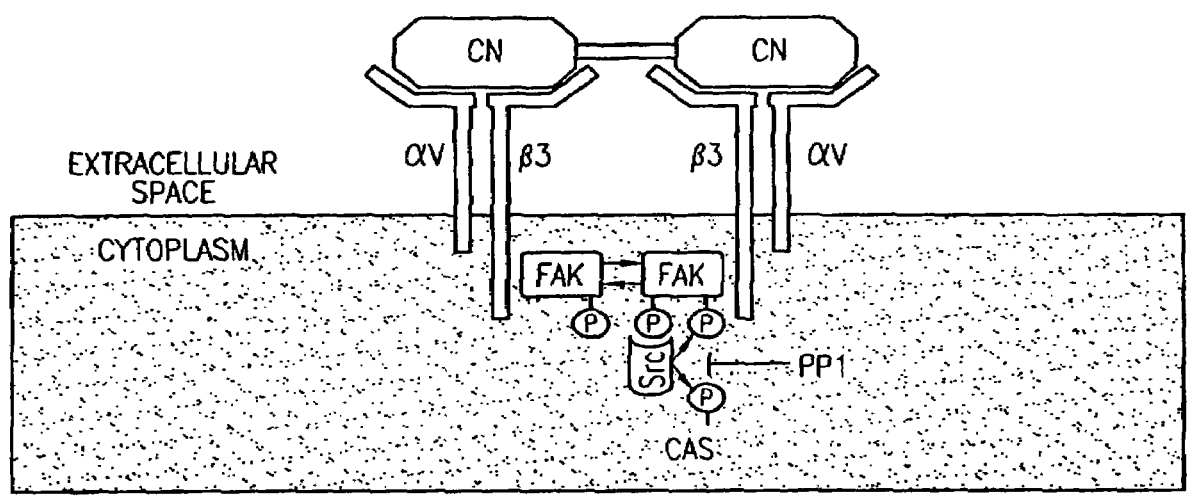
FIG. 28. Schematic representation of the hypothesized mechanism for contortrostatin-induced tyrosine phosphorylation events. The contortrostatin homodimer (CN) binds to two individual αvβ3 at the cell surface. This brings integrin-associated FAK molecules into proximity and allows for trans-autophosphorylation, creating a binding site for Src. Src is then able to phosphoryalate CAS and further phosphorylate FAK. The Src kinase family inhibitor, PP1 is able to block Src-mediated phosphorylation of FAK and CAS.
Figure 29:
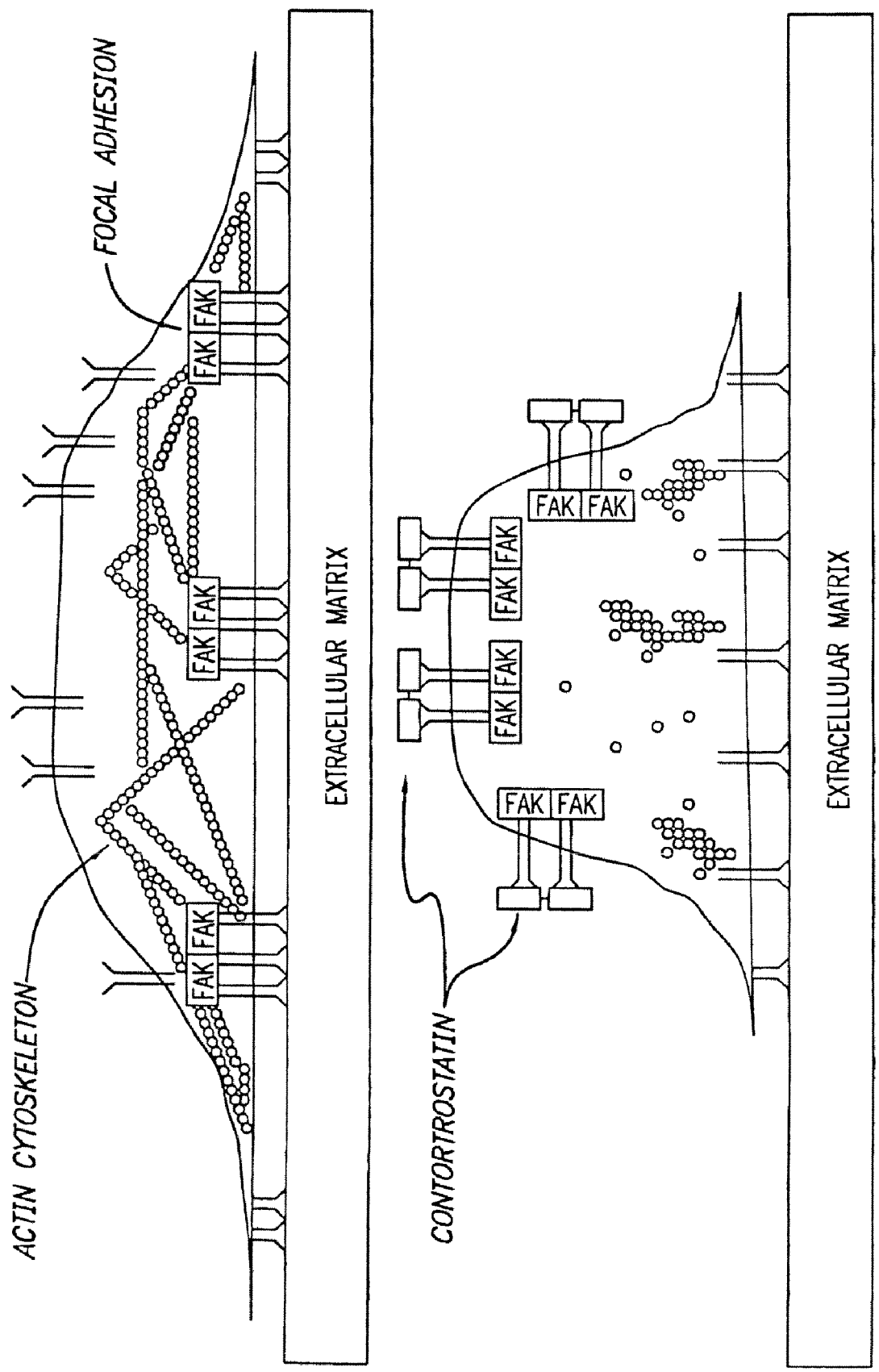
FIG. 29. Schematic representation of hypothesized effects on the cytoskeleton and focal adhesions after contortrostatin treatment. (Top) Untreated cell is well spread with organized actin cytoskeleton and defined focal adhesions. For simplicity, only FAK and integrins are shown in focal adhesions. (Bottom) In the contortrostatin-treated cell, FAK localization is disrupted, focal adhesions undergo disassembly and the actin cytoskeleton collapses, resulting in a change in morphology. These events occur while the cell remains adherent.

Summary:

This example demonstrates that contortrostatin causes massive disruptions in cytoskeletal and focal adhesion structures and induces tyrosine phosphorylation of important focal adhesion proteins. It has recently been suggested that proper regulation of the localization and function of FAK involves cycles of phosphorylation and de-phosphorylation. Contortrostatin might thus be envisioned as upsetting the physiological balance in this cycle where FAK is phosphorylated inappropriately, both temporally and spatially (FIG. 28), causing FAK to adopt a subcellular localization that is incompatible with normal focal adhesion structure (FIG. 29). Apparently, these disruptions extend beyond focal adhesions as it is observed that the actin cytoskeleton is grossly altered as well. Although the molecular details involved are not known, this is not unreasonable since focal adhesion complexes are know to have direct associations with the actin cytoskeleton. Biochemical analysis shows that CAS undergoes tyrosine phosphorylation in cells treated with contortrostatin. CAS localizes to the leading edges of advancing migratory cells, and disruption of this specific localization leads to decreased migratory capacity. It is possible that CAS localization is altered in contortrostatin-treated cells, although we were not able to demonstrate this during these studies since the cells under immunofluorescent observation were not migratory.

A strong link is established between our biochemical results on tyrosine phosphorylation events and the effect of contortrostatin on the cytoskeleton and focal adhesions since the $\alpha v \beta 3$ integrin is required for both processes to occur. Additionally, the monomeric $\alpha v \beta 3$-binding disintegrin flavoridin did not have a significant effect on the actin cytoskeleton or focal adhesions, an observation that correlates well with the biochemical findings that monomeric disintegrins lack the ability to stimulate tyrosine phosphorylation. The lack of activity of the monomeric disintegrin strongly suggests that the unique structure of contortrostatin enables it to stimulate tyrosine phosphorylation events and disrupt cellular infrastructure. There are several reports in the literature describing methods of crosslinking integrins that result in activation of tyrosine phosphorylation [Komberg, L. J., et al. (1991) supra; Bhattacharya, S., et al., (1995) supra; Lipfert, L. et al. *J Cell Biol.* 119:905-912 (1992); and Miyamoto, S. et al., *J. Cell Biol.* 131:791-805 (1995)], but none of these reports explore the effect of these activations on motility. It is likely that contortrostatin stimulates tyrosine phosphorylation by crosslinking $\alpha v \beta 3$ integrins at the cell surface, an activity that would clearly not be found in monomeric disintegrins.

These data identify a novel integrin-mediated mechanism that can have profound effects on $\alpha v \beta 3$-expressing cells. We have shown that contortrostatin causes significant inhibition of motility in tumor cells, and is a more potent inhibitor of motility in $\alpha v \beta 3$-expressing cells than monovalent integrin antagonists. It is also possible that contortrostatin may have a negative effect on cell division since this process also depends on proper regulation of FAK and the actin cytoskeleton although this possibility has not been investigated. These findings have significance to angiogenesis since the $\alpha v \beta 3$ integrin has been shown to have increased expression on angiogenic endothelial cells and to be critical to regulating this process. Thus, by passively blocking the binding of $\alpha v \beta 3$ to its physiological ligand and actively inducing inappropriate signals leading to massive structural disruptions within the cell, contortrostatin is expected to be an effective inhibitor of angiogenesis. These findings suggest an alternative approach to halt tumor cell invasion and metastasis as well as angiogenesis by active disruption of signaling pathways rather than blockage with signaling inhibitors, and identify contortrostatin as a prototype agent to further explore the potential of this approach.

In conclusion, this work identifies activity novel to the disintegrin family through which integrin signaling can be modulated in tumor cells. This activity appears to be unique to contortrostatin, as three other disintegrins have been found to lack the ability to stimulate tyrosine phosphorylation (Clark et al., supra). Recently, a number of new dimeric disintegrins have been purified from various snake venom (Marcinkiewicz et al., supra). It is unlikely that these molecules would demonstrate activity similar to contortrostatin because they are heterodimers lacking the RGD sequence, and they do not appear to interact with $\alpha v \beta 3$. Our report identifies contortrostatin as a useful reagent for the further study of $\alpha v \beta 3$ function, and identifies a novel integrin-mediated mechanism that may negatively effect tumor cell motility. We propose that the combined effects of blocking the binding of $\alpha v \beta 5$, $\alpha 5 \beta 1$ and $\alpha v \beta 3$ to the ECM and the initiation of inappropriate signals leading to hyperphosphorylation of critical signaling molecules can lead to immobilization of otherwise motile and invasive tumor cells.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A homodimeric disintegrin comprising an amino acid sequence which is at least 90% percent identical to amino acid numbers 419 to 483 of SEQ ID NO: 2, wherein said contortrostatin amino acid sequence (i) binds to integrin αvβ5 and (ii) induces αvβ5-mediated tyrosine phosphorylation of CAS and FAK in tumor cells.

2. The homodimeric disintegrin of claim 1 having an amino acid sequence selected from the group consisting of:

(a) amino acid numbers 419 to 483 of SEQ ID NO: 2;

(b) an amino sequence at least 95% identical to (a) as determined by FASTA or BLAST using default opening an gap penalties and a default scoring matrix.

3. A pharmaceutically acceptable composition comprising a pharmaceutically acceptable carrier and a homodimeric disintegrin according to claim 1.

* * * * *

SEQUENCE LISTING

```
<160> NUMBER OF SEQ ID NOS: 15

<210> SEQ ID NO 1
<211> LENGTH: 2029
<212> TYPE: DNA
<213> ORGANISM: Agkistrodon contortrix

<400> SEQUENCE: 1
gaattcgggg tcaatagagg aagagctcaa gttggcttga aagcaggaag agattgcctg      60
tcttccagcc aaatccagcc gccaaaatga tccaggttct cttggtgact ctatgcttag     120
cagcttttcc ttatcaaggg agctctataa tcctggaatc tgggaatgtt aatgattatg     180
aagtactgta tccacaaaaa gtcactgcat tgcccaaagg agcagttcag ccaaagtatg     240
```

```
aagacaccat gcaatatgaa tttaaagtga atggagagcc agtggtcctt cacctggaaa    300
aaaataaagg actttttttca aaagattaca gcgagactca ttattcctct gatggcagaa    360
aaattacaac aaaccctccg gttgaggatc actgctatta tcatggacgc atccagaatg    420
atgctgactc aactgcaagc atcagtgcat gcaacggttt gaaggacat tcaagcttc     480
aaggggagac gtaccttatt gaaccccttga agctttccga cagtgaagcc catgcagtct    540
acaaatatga aaacgtagaa aagaagatg aggcccccaa aatgtgtggg gtaacccaga    600
ctaattggga atcagatgag cccatcaaaa aggcctctca gttaaatctt actcctgaac    660
aacaaggatt ccccccaaaga tacattgagc ttgttgtagt tgcagatcac agaatgttca    720
cgaaatacaa cggcaattta aatactatta gaatatgggt acatgaactt gtcaacacta    780
tgaatgtgtt ttacagacct ttgaatattc gtgtctcact gactgaccta aagtttggt    840
cagaccaaga tttgatcaac gtgcagccag cagcggctga tactttggaa gcatttggag    900
actggagaga gacagtcttg ctgaatcgca taagtcatga taatgctcag ttactcacgg    960
ccattgagct tgatggagaa actataggat tggctaacag gggcaccatg tgcgacccga   1020
agctttctac aggaattgtt caggatcata gtgcaataaa tctttgggtt gcagttacaa   1080
tgccccatga gatgggtcat aatctgggta ttagtcacga tggaaatcag tgtcattgcg   1140
atgctaactc atgcattatg agtgaagaac taagagaaca acttttcctt gagttcagcg   1200
attgtagtca gaatcaatat cagacatatc ttactgatca taaccccacaa tgcatgctca   1260
atgaaccctt gagaacagat attgttttcaa ctccagtttc tggaaatgaa cttttggaga   1320
cgggagaaga aagtgacttt gacgctcctg caaatccgtg ctgcgatgct gcaacatgta   1380
aactgacaac agggtcacag tgtgcagatg gactgtgttg tgaccagtgc aaatttatga   1440
agaaggaac agtatgccgg agagcaaggg gtgatgacct ggatgattac tgcaatggca   1500
tatctgctgg ctgtcccaga aatcccttcc atgcctaacc aacaatggag atggaatggt   1560
ctgcagcaac aggcagtgtg ttgatctgaa tacagcctaa taatcaacct ctggcttctc   1620
tcagatttga tcatggagat ccttcttcca gaaggtttca cttccctcaa atccaaagag   1680
acccatctgc ctgcatccta ctagtaaatc accccttagct tccagatggt atccaaattc   1740
tgtaatatttt cttctccata tttaatctat ttaccttttg ctgtaacaaa accttttttcc   1800
tgtcacaaag ctccatgggc atgtacagct tatctgctgt caagaaaaaa aatggccatt   1860
ttaccgtttg ccagttacaa agcacattta atgcaacaag ttcttccttt tgagctgatg   1920
tattcaaagt caatgcttcc tctcccaaaa tttcatgctg gcttcccaag atgtagctgc   1980
ttccgtcaat aaacaaacta ttctcattca aaaaaaaaaa cccgaattc              2029
```

<210> SEQ ID NO 2
<211> LENGTH: 483
<212> TYPE: PRT
<213> ORGANISM: Agkistrodon contortrix

<400> SEQUENCE: 2

Met Ile Gln Val Leu Leu Val Thr Leu Cys Leu Ala Ala Phe Pro Tyr
1               5                   10                  15

Gln Gly Ser Ser Ile Ile Leu Glu Ser Gly Asn Val Asn Asp Tyr Glu
            20                  25                  30

Val Leu Tyr Pro Gln Lys Val Thr Ala Leu Pro Lys Gly Ala Val Gln
        35                  40                  45

Pro Lys Tyr Glu Asp Thr Met Gln Tyr Glu Phe Lys Val Asn Gly Glu

-continued

```
            50                  55                  60
Pro Val Val Leu His Leu Glu Lys Asn Lys Gly Leu Phe Ser Lys Asp
65                  70                  75                  80

Tyr Ser Glu Thr His Tyr Ser Ser Asp Gly Arg Lys Ile Thr Thr Asn
                85                  90                  95

Pro Pro Val Glu Asp His Cys Tyr Tyr His Gly Arg Ile Gln Asn Asp
            100                 105                 110

Ala Asp Ser Thr Ala Ser Ile Ser Ala Cys Asn Gly Leu Lys Gly His
                115                 120                 125

Phe Lys Leu Gln Gly Glu Thr Tyr Leu Ile Glu Pro Leu Lys Leu Ser
130                 135                 140

Asp Ser Glu Ala His Ala Val Tyr Lys Tyr Glu Asn Val Glu Lys Glu
145                 150                 155                 160

Asp Glu Ala Pro Lys Met Cys Gly Val Thr Gln Thr Asn Trp Glu Ser
                165                 170                 175

Asp Glu Pro Ile Lys Lys Ala Ser Gln Leu Asn Leu Thr Pro Glu Gln
            180                 185                 190

Gln Gly Phe Pro Gln Arg Tyr Ile Glu Leu Val Val Val Ala Asp His
                195                 200                 205

Arg Met Phe Thr Lys Tyr Asn Gly Asn Leu Asn Thr Ile Arg Ile Trp
210                 215                 220

Val His Glu Leu Val Asn Thr Met Asn Val Phe Tyr Arg Pro Leu Asn
225                 230                 235                 240

Ile Arg Val Ser Leu Thr Asp Leu Glu Val Trp Ser Asp Gln Asp Leu
                245                 250                 255

Ile Asn Val Gln Pro Ala Ala Ala Asp Thr Leu Glu Ala Phe Gly Asp
            260                 265                 270

Trp Arg Glu Thr Val Leu Leu Asn Arg Ile Ser His Asp Asn Ala Gln
                275                 280                 285

Leu Leu Thr Ala Ile Glu Leu Asp Gly Glu Thr Ile Gly Leu Ala Asn
290                 295                 300

Arg Gly Thr Met Cys Asp Pro Lys Leu Ser Thr Gly Ile Val Gln Asp
305                 310                 315                 320

His Ser Ala Ile Asn Leu Trp Val Ala Val Thr Met Ala His Glu Met
                325                 330                 335

Gly His Asn Leu Gly Ile Ser His Asp Gly Asn Gln Cys His Cys Asp
            340                 345                 350

Ala Asn Ser Cys Ile Met Ser Glu Glu Leu Arg Glu Gln Leu Ser Phe
                355                 360                 365

Glu Phe Ser Asp Cys Ser Gln Asn Gln Tyr Gln Thr Tyr Leu Thr Asp
370                 375                 380

His Asn Pro Gln Cys Met Leu Asn Glu Pro Leu Arg Thr Asp Ile Val
385                 390                 395                 400

Ser Thr Pro Val Ser Gly Asn Glu Leu Leu Glu Thr Gly Glu Glu Ser
                405                 410                 415

Asp Phe Asp Ala Pro Ala Asn Pro Cys Cys Asp Ala Ala Thr Cys Lys
            420                 425                 430

Leu Thr Thr Gly Ser Gln Cys Ala Asp Gly Leu Cys Cys Asp Gln Cys
                435                 440                 445

Lys Phe Met Lys Glu Gly Thr Val Cys Arg Arg Ala Arg Gly Asp Asp
            450                 455                 460

Leu Asp Asp Tyr Cys Asn Gly Ile Ser Ala Gly Cys Pro Arg Asn Pro
465                 470                 475                 480
```

Phe His Ala

<210> SEQ ID NO 3
<211> LENGTH: 21
<212> TYPE: DNA
<213> ORGANISM: Trimeresurus gramineus

<400> SEQUENCE: 3
gtttacaggt tgcagcatcg c         21

<210> SEQ ID NO 4
<211> LENGTH: 21
<212> TYPE: DNA
<213> ORGANISM: Trimeresurus gramineus

<400> SEQUENCE: 4
gcgatgctgc aacctgtaaa c         21

<210> SEQ ID NO 5
<211> LENGTH: 21
<212> TYPE: DNA
<213> ORGANISM: Bacteriophage lambda

<400> SEQUENCE: 5
gcgatgctgc aacctgtaaa c         21

<210> SEQ ID NO 6
<211> LENGTH: 24
<212> TYPE: DNA
<213> ORGANISM: Bacteriophaeg Lambda gt10

<400> SEQUENCE: 6
cttatgagta tttcttccag ggta       24

<210> SEQ ID NO 7
<211> LENGTH: 71
<212> TYPE: PRT
<213> ORGANISM: Agkistrodon piscivorus

<400> SEQUENCE: 7

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Lys Phe Met Lys Glu Gly Thr Val Cys Arg
        35                  40                  45

Ala Arg Gly Asp Asp Val Asn Asp Tyr Cys Asn Gly Ile Ser Ala Gly
    50                  55                  60

Cys Pro Arg Asn Pro Phe His
65                  70

<210> SEQ ID NO 8
<211> LENGTH: 552
<212> TYPE: PRT
<213> ORGANISM: Trimeresurus gramineus

<400> SEQUENCE: 8

Glu Ala Gly Glu Asp Cys Asp Cys Gly Ser Pro Ala Asn Pro Cys Cys
1               5                   10                  15

Asp Ala Ala Thr Cys Lys Leu Ile Pro Gly Ala Gln Cys Gly Glu Gly
            20                  25                  30

```
Leu Cys Cys Asp Gln Cys Ser Phe Ile Glu Glu Gly Thr Val Cys Arg
         35                  40                  45

Ile Ala Arg Gly Asp Asp Leu Asp Asp Tyr Cys Asn Gly Arg Ser Ala
     50                  55                  60

Gly Cys Pro Arg Asn Pro Phe His Met Ile Gln Val Leu Leu Ile Thr
 65                  70                  75                  80

Ile Cys Leu Ala Val Phe Pro Tyr Gln Gly Ser Ser Ile Ile Leu Glu
                 85                  90                  95

Ser Gly Asn Leu Asn Asp Tyr Glu Val Val Tyr Pro Glu Lys Val Thr
             100                 105                 110

Ala Leu Pro Lys Gly Ala Val Gln Gln Lys Tyr Glu Asp Ala Met Gln
         115                 120                 125

Tyr Glu Phe Lys Val Asn Gly Glu Pro Val Val Leu His Leu Glu Lys
     130                 135                 140

Asn Lys Gly Leu Phe Ser Glu Asp Tyr Ser Glu Ile His Tyr Ser Pro
145                 150                 155                 160

Asp Gly Arg Glu Ile Thr Ala Tyr Pro Ser Val Glu Asp His Cys Tyr
                 165                 170                 175

Tyr His Gly Arg Ile Glu Asn Asp Ala Asp Ser Thr Ala Ser Ile Ser
             180                 185                 190

Ala Cys Asp Gly Leu Lys Gly His Phe Lys Leu Gln Gly Glu Met Tyr
         195                 200                 205

Leu Ile Glu Pro Leu Glu Leu Ser Asp Ser Glu Ala His Ala Val Phe
     210                 215                 220

Lys Tyr Glu Asn Val Glu Lys Glu Asp Glu Pro Pro Lys Met Cys Gly
225                 230                 235                 240

Val Thr Gln Asn Trp Glu Ser Tyr Glu Ser Thr Lys Lys Ala Ser Gln
                 245                 250                 255

Leu Asn Val Thr Pro Glu Gln Gln Arg Phe Pro Gln Arg Tyr Ile Lys
             260                 265                 270

Leu Gly Ile Phe Val Asp His Gly Met Tyr Thr Lys Tyr Ser Gly Asn
         275                 280                 285

Ser Glu Arg Ile Thr Lys Arg Val His Gln Met Ile Asn Asn Ile Asn
     290                 295                 300

Met Met Cys Arg Ala Leu Asn Ile Val Thr Thr Leu Ser Val Leu Glu
305                 310                 315                 320

Ile Trp Ser Glu Lys Asp Leu Ile Thr Val Gln Ala Ser Ala Pro Thr
                 325                 330                 335

Thr Leu Thr Leu Phe Gly Ala Trp Arg Glu Thr Val Leu Leu Asn Arg
             340                 345                 350

Thr Ser His Asp His Ala Gln Leu Leu Thr Ala Thr Ile Phe Asn Gly
         355                 360                 365

Asn Val Ile Gly Arg Ala Pro Val Gly Gly Met Cys Asp Pro Lys Arg
     370                 375                 380

Ser Val Ala Ile Val Arg Asp His Asn Ala Ile Val Phe Val Val Ala
385                 390                 395                 400

Val Thr Met Thr His Glu Met Gly His Asn Leu Gly Met His His Asp
                 405                 410                 415

Glu Asp Lys Cys Asn Cys Asn Thr Cys Ile Met Ser Lys Val Leu Ser
             420                 425                 430

Arg Gln Pro Ser Lys Tyr Phe Ser Glu Cys Ser Lys Asp Tyr Tyr Gln
         435                 440                 445
```

-continued

```
Thr Phe Leu Thr Asn His Asn Pro Gln Cys Ile Leu Asn Ala Pro Leu
    450                 455                 460

Arg Thr Asp Thr Val Ser Thr Pro Val Ser Gly Asn Glu Leu Leu Glu
465                 470                 475                 480

Ala Gly Glu Asp Cys Asp Cys Gly Ser Pro Ala Asn Pro Cys Cys Asp
                485                 490                 495

Ala Ala Thr Cys Lys Leu Ile Pro Gly Ala Gln Cys Gly Glu Gly Leu
                500                 505                 510

Cys Cys Asp Gln Cys Ser Phe Ile Glu Glu Gly Thr Val Cys Arg Ile
                515                 520                 525

Ala Arg Gly Asp Asp Leu Asp Asp Tyr Cys Asn Gly Arg Ser Ala Gly
                530                 535                 540

Cys Pro Arg Asn Pro Phe His Ala
545                 550
```

<210> SEQ ID NO 9
<211> LENGTH: 73
<212> TYPE: PRT
<213> ORGANISM: Trimeresurus albolabris

<400> SEQUENCE: 9

```
Glu Ala Gly Glu Asp Cys Asp Cys Gly Ser Pro Ala Asn Pro Cys Cys
1               5                   10                  15

Asp Ala Ala Thr Cys Lys Leu Leu Pro Gly Ala Gln Cys Gly Glu Gly
                20                  25                  30

Leu Cys Cys Asp Gln Cys Ser Phe Met Lys Lys Gly Thr Ile Cys Arg
            35                  40                  45

Arg Ala Arg Gly Asp Asp Leu Asp Asp Tyr Cys Asn Gly Ile Ser Ala
        50                  55                  60

Gly Cys Pro Arg Asn Pro Leu His Ala
65                  70
```

<210> SEQ ID NO 10
<211> LENGTH: 73
<212> TYPE: PRT
<213> ORGANISM: Trimeresurus elegans

<400> SEQUENCE: 10

```
Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Asp Gly
                20                  25                  30

Leu Cys Cys Asp Gln Cys Arg Phe Lys Lys Lys Arg Thr Ile Cys Arg
            35                  40                  45

Arg Ala Arg Gly Asp Asn Pro Asp Arg Cys Thr Gly Gln Ser Ala
        50                  55                  60

Asp Cys Pro Arg Asn Gly Leu Tyr Ser
65                  70
```

<210> SEQ ID NO 11
<211> LENGTH: 68
<212> TYPE: PRT
<213> ORGANISM: Calloselasma rhodostoma

<400> SEQUENCE: 11

```
Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
```

-continued

```
                    20                  25                  30
Cys Glu Gln Cys Lys Phe Asp Arg Ala Gly Lys Ile Cys Arg Ile Pro
            35                  40                  45
Arg Gly Asp Met Pro Asp Arg Cys Thr Gly Gln Ser Ala Asp Cys
        50                  55                  60
Pro Arg Tyr His
65

<210> SEQ ID NO 12
<211> LENGTH: 606
<212> TYPE: PRT
<213> ORGANISM: Crotalus atrox

<400> SEQUENCE: 12

Met Ile Gln Val Leu Leu Val Thr Ile Cys Leu Ala Ala Phe Pro Tyr
1               5                   10                  15

Gln Gly Ser Ser Ile Ile Leu Glu Ser Gly Asn Val Asn Asp Tyr Glu
            20                  25                  30

Val Ile Tyr Pro Arg Lys Val Thr Ala Leu Pro Lys Gly Ala Val Gln
        35                  40                  45

Pro Lys Tyr Glu Asp Ala Met Gln Tyr Glu Leu Lys Val Asn Gly Glu
    50                  55                  60

Pro Val Val Leu His Leu Gly Lys Asn Lys Gly Leu Phe Ser Lys Asp
65                  70                  75                  80

Tyr Ser Glu Thr His Tyr Ser Pro Asp Gly Arg Glu Ile Thr Thr Tyr
                85                  90                  95

Pro Leu Val Glu Asp His Cys Tyr Tyr His Gly Ile Glu Asn Asp Ala
            100                 105                 110

Asp Ser Thr Ala Ser Ile Ser Ala Cys Asn Gly Leu Lys Gly His Phe
        115                 120                 125

Lys Leu Gln Gly Glu Met Tyr Leu Ile Glu Pro Leu Lys Leu Pro Asp
    130                 135                 140

Ser Glu Ala His Ala Val Tyr Lys Tyr Glu Asn Val Glu Lys Glu Asp
145                 150                 155                 160

Glu Ala Leu Lys Met Cys Gly Val Thr Gln Asn Trp Glu Ser Tyr Glu
                165                 170                 175

Pro Ile Lys Lys Ala Ser Gln Leu Val Val Thr Ala Glu His Gln Lys
            180                 185                 190

Tyr Asn Pro Phe Arg Phe Val Glu Leu Phe Leu Val Val Asp Lys Ala
        195                 200                 205

Met Val Thr Lys Asn Asn Gly Asp Leu Asp Lys Ile Lys Thr Arg Met
    210                 215                 220

Tyr Glu Ile Val Asn Thr Val Asn Glu Ile Tyr Arg Tyr Met Tyr Ile
225                 230                 235                 240

His Val Ala Leu Val Gly Leu Glu Ile Trp Ser Asn Glu Asp Lys Ile
                245                 250                 255

Thr Val Lys Pro Glu Ala Gly Tyr Thr Leu Asn Ala Phe Gly Glu Trp
            260                 265                 270

Arg Lys Thr Asp Leu Leu Thr Arg Lys Lys His Asp Asn Ala Gln Leu
        275                 280                 285

Leu Thr Ala Ile Asp Leu Asp Arg Val Ile Gly Leu Ala Tyr Val Gly
    290                 295                 300

Ser Met Cys His Pro Lys Arg Ser Thr Gly Ile Ile Gln Asp Tyr Ser
305                 310                 315                 320
```

```
Glu Ile Asn Leu Val Val Ala Val Ile Met Ala His Glu Met Gly His
                325                 330                 335

Asn Leu Gly Ile Asn His Asp Ser Gly Tyr Cys Ser Cys Gly Asp Tyr
                340                 345                 350

Ala Cys Ile Met Arg Pro Glu Ile Ser Pro Glu Pro Ser Thr Phe Phe
                355                 360                 365

Ser Asn Cys Ser Tyr Phe Glu Cys Trp Asp Phe Ile Met Asn His Asn
            370                 375                 380

Pro Glu Cys Ile Leu Asn Glu Pro Leu Gly Thr Asp Ile Ile Ser Pro
385                 390                 395                 400

Pro Val Cys Gly Asn Glu Leu Leu Glu Val Gly Glu Glu Cys Asp Cys
                405                 410                 415

Gly Thr Pro Glu Asn Cys Gln Asn Glu Cys Cys Asp Ala Ala Thr Cys
                420                 425                 430

Lys Leu Lys Ser Gly Ser Gln Cys Gly His Gly Asp Cys Cys Glu Gln
                435                 440                 445

Cys Lys Phe Ser Lys Ser Gly Thr Glu Cys Arg Ala Ser Met Glu Cys
            450                 455                 460

Asp Pro Ala Glu His Cys Thr Gly Gln Ser Ser Glu Cys Pro Ala Asp
465                 470                 475                 480

Val Phe His Lys Asn Gly Gln Pro Cys Leu Asp Asn Tyr Gly Tyr Cys
                485                 490                 495

Tyr Asn Gly Asn Cys Pro Ile Met Tyr His Gln Cys Tyr Asp Leu Phe
                500                 505                 510

Gly Ala Asp Val Tyr Glu Ala Glu Asp Ser Cys Phe Glu Arg Asn Gln
            515                 520                 525

Lys Gly Asn Tyr Tyr Gly Tyr Cys Arg Lys Glu Asn Gly Asn Lys Ile
            530                 535                 540

Pro Cys Ala Pro Glu Asp Val Lys Cys Gly Arg Leu Tyr Cys Lys Asp
545                 550                 555                 560

Asn Ser Pro Gly Asn Asn Pro Cys Lys Met Glu Tyr Ser Asn Glu Asp
                565                 570                 575

Glu His Lys Gly Met Val Leu Pro Gly Thr Lys Cys Ala Asp Gly Lys
                580                 585                 590

Val Cys Ser Asn Gly His Cys Val Asp Val Ala Thr Ala Tyr
            595                 600                 605

<210> SEQ ID NO 13
<211> LENGTH: 571
<212> TYPE: PRT
<213> ORGANISM: Bothrops jararaca

<400> SEQUENCE: 13

Ala Thr Arg Pro Lys Gly Ala Val Gln Pro Lys Tyr Glu Asp Ala Met
1               5                   10                  15

Gln Tyr Glu Phe Lys Val Asn Gly Glu Pro Val Val Leu His Leu Glu
                20                  25                  30

Lys Asn Lys Gly Leu Phe Ser Lys Asp Tyr Ser Glu Ile His Tyr Ser
            35                  40                  45

Pro Asp Gly Arg Glu Ile Thr Thr Tyr Pro Pro Val Glu Asp His Cys
        50                  55                  60

Tyr Tyr His Gly Arg Ile Glu Asn Asp Ala Asp Ser Thr Ala Ser Ile
65                  70                  75                  80

Ser Ala Cys Asn Gly Leu Lys Gly Tyr Phe Lys Leu Gln Arg Glu Thr
                85                  90                  95
```

-continued

```
Tyr Phe Ile Glu Pro Leu Lys Leu Pro Asp Ser Glu Ala His Ala Val
            100                 105                 110

Phe Lys Tyr Glu Asn Val Glu Lys Glu Asp Glu Ala Pro Lys Met Cys
        115                 120                 125

Gly Val Thr Gln Asn Trp Lys Ser Tyr Glu Pro Ile Lys Lys Ala Ser
        130                 135                 140

Gln Leu Ala Phe Thr Ala Glu Gln Gln Arg Tyr Asp Pro Tyr Lys Tyr
145                 150                 155                 160

Ile Glu Phe Phe Val Val Asp Gln Gly Thr Val Thr Lys Asn Asn
                165                 170                 175

Gly Asp Leu Asp Lys Ile Lys Ala Arg Met Tyr Glu Leu Ala Asn Ile
            180                 185                 190

Val Asn Glu Ile Phe Arg Tyr Leu Tyr Met His Val Ala Leu Val Gly
        195                 200                 205

Leu Glu Ile Trp Ser Asn Gly Asp Lys Ile Thr Val Lys Pro Asp Val
        210                 215                 220

Asp Tyr Thr Leu Asn Ser Phe Ala Glu Trp Arg Lys Thr Asp Leu Leu
225                 230                 235                 240

Thr Arg Lys Lys His Asp Asn Ala Gln Leu Leu Thr Ala Ile Asp Phe
                245                 250                 255

Asn Gly Pro Thr Ile Phe Tyr Ala Tyr Ile Gly Ser Met Cys His Pro
            260                 265                 270

Lys Arg Ser Val Gly Ile Val Gln Asp Tyr Ser Pro Ile Asn Leu Val
        275                 280                 285

Val Ala Val Ile Met Ala His Glu Met Gly His Asn Leu Gly Ile His
        290                 295                 300

His Asp Thr Gly Ser Cys Ser Cys Gly Asp Tyr Pro Cys Ile Met Gly
305                 310                 315                 320

Pro Thr Ile Ser Asn Glu Pro Ser Lys Phe Phe Ser Asn Cys Ser Tyr
                325                 330                 335

Ile Gln Cys Trp Asp Phe Ile Met Asn His Asn Pro Glu Cys Ile Ile
            340                 345                 350

Asn Glu Pro Leu Gly Thr Asp Ile Ile Ser Pro Pro Val Cys Gly Asn
        355                 360                 365

Glu Leu Leu Glu Val Gly Glu Glu Cys Asp Cys Gly Thr Pro Glu Asn
        370                 375                 380

Cys Gln Asn Glu Cys Cys Asp Ala Ala Thr Cys Lys Leu Lys Ser Gly
385                 390                 395                 400

Ser Gln Cys Gly His Gly Asp Cys Cys Glu Gln Cys Lys Phe Ser Lys
                405                 410                 415

Ser Gly Thr Glu Cys Arg Ala Ser Met Ser Glu Cys Asp Pro Ala Glu
            420                 425                 430

His Cys Thr Gly Gln Ser Ser Glu Cys Pro Ala Asp Val Phe His Lys
        435                 440                 445

Asn Gly Gln Pro Cys Leu Asp Asn Tyr Gly Tyr Cys Tyr Asn Gly Asn
450                 455                 460

Cys Pro Ile Met Tyr His Gln Cys Tyr Ala Leu Phe Gly Ala Asp Val
465                 470                 475                 480

Tyr Glu Ala Glu Asp Ser Cys Phe Lys Asp Asn Gln Lys Gly Asn Tyr
                485                 490                 495

Tyr Gly Tyr Cys Arg Lys Glu Asn Gly Lys Lys Ile Pro Cys Ala Pro
            500                 505                 510
```

```
Glu Asp Val Lys Cys Gly Arg Leu Tyr Cys Lys Asp Asn Ser Pro Gly
            515                 520                 525

Gln Asn Asn Pro Cys Lys Met Phe Tyr Ser Asn Asp Asp Glu His Lys
        530                 535                 540

Gly Met Val Leu Pro Gly Thr Lys Cys Ala Asp Gly Lys Val Cys Ser
545                 550                 555                 560

Asn Gly His Cys Val Asp Val Ala Thr Ala Tyr
                565                 570

<210> SEQ ID NO 14
<211> LENGTH: 478
<212> TYPE: PRT
<213> ORGANISM: Crotalus atrox

<400> SEQUENCE: 14

Met Ile Gln Val Leu Leu Val Thr Ile Cys Leu Ala Ala Phe Pro Tyr
1               5                   10                  15

Gln Gly Ser Ser Ile Ile Leu Glu Ser Gly Asn Val Asn Asp Tyr Glu
            20                  25                  30

Val Ile Tyr Pro Arg Lys Val Thr Ala Leu Pro Lys Gly Ala Val Gln
        35                  40                  45

Pro Lys Tyr Glu Asp Thr Met Gln Tyr Glu Leu Lys Val Asn Gly Glu
    50                  55                  60

Pro Val Val Leu His Leu Glu Lys Asn Lys Gly Leu Phe Ser Lys Asp
65                  70                  75                  80

Tyr Ser Glu Thr His Tyr Ser Phe Asp Gly Arg Lys Ile Thr Thr Asn
                85                  90                  95

Pro Ser Val Glu Asp His Cys Tyr Tyr His Gly Arg Ile Glu Asn Asp
            100                 105                 110

Ala Asp Ser Thr Ala Ser Ile Ser Ala Cys Asn Gly Leu Lys Gly His
        115                 120                 125

Phe Lys Leu Gln Gly Glu Met Tyr Leu Ile Glu Pro Leu Lys Leu Ser
    130                 135                 140

Asp Ser Glu Ala His Ala Val Phe Lys Leu Lys Asn Val Glu Lys Glu
145                 150                 155                 160

Asp Glu Ala Pro Lys Met Cys Gly Val Thr Gln Asn Trp Glu Ser Tyr
                165                 170                 175

Glu Pro Ile Lys Lys Ala Ser Asp Leu Asn Leu Asn Pro Glu His Gln
            180                 185                 190

Arg Tyr Val Glu Leu Phe Ile Val Val Asp His Gly Met Tyr Thr Lys
        195                 200                 205

Tyr Asn Gly Asp Ser Asp Lys Ile Arg Gln Arg Val His Gln Met Val
    210                 215                 220

Asn Ile Met Lys Glu Ser Tyr Thr Tyr Met Tyr Ile Asp Ile Leu Leu
225                 230                 235                 240

Ala Gly Ile Glu Ile Trp Ser Asn Gly Asp Leu Ile Asn Val Gln Pro
                245                 250                 255

Ala Ser Pro Asn Thr Leu Asn Ser Phe Gly Glu Trp Arg Glu Thr Asp
            260                 265                 270

Leu Leu Lys Arg Lys Ser His Asp Asn Ala Gln Leu Leu Thr Ser Ile
        275                 280                 285

Ala Phe Asp Glu Gln Ile Ile Gly Arg Ala Tyr Ile Gly Gly Ile Cys
    290                 295                 300

Asp Pro Lys Arg Ser Thr Gly Val Val Gln Asp His Ser Glu Ile Asn
305                 310                 315                 320
```

-continued

```
Leu Arg Val Ala Val Thr Met Thr His Glu Leu Gly His Asn Leu Gly
                325                 330                 335

Ile His His Asp Thr Asp Ser Cys Ser Cys Gly Gly Tyr Ser Cys Ile
            340                 345                 350
Met Ser Pro Val Ile Ser Asp Glu Pro Ser Lys Tyr Phe Ser Asp Cys
        355                 360                 365

Ser Tyr Ile Gln Cys Trp Glu Phe Ile Met Asn Gln Lys Pro Gln Cys
    370                 375                 380

Ile Leu Lys Lys Pro Leu Arg Thr Asp Thr Val Ser Thr Pro Val Ser
385                 390                 395                 400
Gly Asn Glu Leu Leu Glu Ala Gly Ile Glu Cys Asp Gly Gly Ser Leu
                405                 410                 415

Glu Asn Pro Cys Cys Tyr Ala Thr Thr Cys Lys Met Arg Pro Gly Ser
            420                 425                 430
Gln Cys Ala Glu Gly Leu Cys Cys Asp Gln Cys Arg Phe Met Lys Lys
        435                 440                 445

Gly Thr Val Cys Arg Val Ser Met Val Asp Arg Asn Asp Asp Thr Cys
    450                 455                 460

Thr Gly Gln Ser Ala Asp Cys Pro Arg Asn Gly Leu Tyr Gly
465                 470                 475

<210> SEQ ID NO 15
<211> LENGTH: 6
<212> TYPE: PRT
<213> ORGANISM: Artificial Sequence
<220> FEATURE:
<223> OTHER INFORMATION: RGD PEPTIDE

<400> SEQUENCE: 15

Gly Arg Gly Asp Ser Pro
1               5
```